US012788312B2

(12) United States Patent
Kang et al.

(10) Patent No.: US 12,788,312 B2

(45) Date of Patent: Nov. 10, 2026

(54) MOTORIZED ORTHOPEDIC TENSOR AND METHODS OF USING THE SAME

(71) Applicant: MAKO Surgical Corp., Weston, FL (US)

(72) Inventors: Hyosig Kang, Weston, FL (US); Kevin Bechtold, Davie, FL (US); Jason Karl Otto, Sioux Falls, SD (US); Snehal Kasodekar, Weston, FL (US); Peter L. Ebbitt, Boca Raton, FL (US); David Gene Bowling, Los Ranchos De Albuquerque, NM (US)

(73) Assignee: MAKO Surgical Corp., Weston, FL (US)

( * ) Notice: Subject to any disclaimer, the term of this patent is extended or adjusted under 35 U.S.C. 154(b) by 303 days.

(21) Appl. No.: 18/754,224

(22) Filed: Jun. 26, 2024

(65) Prior Publication Data

US 2025/0000444 A1 Jan. 2, 2025

Related U.S. Application Data

(60) Provisional application No. 63/524,241, filed on Jun. 30, 2023.

(51) Int. Cl.

*A61B 5/00* (2006.01)

*A61B 5/11* (2006.01)

(Continued)

(52) U.S. Cl.

CPC .......... *A61B 5/4585* (2013.01); *A61B 5/0053* (2013.01); *A61B 5/1114* (2013.01); (Continued)

(58) Field of Classification Search

None

See application file for complete search history.

(56) References Cited

U.S. PATENT DOCUMENTS

| | | | |
|---|---|---|---|
| 4,501,266 | A | 2/1985 | McDaniel |
| 4,524,766 | A | 6/1985 | Petersen |

(Continued)

FOREIGN PATENT DOCUMENTS

| | | | |
|---|---|---|---|
| CN | 111759312 | A | 10/2020 |
| CN | 215424671 | U | 1/2022 |

(Continued)

OTHER PUBLICATIONS

Babazadeh, Sina et al., "The Relevance of Ligament Balancing in Total Knee Arthroplasty: How Important is it? A Systematic Review of the Literature", Orthopedic Reviews, vol. 1:e26, 2009, 9 pages.

(Continued)

*Primary Examiner* — Jason M Sims

*Assistant Examiner* — Matthew Eric Ogles

(74) *Attorney, Agent, or Firm* — Howard & Howard Attorneys PLLC

(57) ABSTRACT

Systems and methods related to an orthopedic tensor for a knee joint. The tensor is motorized and operates in a force control mode and a displacement control mode. A control system controls the tensor in the force control mode to apply forces to the knee joint until a predetermined force is reached. The control system captures a plurality of force-displacement data pairs from the tensor as a result of the forces applied by the tensor in the force control mode. Control of the tensor is switched from the force control mode to the displacement control mode to perform an extension test whereby a displacement of the tensor is progressively decreased according to displacements from the plurality of force-displacement data pairs until the knee joint can reach an acceptable full extension pose during, or after completion of, the extension test.

31 Claims, 32 Drawing Sheets

(51) Int. Cl.
*A61B 17/00* (2006.01)
*A61B 17/02* (2006.01)

(52) U.S. Cl.
CPC ............ *A61B 5/6847* (2013.01); *A61B 5/742* (2013.01); *A61B 17/025* (2013.01); *A61B 2017/00017* (2013.01); *A61B 2017/00398* (2013.01); *A61B 2017/0268* (2013.01); *A61B 2562/0247* (2013.01)

(56) References Cited

U.S. PATENT DOCUMENTS

| | | | |
|---|---|---|---|
| 5,470,354 | A | 11/1995 | Hershberger et al. |
| 5,630,820 | A | 5/1997 | Todd |
| 5,669,914 | A | 9/1997 | Eckhoff |
| 5,733,292 | A | 3/1998 | Gustilo et al. |
| 6,022,377 | A | 2/2000 | Nuelle et al. |
| 6,056,756 | A | 5/2000 | Eng et al. |
| 6,648,896 | B2 | 11/2003 | Overes et al. |
| 6,758,850 | B2 | 7/2004 | Smith et al. |
| 7,153,281 | B2 | 12/2006 | Holmes |
| 7,156,853 | B2 | 1/2007 | Muratsu |
| 7,442,196 | B2 | 10/2008 | Fisher et al. |
| 7,615,055 | B2 | 11/2009 | DiSilvestro |
| 7,635,369 | B2 | 12/2009 | Cinquin et al. |
| 7,651,500 | B2 | 1/2010 | Supper et al. |
| 7,927,336 | B2 | 4/2011 | Rasmussen |
| 8,197,489 | B2 | 6/2012 | Chessar et al. |
| 8,231,631 | B2 | 7/2012 | Lavallee et al. |
| 8,303,597 | B2 | 11/2012 | Rasmussen |
| 8,317,797 | B2 | 11/2012 | Rasmussen |
| 8,323,290 | B2 | 12/2012 | Metzger et al. |
| 8,337,508 | B2 | 12/2012 | Lavallee et al. |
| 8,394,104 | B2 | 3/2013 | DiSilvestro |
| 8,551,023 | B2 | 10/2013 | Sherman et al. |
| 8,556,830 | B2 | 10/2013 | Sherman et al. |
| 8,562,617 | B2 | 10/2013 | Chessar et al. |
| 8,597,210 | B2 | 12/2013 | Sherman et al. |
| 8,721,568 | B2 | 5/2014 | Rock et al. |
| 8,734,454 | B2 | 5/2014 | DiSilvestro |
| 8,740,817 | B2 | 6/2014 | Sherman et al. |
| 8,945,026 | B2 | 2/2015 | Moser et al. |
| 8,968,192 | B2 | 3/2015 | Protopsaltis |
| 9,008,757 | B2 | 4/2015 | Wu |
| 9,119,655 | B2 | 9/2015 | Bowling et al. |
| 9,216,097 | B2 | 12/2015 | Hauri et al. |
| 9,381,011 | B2 | 7/2016 | Ruhling et al. |
| 9,492,179 | B2 | 11/2016 | Rasmussen |
| 9,538,953 | B2 | 1/2017 | Sherman et al. |
| 9,597,158 | B2 | 3/2017 | Colwell, Jr. et al. |
| 9,603,665 | B2 | 3/2017 | Bowling et al. |
| 9,649,119 | B2 | 5/2017 | Rock et al. |
| 9,655,628 | B2 | 5/2017 | Boyer et al. |
| 9,782,249 | B2 | 10/2017 | Hauri et al. |
| 9,808,356 | B2 | 11/2017 | Haight et al. |
| 10,070,973 | B2 | 9/2018 | Sherman et al. |
| 10,136,952 | B2 | 11/2018 | Couture et al. |
| 10,154,836 | B2 | 12/2018 | D'Lima et al. |
| 10,206,791 | B2 | 2/2019 | D'Lima et al. |
| 10,206,792 | B2 | 2/2019 | Sherman et al. |
| 10,390,737 | B2 | 8/2019 | Malackowski et al. |
| 10,470,780 | B2 | 11/2019 | Bonutti |
| 10,485,530 | B2 | 11/2019 | Ruhling et al. |
| 10,499,997 | B2 | 12/2019 | Weinstein et al. |
| 10,537,444 | B2 | 1/2020 | Mantovani et al. |
| 10,582,918 | B2 | 3/2020 | Moholkar |
| 10,624,650 | B2 | 4/2020 | Rasmussen |
| 10,722,385 | B2 | 7/2020 | Paszicsnyek |
| 10,729,417 | B2 | 8/2020 | Cole et al. |
| 10,772,617 | B2 | 9/2020 | Cole et al. |
| 10,863,995 | B2 | 12/2020 | Nielsen et al. |
| 10,864,045 | B2 | 12/2020 | Nikou et al. |
| 10,874,525 | B2 | 12/2020 | Lerat et al. |
| 11,103,229 | B2 | 8/2021 | Corpa De La Fuente et al. |
| 11,291,437 | B2 | 4/2022 | Trabish et al. |
| 11,291,507 | B2 | 4/2022 | Stawiaski et al. |
| 11,642,118 | B1 | 5/2023 | Kellar et al. |
| 11,812,978 | B2 | 11/2023 | Trabish et al. |
| 11,877,807 | B2 | 1/2024 | Cameron et al. |
| 12,064,358 | B2 | 8/2024 | Otto et al. |
| 12,150,657 | B2 | 11/2024 | Greber |
| 2005/0177170 | A1 | 8/2005 | Fisher et al. |
| 2005/0234332 | A1 | 10/2005 | Murphy |
| 2006/0081063 | A1 | 4/2006 | Neubauer et al. |
| 2006/0241640 | A1 | 10/2006 | Briard et al. |
| 2007/0219561 | A1 | 9/2007 | Lavallee |
| 2007/0233144 | A1 | 10/2007 | Lavallee et al. |
| 2009/0018544 | A1 | 1/2009 | Heavener |
| 2010/0249790 | A1 | 9/2010 | Roche |
| 2012/0172762 | A1* | 7/2012 | Boyer .................... A61B 34/20 600/587 |
| 2012/0330429 | A1 | 12/2012 | Axelson, Jr. et al. |
| 2013/0023794 | A1 | 1/2013 | Stein et al. |
| 2013/0023795 | A1 | 1/2013 | Stein et al. |
| 2013/0165940 | A1* | 6/2013 | DiSilvestro ............. A61F 2/461 606/88 |
| 2014/0094715 | A1 | 4/2014 | Stein et al. |
| 2014/0276949 | A1 | 9/2014 | Staunton et al. |
| 2015/0157335 | A1 | 6/2015 | Rasmussen |
| 2016/0278754 | A1* | 9/2016 | Todorov .................. A61F 2/389 |
| 2017/0245872 | A1 | 8/2017 | Rock et al. |
| 2018/0049895 | A1 | 2/2018 | Haight et al. |
| 2018/0132949 | A1 | 5/2018 | Merette et al. |
| 2018/0221008 | A1 | 8/2018 | Todorov et al. |
| 2018/0317898 | A1 | 11/2018 | Plaskos et al. |
| 2019/0053859 | A1 | 2/2019 | Couture et al. |
| 2019/0083080 | A1 | 3/2019 | D'Lima et al. |
| 2019/0151118 | A1 | 5/2019 | D'Lima et al. |
| 2019/0167448 | A1 | 6/2019 | Sherman et al. |
| 2019/0240045 | A1 | 8/2019 | Couture |
| 2019/0262203 | A1 | 8/2019 | Kang |
| 2019/0269526 | A1 | 9/2019 | Trabish et al. |
| 2019/0290253 | A1 | 9/2019 | Trabish et al. |
| 2019/0290451 | A1 | 9/2019 | Trabish et al. |
| 2019/0358056 | A1 | 11/2019 | Lerat et al. |
| 2020/0015977 | A1 | 1/2020 | de Beaubien et al. |
| 2020/0085419 | A1 | 3/2020 | Ruhling et al. |
| 2020/0289050 | A1 | 9/2020 | Moctezuma de la Barrera et al. |
| 2020/0375760 | A1 | 12/2020 | Paszicsnyek |
| 2020/0405280 | A1 | 12/2020 | Rasmussen |
| 2021/0030427 | A1 | 2/2021 | Rasmussen |
| 2022/0031473 | A1 | 2/2022 | Carter et al. |
| 2022/0096222 | A1 | 3/2022 | Huff et al. |
| 2022/0133505 | A1* | 5/2022 | Couture ................. A61B 90/02 606/102 |
| 2022/0183768 | A1 | 6/2022 | Otto et al. |
| 2022/0202403 | A1 | 6/2022 | D'Lima et al. |
| 2022/0241040 | A1 | 8/2022 | Hladio et al. |
| 2023/0181326 | A1 | 6/2023 | Zhao et al. |
| 2023/0181338 | A1 | 6/2023 | Zhou et al. |
| 2023/0329813 | A1 | 10/2023 | Abbasi et al. |
| 2024/0307075 | A1 | 9/2024 | Leveille et al. |

FOREIGN PATENT DOCUMENTS

| | | | |
|---|---|---|---|
| CN | 215425326 | U | 1/2022 |
| CN | 114847887 | B | 12/2022 |
| CN | 117442396 | B | 4/2024 |
| DE | 10348585 | A1 | 4/2005 |
| DE | 10335410 | B4 | 8/2008 |
| EP | 1475044 | B1 | 8/2007 |
| WO | 2004004576 | A1 | 1/2004 |
| WO | 2005023120 | A1 | 3/2005 |
| WO | 2017218928 | A1 | 12/2017 |
| WO | 2020033589 | A1 | 2/2020 |
| WO | 2020033579 | A9 | 5/2020 |
| WO | 2020132441 | A1 | 6/2020 |

(56) References Cited

FOREIGN PATENT DOCUMENTS

| | | | |
|---|---|---|---|
| WO | 2021061548 | A2 | 4/2021 |
| WO | 2021247990 | A1 | 12/2021 |

OTHER PUBLICATIONS

Matsuda, Shuichi et al., "Ligament Balancing in Total Knee Arthroplasty—Medial Stabilizing Technique", Asia-Pacific Journal of Sports Medicine, Arthroscopy, Rehabilitation and Technology, vol. 2, 2015, pp. 108-113.

Machine-assisted English language abstract and machine-assisted English translation for DE 103 48 585 A1 extracted from espacenet. com database on Jun. 26, 2024, 10 pages.

English language abstract and machine-assisted English translation for DE 103 35 410 B4 extracted from espacenet. com database on Jun. 26, 2024, 10 pages.

English language abstract and machine-assisted English translation for EP 1 475 044 B1 extracted from espacenet. com database on Jun. 26, 2024, 25 pages.

English language abstract for WO 2004/004576 A1 extracted from espacenet.com database on Jun. 26, 2024, 2 pages.

English language abstract and machine-assisted English translation for WO 2005/023120 A1 extracted from espacenet.com database on Jun. 26, 2024, 9 pages.

Partial International Search Report for Application No. PCT/US2024/035528 dated Oct. 22, 2024, 3 pages.

English language abstract and machine-assisted English translation for CN 111759312 A extracted from espacenet.com database on Feb. 4, 2025, 16 pages.

English language abstract and machine-assisted English translation for CN 215425326 U extracted from espacenet.com database on Feb. 4, 2025, 17 pages.

English language abstract and machine-assisted English translation for CN 215424671 U extracted from espacenet.com database on Feb. 4, 2025, 22 pages.

English language abstract and machine-assisted English translation for CN 114847887 B extracted from espacenet.com database on Feb. 4, 2025, 19 pages.

English language abstract and machine-assisted English translation for CN 117442396 B extracted from espacenet.com database on Feb. 4, 2025, 20 pages.

* cited by examiner

| Force (N) | Medial (mm) | Lateral (mm) |
|---|---|---|
| 130 | mb | lb |
| 120 | ma | la |
| 110 | m1 | l1 |
| 100 | m2 | l2 |
| 90 | m3 | l3 |
| 80 | m4 | l4 |
| 70 | m5 | l5 |

FIG. 44
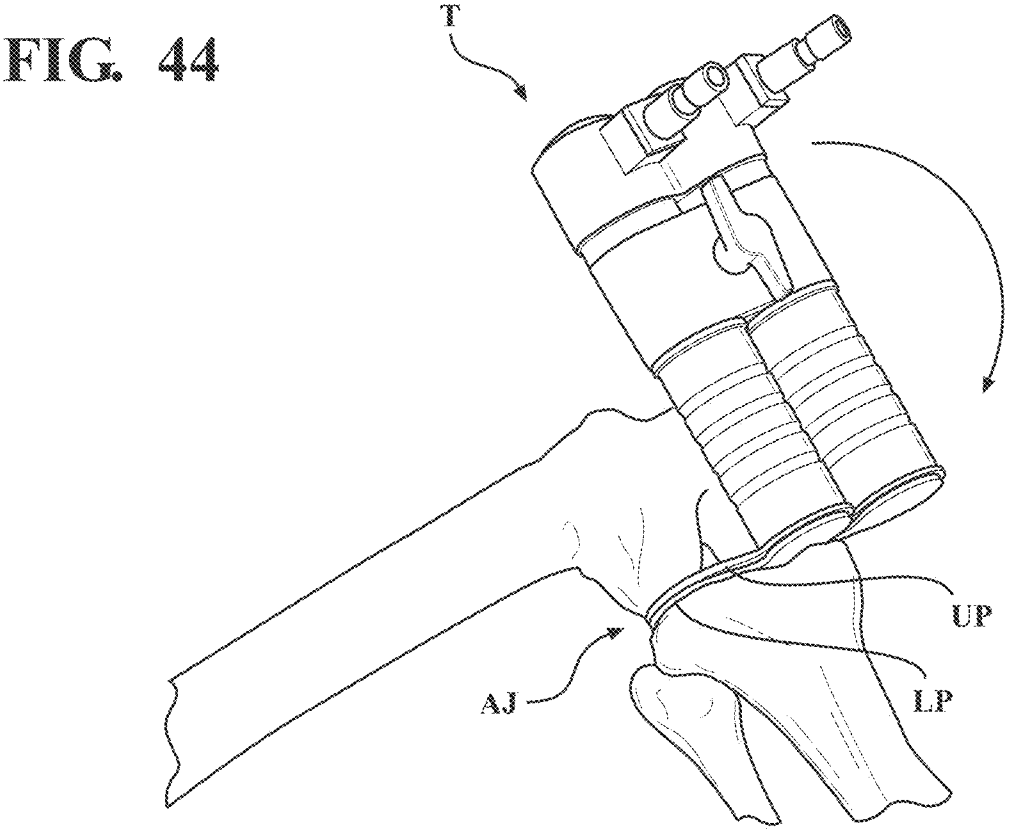
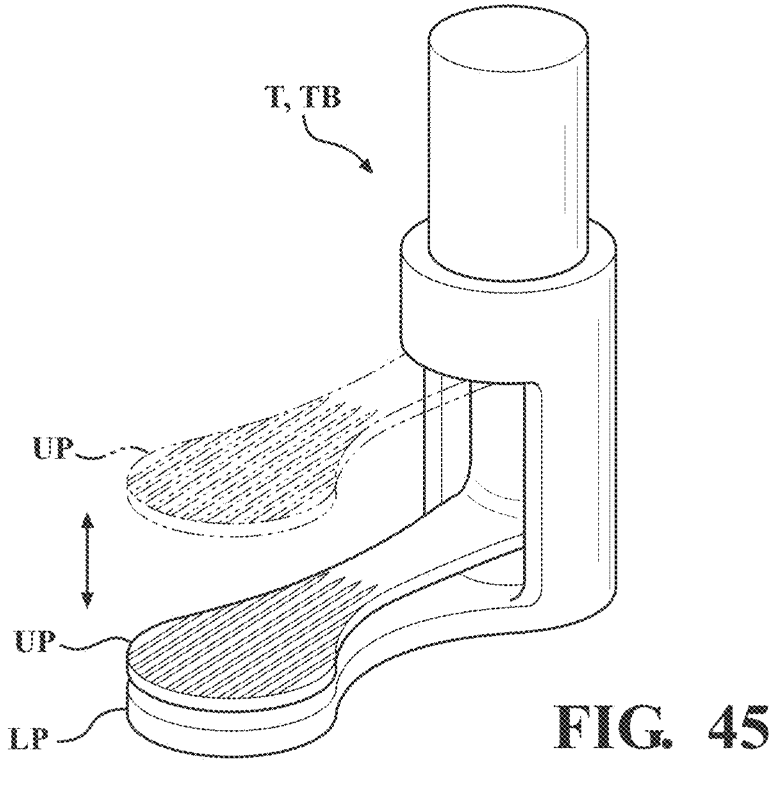
FIG. 45

MOTORIZED ORTHOPEDIC TENSOR AND METHODS OF USING THE SAME

CROSS-REFERENCE TO RELATED APPLICATIONS

The subject application claims priority to and all the benefits of U.S. Provisional Patent App No. 63/524,241, filed Jun. 30, 2023, the entire contents of which are hereby incorporated by reference.

BACKGROUND

Knee arthroplasty involves replacement of articular surfaces of the knee joint to restore function. An important part of a successful knee arthroplasty procedure involves evaluating the soft tissue or ligaments of the knee joint to ensure proper stability, laxity, stiffness, and/or range of motion of the joint. To date, many surgeons still prefer to assess the knee joint ligaments using traditional, manual methods and devices.

One known device for evaluating the knee joint is a knee distractor which has one or more upper paddles for engaging the femur and a lower paddle for engaging the tibia. The paddles move apart to provide a measurement related to the force or spacing between the joint. However, conventional distractors have many shortcomings.

Conventional distractors have limited adjustability. For example, conventional distractors can be “one-size-fits-all” and not configured to accommodate various sized bones of the knee joint. In attempt to accommodate larger sized bones, these types of distractors require a bulky size, which increases the difficulty of inserting the distractor into the knee. Some conventional distractors configurations are limited to only evaluate either the left knee or the right knee, but not both. For example, some conventional distractors include curved paddles to avoid impingement with the patellar tendon. However, the curved paddles may not be removable, and hence, are designed to circumvent the patellar tendon for only the left or right knee. To circumvent the patellar tendon on both knees, some conventional designs require the curved paddles to be removed and replaced with a different (oppositely curved) set of paddles. Replacing these components prolongs the evaluation process (during which the patient is under anesthesia) and increases complexity and cost.

Conventional distractors are at risk of slipping out of the knee joint during the evaluation process. Slippage can cause potential damage to the knee joint, inaccurate measurements, and inconvenience to the surgeon. This issue is particularly prominent with mid-resection workflows, wherein the tibia is resected prior to the evaluation. The rigid, minimally adjustable, configurations of conventional distractors have limited contact coverage of the paddle with the corresponding bone and, in turn, increases susceptibility to slippage. Alternatively, conventional distractors require the lower paddle to be invasively fastened to the resected tibial plane to reduce slippage. Fastening the lower paddle to the resected tibia adds additional surgical steps and trauma to the bone.

Conventional distractors also are not optimized for cleaning or sterilization. Some distractors include exposed parts, such as springs, actuators, or measurement devices that require thorough sterilization and are susceptible to damage from the sterilization process. Time consuming disassembly of components of the distractor may be needed for cleaning or other purposes. The sterilized components are at risk of failure or wear and tear.

Most conventional distractors are not motorized and do not utilize the advantages of computer aid, such as surgical navigation and/or clinical applications. Therefore, the surgeon often must rely on their subjective knowledge and skill to predict the state of the joint ligaments. In turn, the joint evaluation and surgical outcome can be sub-optimal with conventional distractors. One particularly challenging part of the knee evaluation process involves determining the optimal laxity of the knee joint required to enable the knee to reach full extension. Distracting the knee at 0 degrees (full extension) will likely produce inaccurate measurements due to posterior capsule tightness. To assess the tension of the knee at full extension, surgeons typically use a trial-and-error process in which the surgeon inserts the manual distractor in a mid-flexion pose and uses an educated guess to set the tension of the distractor. The knee is then moved towards full extension. If the knee is unable to reach full extension, the surgeon must reset the tension of the distractor and repeat the assessment. Such a process prolongs the evaluation process, produces sub-optimal results, and is inconvenient to the surgeon.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a tensor is provided that is motorized and wherein the tensor is configured to operate in a force control mode to apply forces to an anatomical joint until a predetermined force is reached; capture a plurality of force-displacement data pairs as a result of the forces applied by the tensor in the force control mode; and operate in a displacement control mode whereby a displacement of the tensor is progressively decreased according to displacements from the plurality of force-displacement data pairs.

According to a second aspect, a method is provided of operating a tensor that is motorized, the method comprising: operating the tensor in a force control mode for applying forces to an anatomical joint until a predetermined force is reached; capturing a plurality of force-displacement data pairs resulting from the tensor applying forces in the force control mode; and operating the tensor in a displacement control mode by progressively decreasing a displacement of the tensor according to displacements from the plurality of force-displacement data pairs.

According to a third aspect, a surgical system is provided which is configured to evaluate an anatomical joint, the surgical system comprising: a tensor that is motorized and configured to operate in a force control mode and a displacement control mode; and a control system configured to control the tensor and being configured to: control the tensor in the force control mode to apply forces to the anatomical joint until a predetermined force is reached; capture a plurality of force-displacement data pairs from the tensor as a result of the forces applied by the tensor in the force control mode; and control the tensor in the displacement control mode whereby a displacement of the tensor is progressively decreased according to displacements from the plurality of force-displacement data pairs.

According to a fourth aspect, a method is provided of utilizing a surgical system for evaluating an anatomical joint, the surgical system comprising a tensor that is motorized and configured to operate in a force control mode and a displacement control mode, and a control system configured to control the tensor, the method comprising: controlling, with the control system, the tensor in the force control mode for applying forces to the anatomical joint until a predetermined force is reached; capturing, with the control system, a plurality of force-displacement data pairs from the tensor resulting from the tensor applying forces in the force control mode; and controlling, with the control system, the tensor in the displacement control mode by progressively decreasing a displacement of the tensor according to displacements from the plurality of force-displacement data pairs.

According to a fifth aspect, a surgical system is provided which is configured to evaluate a knee joint, the surgical system comprising: a tensor that is motorized and configured to operate in a force control mode and a displacement control mode; and a control system configured to control the tensor and being configured to: control the tensor in the force control mode to apply forces to the knee joint until a predetermined force is reached; capture a plurality of force-displacement data pairs from the tensor as a result of the forces applied by the tensor in the force control mode; and control the tensor to switch from the force control mode to the displacement control mode and control the tensor in the displacement control mode to perform an extension test whereby a displacement of the tensor is progressively decreased according to displacements from the plurality of force-displacement data pairs until the knee joint can reach an acceptable full extension pose during, or after completion of, the extension test.

According to a sixth aspect, a method is provided of utilizing a surgical system for evaluating a knee joint, the surgical system comprising a tensor that is motorized and configured to operate in a force control mode and a displacement control mode, and a control system configured to control the tensor, the method comprising: controlling, with the control system, the tensor in the force control mode for applying forces to the knee joint until a predetermined force is reached; capturing, with the control system, a plurality of force-displacement data pairs from the tensor resulting from the tensor applying forces in the force control mode; and controlling, with the control system, the tensor for switching from the force control mode to the displacement control mode and controlling the tensor in the displacement control mode for performing an extension test by progressively decreasing a displacement of the tensor according to displacements from the plurality of force-displacement data pairs until the knee joint can reach an acceptable full extension pose during, or after completion of, the extension test.

According to a seventh aspect, an orthopedic tensor is provided, comprising: a body; an upper paddle movable relative to the body and configured to engage a first bone of an anatomical joint; a lower paddle coupled to the body and configured to engage a second bone of the anatomical joint; a drive assembly disposed within the body and comprising an electric motor, and a displacement mechanism coupled between the electric motor and the upper paddle, and wherein the electric motor is configured to move the displacement mechanism to linearly displace the upper paddle relative to the lower paddle; and a sensor configured to sense force applied to the upper paddle, wherein the sensor is located in the displacement mechanism.

According to an eighth aspect, an orthopedic tensor is provided, comprising: a body; an upper paddle movable relative to the body and configured to engage a first bone of an anatomical joint; a lower paddle coupled to the body and configured to engage a second bone of the anatomical joint; a drive assembly coupled to the body and comprising an electric motor, and a displacement mechanism coupled between the electric motor and one, or both of, the upper paddle and the lower paddle, and wherein the electric motor is configured to move the displacement mechanism to displace the upper paddle and/or the upper paddle relative to one another; and a sensor configured to sense force applied to one, or both of, the upper paddle and the lower paddle, wherein the sensor is configured to move in accordance with movement of the displacement mechanism.

According to a ninth aspect, an orthopedic tensor is provided comprising: a first body; a first set of paddles coupled to the first body, the first set of paddles comprising a first upper paddle movable relative to the first body and configured to engage a first bone of an anatomical joint and a first lower paddle configured to engage a second bone of the anatomical joint; a second body separate from the first body; a second set of paddles coupled to the second body, the second set of paddles comprising a second upper paddle moveable relative to the second body and configured to engage the first bone of the anatomical joint and a second lower paddle configured to engage the second bone of the anatomical joint; and a retainer configured to hold the first body and the second body relative to one another, wherein the first body is configured to rotate within the retainer to enable rotational adjustment of the first set of paddles, and wherein the second body is configured to rotate within the retainer to enable rotational adjustment of the second set of paddles; and wherein a locking mechanism is coupled to the retainer and configured to be actuated to rotationally lock one, or both, of the first body and the second body relative to the retainer.

According to a tenth aspect, a retainer is provided for an orthopedic tensor, the retainer defining a first sleeve configured to receive a first body of the tensor and a second sleeve configured to receive a second body of the tensor, wherein the retainer enables the first body to rotate within the first sleeve to enable rotational adjustment of the first set of paddles, and enables the second body to rotate within the second sleeve to enable rotational adjustment of the second set of paddles, and wherein a locking mechanism is coupled to the retainer and configured to rotationally lock one, or both, of the first body and the second body relative to the retainer.

According to an eleventh aspect, an orthopedic tensor is provided comprising: a first body; a first set of paddles coupled to the first body, the first set of paddles comprising a first upper paddle movable relative to the first body and configured to engage a first bone of an anatomical joint and a first lower paddle configured to engage a second bone of the anatomical joint; a second body separate from the first body; a second set of paddles coupled to the second body, the second set of paddles comprising a second upper paddle moveable relative to the second body and configured to engage the first bone of the anatomical joint and a second lower paddle configured to engage the second bone of the anatomical joint; and a link portion coupled between the first body and the second body, the link portion comprising one or more joints configured to enable adjustment of the first body and the second body so as to enable adjustment of the first set of paddles and the second set of paddles; wherein a locking mechanism is coupled to the link portion and is configured to be actuated to lock the one or more joints so as to lock the first body and the second body relative to one another.

According to a twelfth aspect, a retainer is provided for an orthopedic tensor, the retainer defining a first sleeve configured to receive a first body of the tensor and a second sleeve configured to receive a second body of the tensor, wherein the retainer comprises a link portion coupled between the first sleeve and the second sleeve, the link portion comprising one or more joints configured to enable adjustment of the first body and the second body so as to enable adjustment of the first set of paddles and the second set of paddles; wherein a locking mechanism is coupled to the link portion and is configured to be actuated to lock the one or more joints so as to lock the first body and the second body relative to one another.

According to a thirteenth aspect, an assembly is provided for evaluating an anatomical joint which comprises a first bone and a second bone, the assembly comprising: an orthopedic tensor comprising a lower paddle and an upper paddle, and a drive assembly configured to move the upper paddle relative to the lower paddle; and an auxiliary paddle that is configured to be inserted between and captured by the upper paddle and the lower paddle, wherein the auxiliary paddle comprises a distal portion that extends beyond a distal end of each of the upper paddle and lower paddle after the auxiliary paddle is captured, wherein the distal portion is configured to contact the first and second bones of the anatomical joint.

According to a fourteenth aspect, a method is provided of utilizing an assembly for evaluating an anatomical joint which comprises a first bone and a second bone, the assembly comprising an orthopedic tensor comprising a lower paddle and an upper paddle, and a drive assembly to move the upper paddle relative to the lower paddle, and an auxiliary paddle comprising a distal portion, the method comprising: inserting the auxiliary paddle between the upper paddle and the lower paddle; controlling the orthopedic tensor to move the upper paddle towards the lower paddle with the auxiliary paddle inserted therebetween; and capturing the auxiliary paddle between the upper paddle and lower paddle such that the distal portion of the auxiliary paddle is extending beyond a distal end of each of the upper paddle and lower paddle; and utilizing the distal portion of the auxiliary paddle to contact the first and second bones of the anatomical joint.

According to a fifteenth aspect, an auxiliary paddle is provided that is configured to be used with an orthopedic tensor for evaluating an anatomical joint which comprises a first bone and a second bone, the orthopedic tensor comprising a lower paddle and an upper paddle, and a drive assembly to move the upper paddle relative to the lower paddle, wherein the auxiliary paddle comprises: a body that is configured to be inserted between and captured by the upper paddle and lower paddle of the orthopedic tensor; and a distal portion coupled to body and being configured to extend beyond a distal end of each of the upper paddle and lower paddle, wherein the distal portion is configured to contact the first and second bones of the anatomical joint.

According to a sixteenth aspect, an auxiliary paddle is provided that is configured to be used with an orthopedic tensor, wherein the auxiliary paddle comprises: a body; a distal portion coupled to body and configured to contact non-resected surfaces of a first bone and second bone of an anatomical joint; and a pivot being provided on the body and/or coupled to the distal portion.

According to a seventeenth aspect, an orthopedic tensor is provided comprising: a body; an upper paddle coupled to the body and configured to engage a first bone of an anatomical joint; a lower paddle coupled to the body and configured to engage a second bone of the anatomical joint; and a load cell configured to sense force applied to one of the upper paddle or lower paddle, wherein the load cell is incorporated into the one of the upper paddle or lower paddle.

According to an eighteenth aspect, a paddle is provided for an orthopedic tensor, the paddle comprising: a paddle base that is configured to removably attach to the orthopedic tensor; a paddle surface that extends from the base and is configured to engage a bone of the anatomical joint; and a load cell configured to sense force applied to the paddle, wherein the load cell is incorporated into the paddle base or the paddle surface.

According to a nineteenth aspect, an orthopedic tensor assembly is provided comprising: first body; a first set of paddles coupled to the first body, the first set of paddles comprising a first upper paddle movable relative to the first body and configured to engage a first bone of an anatomical joint and a first lower paddle configured to engage a second bone of the anatomical joint; a second body coupled to the first body; a second set of paddles coupled to the second body, the second set of paddles comprising a second upper paddle moveable relative to the second body and configured to engage the first bone of the anatomical joint and a second lower paddle configured to engage the second bone of the anatomical joint; and a spacer configured to be coupled to a paddle of the first or second set of paddles.

According to a twentieth aspect, a surgical system is provided that is configured to evaluate a knee joint, the surgical system comprising: a tensor comprising a body supporting: a first paddle and a second paddle that are configured to interact with the knee joint; and a sensing system configured to sense: a force applied to at least one of the first and second paddles, and/or a displacement between the first and second paddles; and a control system coupled to the tensor being configured to: obtain a sensed value of force and/or displacement from the sensing system; utilize the sensed value to predict a deflection of one or both of the first paddle and the second paddle; and update the sensed value based on the predicted deflection.

Computer-implemented methods and/or computer program products (or non-transitory computer readable mediums) are provided for operating, or that are configured to operate, any surgical system, tensor, assembly, or paddle of any aspect.

Any of the above aspects can be combined in part, or in whole, with any other aspect. Any of the aspects above can be combined in part, or in whole, with any of the following implementations:

The control system can control the tensor in the force control mode to apply forces to the knee joint until the predetermined force is reached when a current pose of the knee joint is at a first acceptable flexion pose. The knee joint includes a femur and a tibia, and the surgical system can include a localizer and a display device, and wherein the control system can: track a pose of the femur and a pose of the tibia with the localizer; control the display device to provide visual guidance to aid in placing the current pose of the knee joint in the first acceptable flexion pose; capture, with the localizer, the current pose of the knee joint relative to the first acceptable flexion pose; and/or control the display device to provide a visual confirmation in response to the current pose of the knee joint being at the first acceptable flexion pose. The first acceptable flexion pose can be a value between 2-15 degrees of knee joint flexion, such as 10 degrees. The control system can control the display device to provide a visual representation of a current pose of the knee joint based on the poses of the femur and the tibia tracked by the localizer. The control system can measure a gap of the knee joint based on the pose of the femur and the tibia tracked by the localizer. The control system can capture, with the localizer, the current pose of the knee joint relative to the acceptable full extension pose and/or control the display device to provide a visual confirmation in response to the current pose of the knee joint being at the acceptable full extension pose. The acceptable full extension pose can be a value from 0-2 degrees of knee joint flexion, such as 0 degrees. The control system can generate a look-up table based on the plurality of force-displacement data pairs captured from the tensor and/or perform the extension test according to displacements from the look-up table. The control system can capture a target displacement of the tensor at a time when the predetermined force was reached, the target displacement being indicative of a target gap of the knee joint. Prior to performing the extension test, the control system can control the tensor in the displacement control mode to place the tensor at the target displacement and/or perform the extension test by progressively decreasing the displacement of the tensor starting from the target displacement. The control system can perform the extension test by automatically and progressively decreasing the displacement of the tensor and optionally according to displacements from the plurality of force-displacement data pairs. The tensor can comprise a user control input, such as a control button or slider. The control system can perform the extension test by progressively decreasing the displacement of the tensor in response to the user control input and optionally according to displacements from the plurality of force-displacement data pairs. During, or after completion of, the extension test, the control system can identify a first force-displacement data pair that enabled the knee joint to reach the acceptable full extension pose. After completion of the extension test, the control system can control the tensor to switch from the displacement control mode to the force control mode and optionally control the tensor in the force control mode to apply a second predetermined force to the knee joint when the knee joint is in a second acceptable flexion pose. The control system can control the tensor in the force control mode for applying a second predetermined force to the knee joint when the knee joint is in a second acceptable flexion pose. The control system can control the display device to provide visual guidance to aid in placing a current pose of the knee joint at the second acceptable flexion pose, and/or capture the current pose of the knee joint relative to the second acceptable flexion pose and/or control the display device to provide a visual confirmation in response to the current pose of the knee joint being at the second acceptable flexion pose. The second acceptable flexion pose can be a value from 80-105 degrees of knee joint flexion, such as 90 degrees. The control system can obtain the second predetermined force from a force from the first force-displacement data pair that enabled the knee joint to reach the acceptable full extension pose. The control system can obtain the second predetermined force from one of: a predetermined joint balancing force, a force based on a surgeon preference, a force obtained from statistical data, or a force from any of the force-displacement data pairs. While the knee joint is at the second acceptable flexion pose and during, or after, application of the second predetermined force to the knee joint, the control system can capture a second force-displacement data pair from the tensor. The control system can determine parameters of the knee joint based on the first force-displacement data pair that enabled the knee joint to reach the acceptable full extension pose and based on the second force-displacement data pair identified while the knee joint was at the second acceptable flexion pose. The parameters can be laxity parameters, such as laxity of medial and lateral compartments of the knee joint. The knee joint can include a femur with medial and lateral condyles and a tibia, and wherein the tensor further comprises a medial upper paddle and a lateral upper paddle that are each separately movable and can respectively engage the medial and lateral condyles of the femur, and at least one lower paddle can engage the tibia. In one example, first and second lower paddles of the first body and the second body collectively engage the tibia. The tensor can comprise a drive assembly comprising a first electric motor, and a first displacement mechanism coupled between the first electric motor and the medial upper paddle. The tensor can comprise a second electric motor, and a second displacement mechanism coupled between the second electric motor and the lateral upper paddle. The tensor can include a first sensor to sense force applied to the medial upper paddle. The tensor can include a second sensor to sense force applied to the lateral upper paddle. The control system can control the tensor in the force control mode by commanding the medial upper paddle and the lateral upper paddle to respectively apply forces to the medial and lateral condyles of the femur until the predetermined force is reached for one or both the medial upper paddle and the lateral upper paddle. The control system can capture the plurality of force-displacement data pairs further based on measurements from the first and second sensors and displacements of the medial upper paddle and the lateral upper paddle. The control system can control the tensor in the displacement control mode to perform the extension test by progressively decreasing the displacement of the medial upper paddle and the lateral upper paddle according to displacements from the plurality of force-displacement data pairs.

The sensor can include one or more of a load cell, strain gauge, pressure sensor, a displacement sensor, hall effect sensor, encoder, or the like. The sensor can move in accordance with movement of the displacement mechanism. The displacement mechanism can comprise a ball screw coupled to the electric motor and that can be rotated by the electric motor. The displacement mechanism can comprise a ball screw nut that can engage the ball screw. The ball screw nut can linearly displace along the ball screw pursuant to rotation of the ball screw by the electric motor. The displacement mechanism can comprise a ball spline shaft fixed to the ball screw nut and fixed to the upper paddle. The ball spline shaft can be linearly displaced in accordance with movement of the ball screw nut. The ball spline shaft can comprise a threaded interface that can receive a fastener. A variety of different sized upper paddles can attach to the tensor, such as by attaching to the ball spline shaft with the fastener. The tensor can receive a plurality of different sized lower paddles. The sensor can be located between the ball screw nut and the ball spline shaft, or between any other components of the displacement mechanism, such as any component within the load path of force applied to the upper paddle. The displacement mechanism can comprise an adapter disposed between the ball screw nut and the ball spline shaft. The adapter can be threaded to the ball screw nut. The adapter can be fixed to the ball spline shaft. The sensor can be located between the adapter and the ball screw nut. The sensor can be ring-shaped or disc shaped. The sensor can be disposed around the ball screw. The body of the tensor can be hermetically sealed. The body can be a first body and the tensor can include a second body that can be coupled relative to the first body. An upper paddle can be movable relative to the second body and can engage the first bone of the anatomical joint. A lower paddle can be coupled to the second body and can engage the second bone of the anatomical joint. A drive assembly can be disposed within the second body and can include an electric motor, and a displacement mechanism coupled between the electric motor and the upper paddle, and wherein the electric motor can move the displacement mechanism to linearly displace the upper paddle relative to the lower paddle. A sensor can sense force applied to the upper paddle, wherein the sensor is located in the displacement mechanism of the second body. The first body can be hermetically sealed. The second body can be hermetically sealed independent of the first body. The first and second bodies can be completely separated from one other.

A retainer can couple the first body and the second body relative to one another. The retainer can release the first body and the second body from the retainer such that the first body and the second body can be separated from one another. The retainer can define a first sleeve can receive the first body. The retainer can define a second sleeve can receive the second body. The first sleeve and second sleeve each can have a cylindrical configuration to hold a cylindrical portion of the first body and cylindrical portion of the second body, respectively. The sleeves can have any other shape (such as oval, rectangular, triangular, polygonal, etc.) to conform to the correspondingly shaped outer surface of the first and second bodies. Each of the first body and the second body can have a circumferential, annular, or perimeter-based feature that can respectively engage the first sleeve and the second sleeve to axially lock the first body and second body relative to the retainer. The locking mechanism can comprise a first locking mechanism coupled to the first sleeve and that can be actuated to rotationally lock the first body to the first sleeve. The locking mechanism can include a second locking mechanism coupled to the second sleeve and that can be actuated to rotationally lock the second body to the second sleeve. Each of the first sleeve and the second sleeve can include a size, opening, width, length, or a diameter that is adjustable. The locking mechanism can be actuated to simultaneously decrease the size, opening, width, length, or a diameter of each of the first and second sleeves to rotationally lock the first body and the second body relative to the retainer. The retainer can be split into a first portion and a second portion. Each of the first and second portions can partially define the first and second sleeves. The locking mechanism can be actuated to bring the first portion and the second portion of the retainer closer together to simultaneously and rotationally lock the first body and the second body relative to the retainer. Each of the first portion and the second portions can define inner teeth. Each of the first body and the second body can define outer teeth. The locking mechanism can be actuated to bring the first portion and the second portion closer together such that the inner teeth collectively engage to the outer teeth to simultaneously and rotationally lock the first body and the second body relative to the retainer. The retainer can comprise the first sleeve and the second sleeve being spaced apart from each other and a link portion connected between the first sleeve and the second sleeve. The link portion can be rigidly fixed between the first sleeve and the second sleeve. The first and second sleeves can be fixed relative to one another. The link portion can be adjustable. The link portion can include a rotational joint that can enable rotational movement between the first sleeve and the second sleeve and/or a prismatic joint that can enable translational movement between the first sleeve and the second sleeve. The locking mechanism or a separate locking mechanism can be actuated to lock the link portion. The locking mechanism or a separate locking mechanism can be couple to the one or more joints. When the link portion comprises one or more rotational joints, the rotational joints can enable rotational adjustment of the first body and the second body so as to enable rotational adjustment of the first set of paddles and the second set of paddles and the locking mechanism can to be actuated to lock the one or more rotational joints so as to rotationally lock the first body and the second body relative to one another. When the link portion comprises one or more translational joints, the translational joints can enable translational adjustment of the first body and the second body so as to enable translational adjustment of the first set of paddles and the second set of paddles and the locking mechanism can to be actuated to lock the one or more translational joints so as to translationally lock the first body and the second body relative to one another. The one or more joints can be spherical joints or gimbal joints. The locking mechanism can be at least one knob disposed external to the retainer and can be rotated in a first direction to rotationally lock the first body and the second body relative to the retainer and rotated in a second direction to rotationally unlock one, or both, of the first body and the second body relative to the retainer. The locking mechanism can be at least one lever disposed external to the retainer and moved in a first direction to rotationally lock one, or both, of the first body and the second body relative to the retainer moved in a second direction to rotationally unlock one, or both, of the first body and the second body relative to the retainer. The locking mechanism can be at least one button disposed external to the retainer and pushed to rotationally lock one, or both, of the first body and the second body relative to the retainer and/or pushed to rotationally unlock one, or both, of the first body and the second body relative to the retainer. The first electric motor can move the first displacement mechanism to linearly displace the first upper paddle along a first axis relative to the first lower paddle and the first body can rotate about the first axis within the retainer. The second electric motor can move the second displacement mechanism to linearly displace the second upper paddle along a second axis relative to the second lower paddle and the second body can rotate about the second axis within the retainer.

The orthopedic tensor can include the auxiliary paddle, as part of a kit or assembly. The orthopedic tensor can command movement of the upper paddle and/or the lower paddle relative to one another to capture the auxiliary paddle therebetween. The auxiliary paddle can be secured to the orthopedic tensor solely by being captured between the upper paddle and the lower paddle. The orthopedic tensor can operate in a force control mode to capture the auxiliary paddle. The orthopedic tensor can include a force sensor to sense force applied to the upper paddle. In the force control mode, the orthopedic tensor can command movement of the upper paddle towards the lower paddle until a predetermined force is detected by the force sensor. The predetermined force can be indicative of the auxiliary paddle being appropriately captured between the upper paddle and the lower paddle. In response to the distal portion contacting the first and second bones, the auxiliary paddle can apply force to the upper paddle. The force sensor can sense force applied to the upper paddle by the auxiliary paddle. The orthopedic tensor can operate in a displacement control mode to capture the auxiliary paddle. The orthopedic tensor can include a displacement sensor to sense displacement between the upper paddle and the lower paddle. In the displacement control mode, the orthopedic tensor can command movement of the upper paddle towards the lower paddle until a predetermined displacement between the upper paddle and lower paddle is detected by the displacement sensor. The predetermined displacement can be indicative of the auxiliary paddle being appropriately captured between the upper paddle and the lower paddle. In response to the distal portion contacting the first and second bones, the auxiliary paddle can apply force to the upper paddle and the displacement sensor can measure displacement between the upper paddle and the lower paddle in response to force applied to the upper paddle by the auxiliary paddle. The auxiliary paddle can pivot to apply force to the upper paddle in response to the distal portion contacting the first and second bones. The auxiliary paddle can include a rocker surface. The rocker surface can be contoured or curved and can engage the lower paddle. The rocker surface can enable the auxiliary paddle to pivot in response to the distal portion contacting the first and second bones. The auxiliary paddle can comprise a top surface opposite the rocker surface. The top surface can be planar and is configured to engage the upper paddle. The distal portion, the rocker surface, and the top surface of the auxiliary paddle can be part of a single, unitary, or monolithic body. The distal portion of the auxiliary paddle can include an auxiliary distal upper paddle that is configured to contact the upper paddle and contact the first bone and can include an auxiliary distal lower paddle that is configured to contact the lower paddle and contact the second bone. The auxiliary distal upper paddle can be pivotable relative to the auxiliary distal lower paddle to apply force to the upper paddle in response to the distal portion contacting the first and second bones. The upper paddle of the tensor is designed to contact the first bone and the lower paddle of the tensor is designed to contact the second bone. When the auxiliary paddle is captured, the distal portion of the auxiliary paddle provides a substitute for the upper paddle and the lower paddle for contacting the first and second bones. The first and second bones of the anatomical joint can be non-resected bones and the lower paddle is designed to engage a resected surface of the second bone. The auxiliary paddle can provide a substitute for the lower paddle to engage non-resected surface of the second bone. The upper paddle of the tensor has a bottom surface configured to engage the auxiliary paddle. The lower paddle has a top surface configured to engage the auxiliary paddle. The bottom surface of the upper paddle and the top surface of the lower paddle can cooperate to capture the auxiliary paddle. The upper paddle and lower paddle of the tensor each a length defined between a proximal end and a distal end. The auxiliary paddle has a length defined between a proximal end and a distal end of the distal portion, wherein the length of the auxiliary paddle can be greater than the length of the upper paddle and greater than the length of the lower paddle. The auxiliary paddle can include a body portion that can rest on the lower paddle. The body portion can have a shape that substantially conforms to a shape of the lower paddle. The tensor body can be used in an inverted or upside-down orientation. The tensor body can have an inverted or upside-down configuration whereby the upper paddle pulls up instead of pushing up on the femur. Spacers can be selectively coupled to any paddle of any tensor configuration.

The inventors have contemplated that any of the implementations above can be combined in part, or in whole with any aspects described herein.

DESCRIPTION OF THE DRAWINGS

Advantages of the present disclosure will be readily appreciated as the same becomes better understood by reference to the following detailed description when considered in connection with the accompanying drawings.

FIG. 44 is a perspective view of the tensor of FIG. 9 being utilized in an inverted, or up-side down orientation whereby the upper paddle engages the tibia and the lower paddle engages the femur, according to one implementation.

FIG. 45 is a perspective view of a tensor body including an inverted, or up-side down configuration whereby the paddles are located near the bottom of the tensor body, instead of the near the top of the tensor body, according to one implementation.

DETAILED DESCRIPTION

I. Example System Overview

Figure 1:
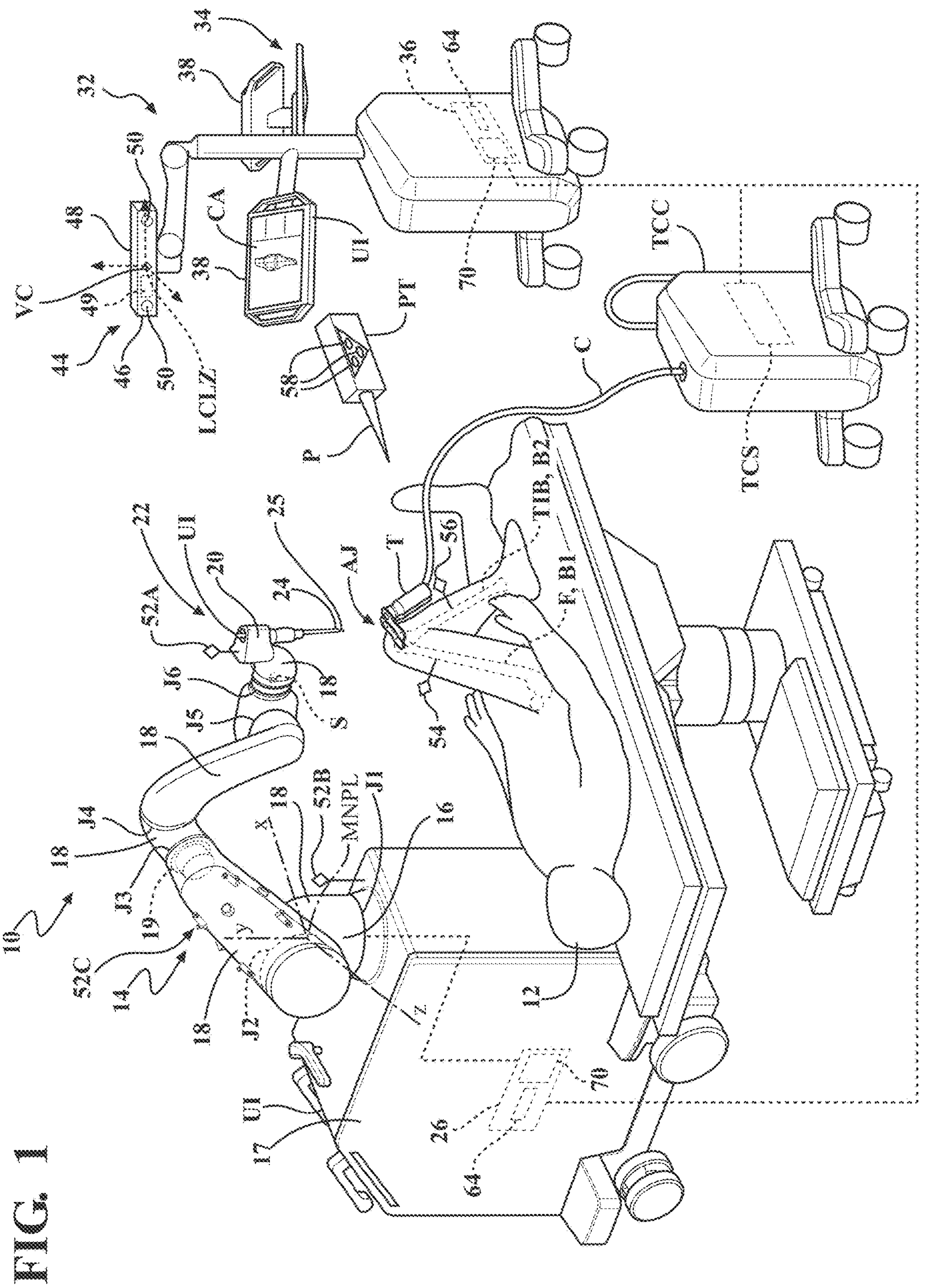
FIG. 1 is a perspective view of a surgical system including an orthopedic tensor, according to one implementation.

Referring to FIG. 1, one example of a surgical system 10 is illustrated. The system 10 is useful for treating or evaluating a surgical site or anatomical volume (A) of a patient 12, such as treating bone or soft tissue. In FIG. 1, the patient 12 is undergoing a surgical procedure. The anatomy in FIG. 1 includes a femur F and a tibia TIB of the patient 12. The surgical procedure may involve tissue removal or other forms of treatment. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/0330429, entitled, "Prosthetic Implant and Method of Implantation," the disclosure of which is hereby incorporated by reference. The system 10 and techniques disclosed herein may be utilized to perform other procedures, surgical or non-surgical, or may be utilized in industrial applications or other applications where robotic systems are utilized.

The system 10 can include a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints J and a plurality of joint encoders 19 located at the joints J for determining position data of the joints J. For simplicity, only one joint encoder 19 is illustrated in FIG. 1, although other joint encoders 19 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 19 but may alternatively, or additionally, utilize motor encoders present on motors at each joint J. Also, the manipulator 14 need not require rotary joints, but may alternatively, or additionally, utilize one or more prismatic joints. Any suitable combination of joint types is contemplated.

The base 16 of the manipulator 14 is a portion of the manipulator 14 that provides a fixed reference coordinate system for other components of the manipulator 14 or the system 10 in general. The origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the manipulator cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 17. In other examples, the manipulator 14 can be a hand-held manipulator where the base 16 is a base portion of a tool (e.g., a portion held free hand by the user) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined.

The manipulator 14 and/or manipulator cart 17 house a manipulator controller 26, or other type of control unit. The manipulator controller 26 may comprise one or more computers, or any other suitable form of controller that directs the motion of the manipulator 14. The manipulator controller 26 may have a central processing unit (CPU) and/or other processors, memory (not shown), and storage (not shown). The manipulator controller 26 is loaded with software as described below. The processors could include one or more processors to control operation of the manipulator 14. The processors can be any type of microprocessor, multi-processor, and/or multi-core processing system. The manipulator controller 26 may additionally, or alternatively, comprise one or more microcontrollers, field programmable gate arrays, systems on a chip, discrete circuitry, and/or other suitable hardware, software, or firmware that is capable of conducting the functions described herein. The term processor is not intended to limit any embodiment to a single processor. The manipulator 14 may also comprise a user interface UI with one or more displays and/or input devices (e.g., push buttons, keyboard, mouse, microphone (voice-activation), gesture control devices, touchscreens, etc.).

A tool 20 couples to the manipulator 14 and is movable relative to the base 16 to interact with the anatomy in certain modes. The tool 20 is a physical and surgical tool and is, or forms part of, an end effector 22 supported by the manipulator 14 in certain implementations. The tool 20 may be grasped by the user. One possible arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

The tool 20 can include an energy applicator 24 designed to contact, evaluate, or remove the tissue of the patient 12 at the surgical site. In one example, the energy applicator 24 is a bur 25. The bur 25 may be substantially spherical and comprise a spherical center, radius (r) and diameter. Alternatively, the energy applicator 24 may be a drill bit, a saw blade, an ultrasonic vibrating tip, or the like. In other examples, the tool 20 does not include an energy applicator 24. For example, the tool 20 can be a slotted cut guide for a saw, a guide tube for receiving another tool, or the like.

The tool 20 may comprise a tool controller to control operation of the tool 20, such as to control power to the tool (e.g., to a rotary motor of the tool 20), control movement of the tool 20, control irrigation/aspiration of the tool 20, and/or the like. The tool controller may be in communication with the manipulator controller 26 or other components. The tool 20 may also comprise a user interface UI with one or more displays and/or input devices (e.g., push buttons, keyboard, mouse, microphone (voice-activation), gesture control devices, touchscreens, etc.). For example, one of the user input devices on the user interface UI of the tool 20 may be a tool input (e.g., switch or other form of user input device) that has first and second input states (see FIG. 1).

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 tracks movement of various objects. Such objects include, for example, the manipulator 14, the tool 20 and the anatomy, e.g., femur F and tibia TIB. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 can include a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, and the like. In some instances, the display 38 can be a head-mounted device that includes a display positioned in front of the eyes of the user. The head-mounted device can be configured to present mixed reality or augmented reality computer images over real-world images of objects or the surgical site. The head-mounted device can display any of the media described herein and can be like that described in U.S. Pat. No. 10,499,997, entitled "Systems and Methods for Surgical Navigation" the entire contents of which are hereby incorporated by reference.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 can include one or more trackers. In one example, the trackers include a pointer tracker PT, one or more manipulator trackers 52A, 52B, 52C a first patient tracker 54, and a second patient tracker 56. In the illustrated example of FIG. 1, the manipulator tracker is coupled to the tool 20 (i.e., tracker 52A), the first patient tracker 54 is firmly affixed to the femur F of the patient 12, and the second patient tracker 56 is firmly affixed to the tibia TIB of the patient 12. In this example, the patient trackers 54, 56 are firmly affixed to sections of bone. The pointer tracker PT is firmly affixed to a pointer P utilized for registering the anatomy to the localizer coordinate system LCLZ. The manipulator trackers 52A, 52B, 52C may be affixed to any suitable component of the manipulator 14, in addition to, or other than the tool 20, such as the base 16 (i.e., tracker 52B), or any one or more links 18 of the manipulator 14 (i.e., tracker 52C). The trackers 52, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object with which it is associated.

Any one or more of the trackers may include active markers 58. The active markers 58 may include light emitting diodes (LEDs). Alternatively, the trackers 52, 54, 56, PT may have passive markers, such as reflectors, which reflect light emitted from the camera unit 46. Other suitable markers not specifically described herein may be utilized.

The localizer 44 can track the trackers 52, 54, 56, PT to determine a state of each of the trackers 52, 54, 56, PT, which correspond respectively to the state of the object respectively attached thereto. The localizer 44 may perform known triangulation techniques to determine the states of the trackers 52, 54, 56, PT, and associated objects. The localizer 44 provides the state of the trackers 52, 54, 56, PT to the navigation controller 36. In one example, the navigation controller 36 determines and communicates the state the trackers 52, 54, 56, PT to the manipulator controller 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, non-transitory memory (not shown), and storage (not shown). The processors can be any type of processor, microprocessor, or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of conducting the functions described herein. The term processor is not intended to limit any embodiment to a single processor.

Although one example of the navigation system 32 is shown that employs triangulation techniques to determine object states, the navigation system 32 may have any other suitable configuration for tracking the manipulator 14, tool 20, and/or the patient 12.

In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the manipulator 14, the tool 20, and/or the patient 12, and generates state signals to the navigation controller 36 based on the ultrasound images. The ultrasound images may be 2-D, 3-D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The manipulator 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56, PT shown in FIG. 1.

In yet another example, the navigation system 32 and/or localizer 44 are electromagnetically based. For example, the navigation system 32 may comprise an EM transceiver coupled to the navigation controller 36. The manipulator 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

In yet another example, the navigation system 32 and/or localizer 44 utilize a machine vision system which includes a video camera coupled to the navigation computer 36. The video camera is configured to locate a physical object in a target space. The physical object has a geometry represented by virtual object data stored by the navigation computer 36. The detected objects may be tools, obstacles, anatomical features, trackers, or the like. The video camera and navigation computer 36 are configured to detect the physical objects using image processing techniques such as pattern, color, or shape recognition, edge detection, pixel analysis, neutral net or deep learning processing, optical character recognition, barcode detection, or the like. The navigation computer 36 can compare the captured images to the virtual object data to identify and track the objects. A tracker may or may not be coupled to the physical object. If trackers are utilized, the machine vision system may also include infrared detectors for tracking the trackers and comparing tracking data to machine vision data. Again, such navigation system 32 examples may have structural configurations that are different than the navigation system 32 configuration as shown throughout the Figures. Examples of machine vision tracking systems can be like that described in U.S. Pat. No. 9,603,665, entitled “Systems and Methods for Establishing Virtual Constraint Boundaries” and/or like that described in U.S. Pat. No. 11,291,507, entitled “Systems and Method for Image Based Registration and Calibration,” the entire contents of which are incorporated by reference herein.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Figure 2:
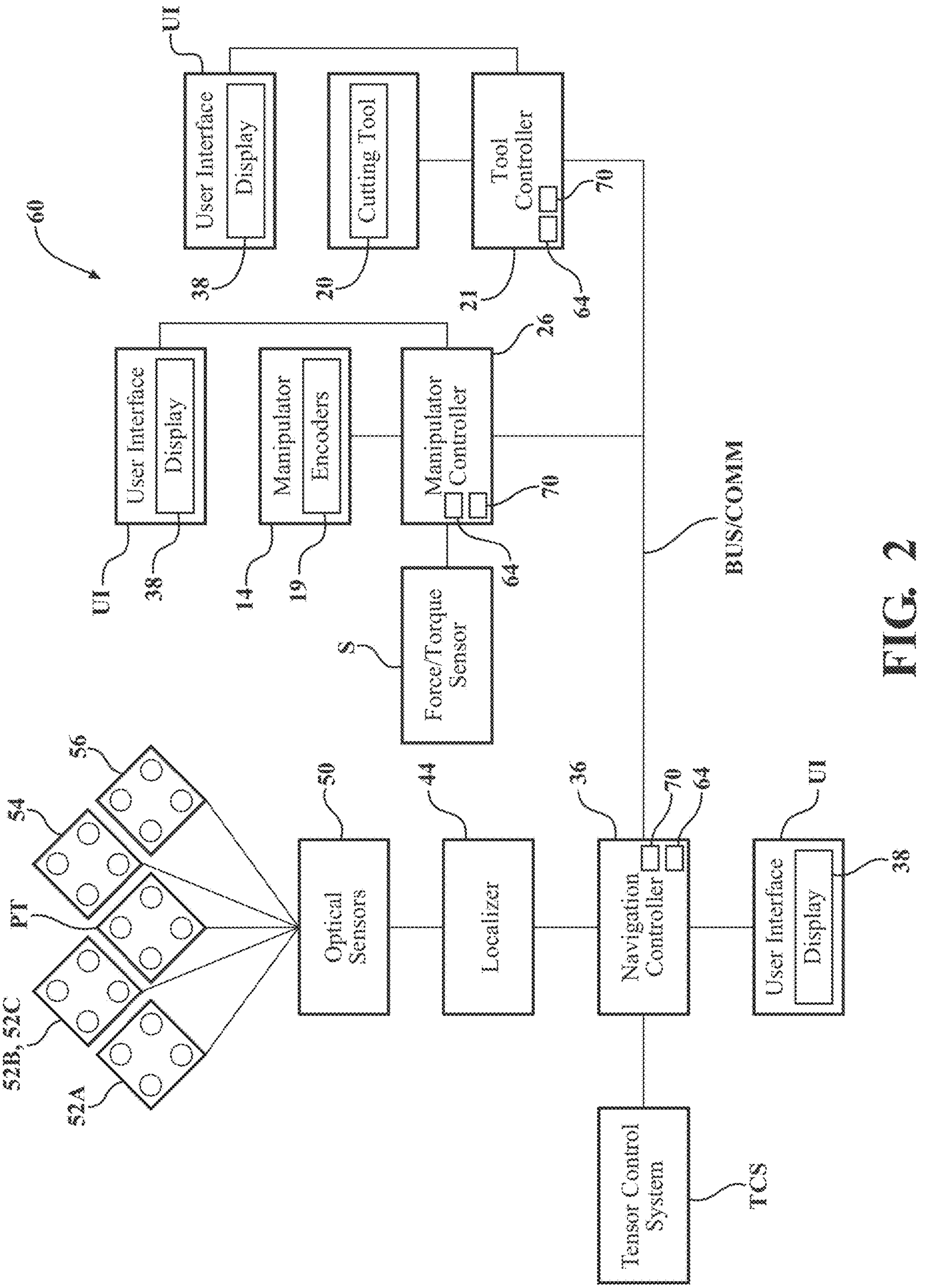
FIG. 2 is a block diagram of an example control system for controlling the surgical system.

Referring to FIG. 2, the system 10 can include a control system 60 that comprises, among other components, the manipulator controller 26, the navigation controller 36, and the tool controller 21. The control system 60 further includes one or more software programs and software modules shown in FIG. 3. The software modules may be part of the program or programs that operate on the manipulator controller 26, navigation controller 36, tool controller 21, or any combination thereof, to process data to assist with control of the system 10. The software programs and/or modules include computer readable instructions stored in non-transitory memory 64 on the manipulator controller 26, navigation controller 36, tool controller 21, or a combination thereof, to be executed by one or more processors 70 of the controllers 21, 26, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 26, navigation controller 36, tool controller 21, or any combination thereof. The user may interact with any of the input devices of the navigation user interface UI or other user interface UI to communicate with the software modules. The user interface software may run on a separate device from the manipulator controller 26, navigation controller 36, and/or tool controller 21.

The control system 60 may comprise any suitable configuration of input, output, and processing devices suitable for conducting the functions and methods described herein. The control system 60 may comprise the manipulator controller 26, the navigation controller 36, or the tool controller 21, or any combination thereof, or may comprise only one of these controllers. These controllers may communicate via a wired bus or communication network as shown in FIG. 2, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of conducting the functions described herein.

A clinical application CA may be provided to manage user interaction. The clinical application CA manages many aspects of user interaction and coordinates the surgical workflow, including pre-operative planning, joint assessment, implant placement, registration, bone preparation visualization, and post-operative evaluation of implant fit, etc. The clinical application CA is configured to output to any of the displays 38.

II. Orthopedic Tensor and Methods

Described in this section are configurations and methods of using an orthopedic tensor T (hereinafter “tensor”) for evaluating an anatomical joint AJ. The anatomical joint AJ chiefly described herein is a knee joint including a femur F and tibia TIB. However, the anatomical joint AJ can be any other joint, such as a hip joint, shoulder joint, elbow joint, ankle joint, etc. The tensor T is inserted into the anatomical joint AJ to evaluate soft tissue and ligaments of the anatomical joint AJ. The tensor T can be used to evaluate laxity, stiffness, ligament balance, kinematics, flexion, extension and/or range of motion of the anatomical joint AJ. Configurations and uses of the orthopedic tensor T will be described in detail below. The tensor T can be used for total knee arthroplasty procedures, partial knee arthroplasty procedures, anatomical shoulder arthroplasty procedures, reverse shoulder arthroplasty procedures, or any other procedure requiring evaluation of adjacent bones. The tensor T can be used to evaluate bones that are pre-resected, mid-resected, post-resected, or one or more bones that include a prosthetic implant coupled to the bone.

In most cases, the tensor T is intended to be held and support by the hand(s) of the user. However, in some examples, the tensor T can be the tool 20 coupled to the manipulator 14. The tensor T can be actively or passively coupled to the manipulator 14. When passively coupled, the tensor T can be held in certain positions by the manipulator 14 to facilitate any of the methods described herein for evaluating the anatomical joint AJ and the user controls the tensor T independent of the robot control. When actively coupled, the manipulator 14 control system can be coupled to control system of the tensor T to coordinate these two systems. The tensor T can be selectively attached to and removed from the manipulator 14 at the desire of the user. The tensor T can be utilized with or without the system 10 described above and can be utilized with any type of surgical system besides the system 10 specifically shown.

A. Tensor Configurations

Figure 3:
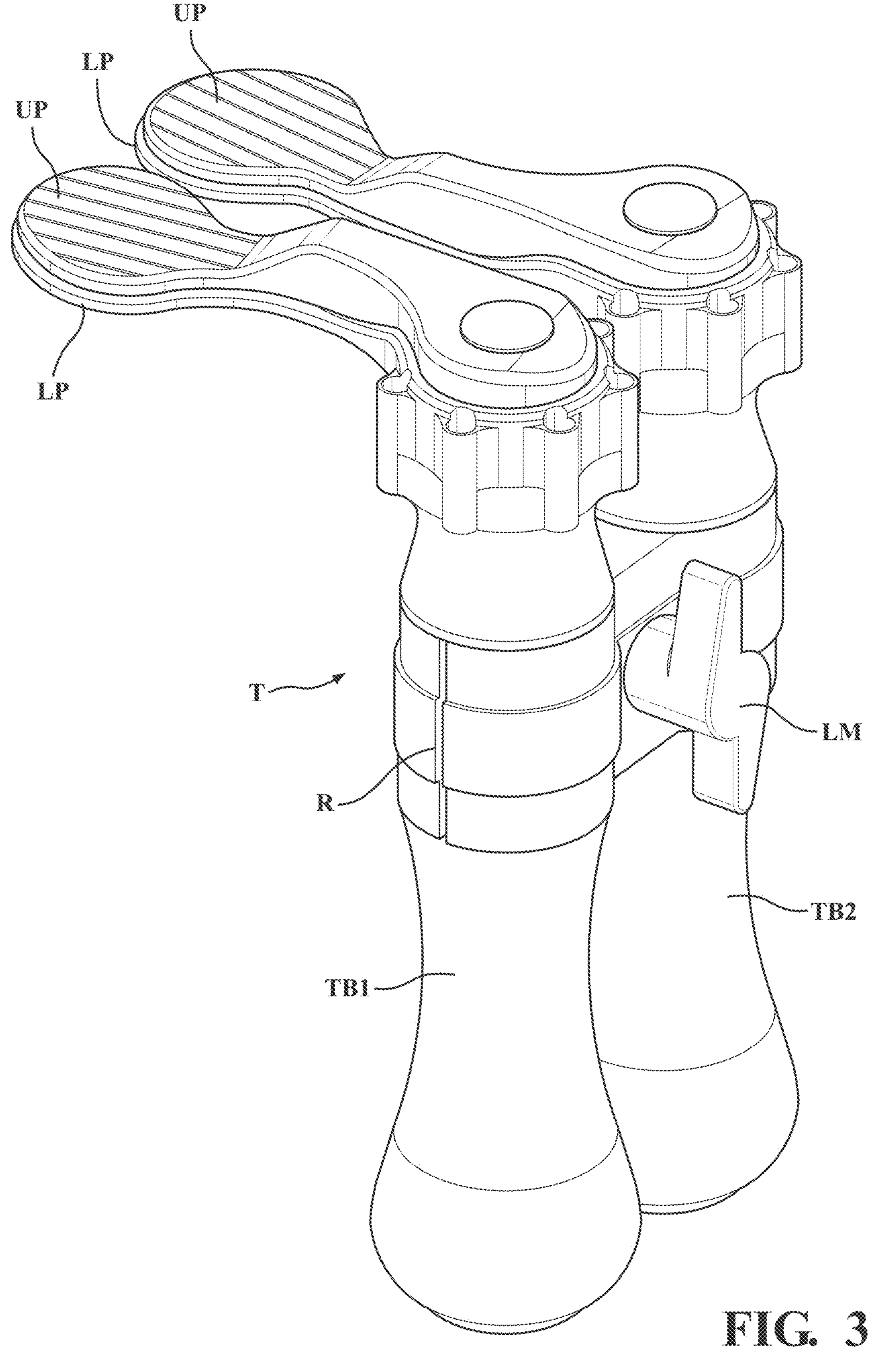
FIG. 3 is a perspective view of the tensor, according to one implementation.

Referring to FIG. 3, one example of the tensor T is illustrated. The tensor T includes a first body TB1 and a second body TB2. The first and second bodies TB1, TB2 are configured to be separated from one another and can be independently operational. In the example shown, the first and second bodies TB1, TB2 are temporarily coupled together and utilized in tandem for evaluating the knee joint AJ. The bodies TB1, TB2 are configured to be grasped by the hand of the surgeon (as one coupled unit or separately). The external surface of each body TB1, TB2 can be contoured to optimize ergonomics and comfort for the user during grasping of the bodies TB1, TB2. Each body TB1, TB2 is hermetically sealed independent of the other body TB1, TB2 such that the internal components of each body TB1, TB2 are not exposed to the sterile field. As will be understood below, the separate bodies TB1, TB2 provide many advantages, such as optimizing adjustability of the tensor T, increasing contact with the bones B1, B2, prolonging life of the tensor T, and improving the cleaning of the tensor T.

The first body TB1 and the second body TB2 each include an upper paddle UP and a lower paddle LP. To separate the bones B1, B2, the upper paddle UP of each body TB1, TB2 is configured to move relative to the lower paddle LP of each body TB1, TB2. Each lower paddle LP is fixed relative to the respective body TB1, TB2. In other configurations, both the upper paddle UP and lower paddle LP can move or the lower paddle LP can move relative to a fixed upper paddle UP. In some configurations, the first and second bodies TB1, TB2 can share a common lower paddle LP.

Figure 4:
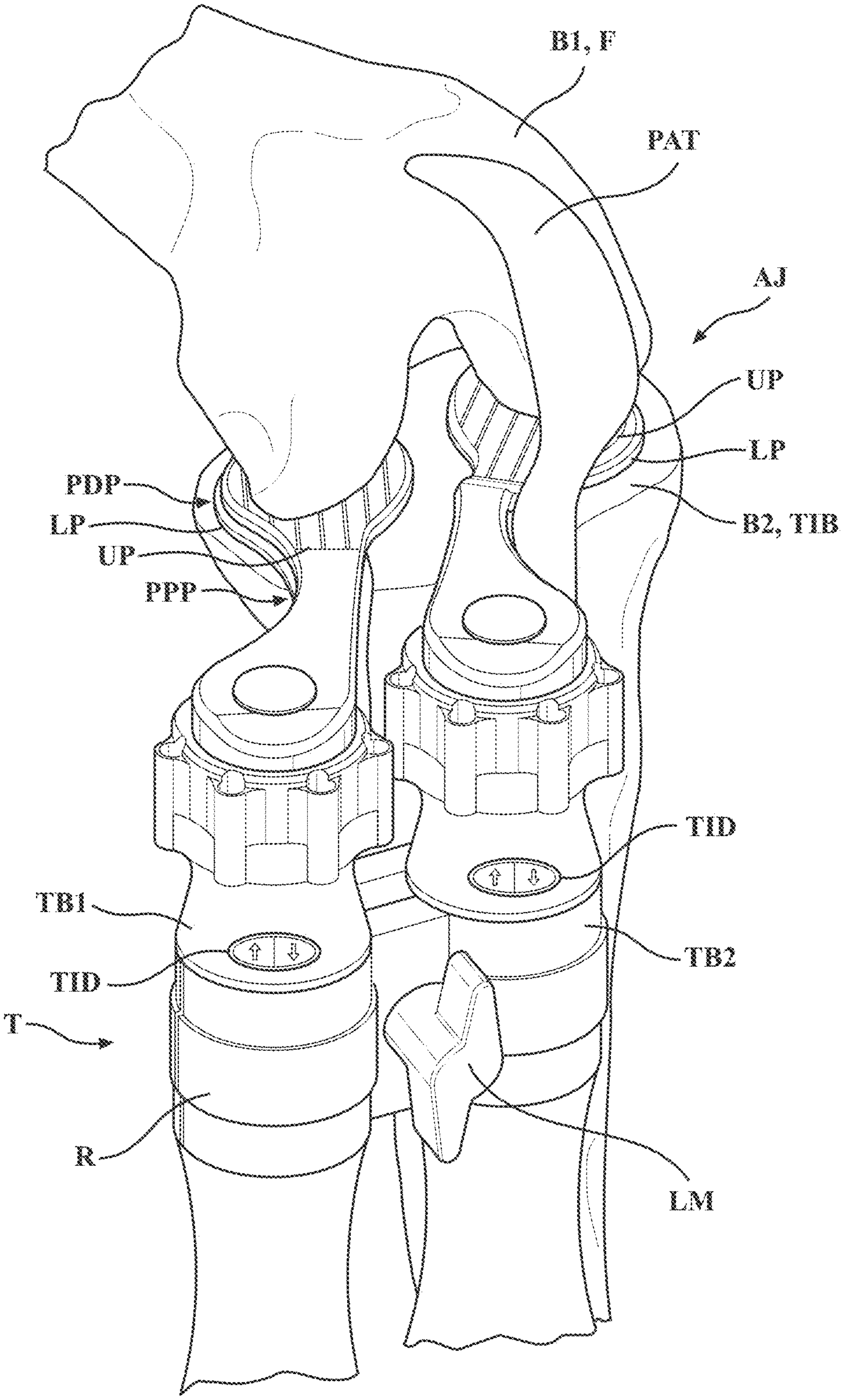
FIG. 4 is a perspective view of the tensor inserted in a knee joint, according to one implementation.

The upper paddle UP of each body TB1, TB2 is configured to engage a first bone B1 of the anatomical joint AJ and the lower paddle LP of each body TB1, TB2 is configured to engage a second bone B2 of the anatomical joint AJ. In FIG. 4, the anatomical joint AJ is a knee joint wherein the first bone B1 is a distal femur F and the second bone B2 is a tibia TIB. In FIG. 4, the tensor T is inserted into the knee joint AJ such that the upper paddle UP of each body TB1, TB2 engages the femur F and the lower paddle of each body TB1, TB2 engages the tibia TIB. In FIG. 4, one upper paddle UP engages a medial compartment or condyle of the femur F and the other upper paddle UP engages a lateral compartment or condyle of the femur F. In FIG. 4, the tibia TIB is a resected as part of a mid-resection workflow. The lower paddle LP of each body TB1, TB2 rests plainly on the resected tibia with sufficient contact coverage and depth so as to not require invasive fastening of each lower paddle LP to the resected tibial plane. However, it is contemplated that the lower paddle LP can optionally be fastened to the resected tibial plane. In the case of a non-resected workflow, the tibial surface may be the native, non-resected surface. The lower paddles LP are also configured to engage a native, non-resected tibial surface. Furthermore, the tensor T can evaluate the knee joint AJ after an implant is implanted in one, or both, of the femur For the tibia TIB. For example, the upper paddles UP can engage a femoral implant with artificial medial and lateral condyles. The lower paddles LP can engage a tibial implant. The tensor T is thus adaptable to various surgical workflows without requiring disassembly or reconfiguration.

1. Tensor Drive Assembly

Figure 5:
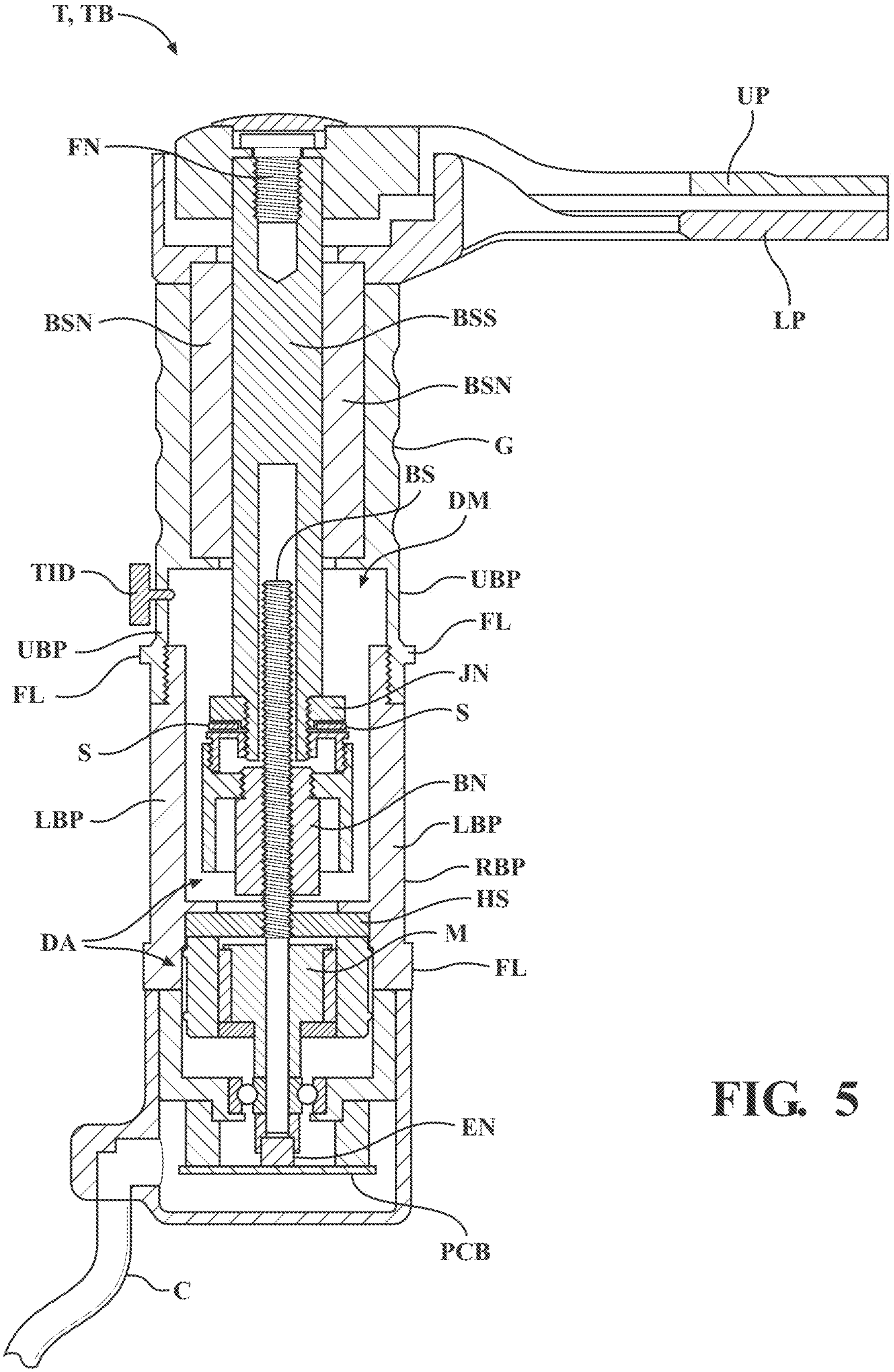
FIG. 5 is partial cross-sectional side view of one body of the tensor having paddles placed in a closed position, according to one implementation.
Figure 6:
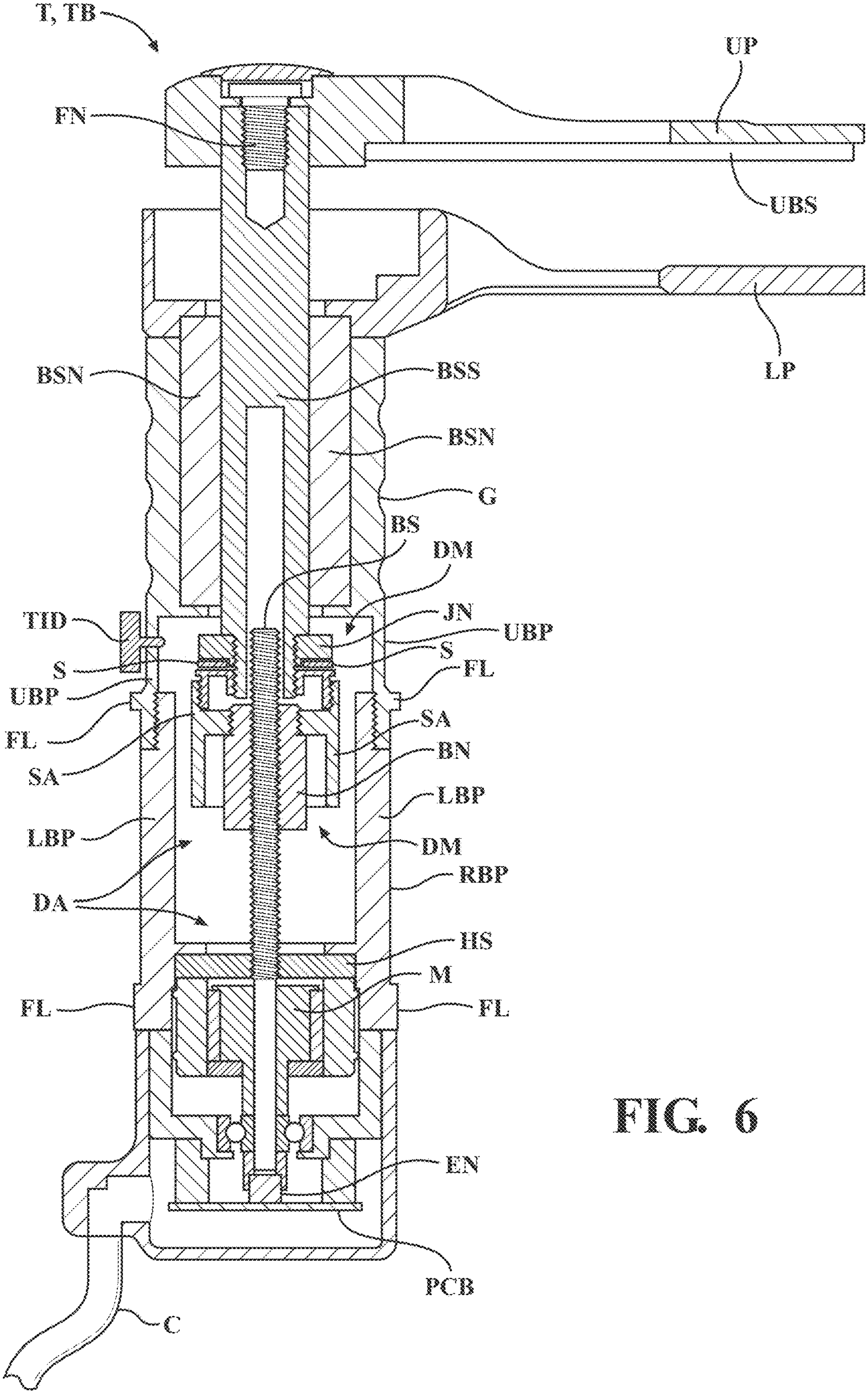
FIG. 6 is partial cross-sectional side view of one body of the tensor having paddles placed in an open position, according to one implementation.

With reference to FIGS. 5 and 6, the various internal components of the tensor T are described. For simplicity, the illustrated components are shown for the first body TB1 of the tensor T. It is understood that the second body TB2 can comprise a similar or identical configuration. Any reference herein to what the first body TB1 may include is fully applicable to what the second body TB1 may include and is not repeated for simplicity.

The first body TB1 includes a drive assembly DA coupled to or disposed within the body TB1. The drive assembly DA includes an electric motor M, such as a brushless DC motor. The motor M is in a fixed position relative to the body TB1. A displacement mechanism DM is coupled between the electric motor M and the upper paddle UP. The electric motor M is configured to move the displacement mechanism DM to linearly displace the upper paddle UP relative to the lower paddle LP. FIG. 5 illustrates the paddles UP, LP in a closed position and FIG. 6 illustrates the paddles UP, LP in an open, spaced, apart, position. Alternatively, the displacement mechanism DM can linearly displace both the upper paddle UP and the lower paddle LP relative to one another.

In one implementation, the displacement mechanism DM can comprise a ball screw BS coupled to the electric motor M and that can be rotated by the electric motor M. A ball screw nut BN can engage the ball screw BS. The ball screw nut BN can linearly move up or down along the ball screw BS pursuant to a direction of rotation of the ball screw BS by the electric motor M. The displacement mechanism DM can comprise a ball spline shaft BSS fixed to the ball screw nut BN and fixed to the upper paddle. The ball spline shaft BSS and ball screw nut BN can be a single unit or separately coupled components. The ball spline shaft BSS can be linearly displaced in accordance with movement of the ball screw nut BN. The upper paddle UP will move in correspondence with the ball spline shaft BSS. The ball spline shaft BSS can include an internal bore to receive and provide clearance for the ball screw BS as the ball spline shaft BSS is axially moved. A ball spline nut BSN can be fixed relative to the body TB1 and can surround the ball spline shaft BSS. The ball spline nut BSN can provide an internal guiding channel and linear bearing surface to facilitate movement of the ball spline shaft BSS. The tight fitting of the ball spline nut BSN also maintains sealing of the internal components of the body TB1 and eliminates the need for a bellows for scaling between the body TB1 and the upper paddle UP. The displacement mechanism DM can also include a jam nut JN disposed between the ball screw nut BN and the ball spline shaft BSS. The jam nut JN moves with the ball screw nut BN and can be provided to stop upward movement of the ball screw nut BN by abutting an internal flange within the body TB1. The ball spline shaft BSS can comprise a threaded interface that can receive a fastener FN. A variety of different sized upper paddles UP can attach to the body TB1, such as by attaching to upper paddle UP to the ball spline shaft BSS with the fastener FN. The upper paddle UP can be removed from the body TB1 by removing the fastener FN. The lower paddle LP is fixed to the body TB1. However, in other configurations, when the upper paddle UP is removed, any one of a variety types of lower paddles LP can be installed to the body TB1 by sliding the lower paddle LP over the ball spline shaft BSS and securing the lower paddle LP to the body TB1.

Above the motor M, a hard stop HS can be provided to stop downward movement of the ball screw nut BN. The hard stop HS can be spaced specifically so that once the ball screw nut BN reaches the hard stop HS, the upper paddle UP will be in a closed position relative to the lower paddle LP, i.e., touching the lower paddle LP, without overdriving the upper paddle UP. The hard stop HS can also protect the motor M from contact by the ball screw nut BN.

Below the motor M, axially, is a printed circuit board PCB supporting operation of the motor and a tensor encoder EN for sensing the rotational position of the motor M. The encoder EN may comprise a magnetic based sensor, such as a Hall effect sensor. The encoder EN can function as a displacement sensor for sensing the displacement of the upper paddle UP relative to the lower paddle LP.

A cable C can be coupled to the tensor T. The cable C is connectable to a power source and/or control system TCS for the tensor T. The cable C can exit to the body TB1 through a cable seal. Control signals for the tensor T can be provided through the cable C. Power to the tensor T components, such as the motor M, PCB, and sensor S can also be provided through the cable C. Alternatively, the body TB1 may be battery (self) powered. A replaceable or rechargeable battery unit can be coupled to the body TB1, such as by attaching to a lower end of the body TB1, e.g., beneath the motor M and PCB. The body TB1 can include battery terminals that interface to corresponding terminals of the battery unit. The battery unit and/or the body TB1 can provide a seal to prevent fluid from reaching the battery terminals. The body TB1 can also include one or more user input devices TID for providing control signals through to the tensor T. The user input devices TID can be coupled to the PCB and can take any form, such as buttons, sliders, knobs, switches, triggers, which are accessible from the external surface of the body and actuated by the user.

The body TB1 can be disassembled. For example, with continued reference to FIGS. 5 and 6, the body TB1 can include a lower body portion LBP that is threadedly coupled to an upper body portion UBP. When disconnected, the lower body portion LBP can retain the motor M, PCB, the ball screw BS, the ball screw nut BN, and the ball spline shaft BSS. The upper body portion UBP can retain the lower paddle LP and the ball spline nut BSN. The upper paddle UP may require unfastening from the ball spline shaft BSS prior to disconnecting the body portions UBP, LBP.

The configuration of the drive assembly DA and the displacement mechanism DM are not limited to the configuration shown and described above. For example, instead of a ball screw system, the displacement mechanism DM could include a lead screw with a carriage, a planetary roller actuator system, a worm gear system, or the like. Any of the features described above, or their equivalents, can be utilized with the second body TB2 of the tensor T.

2. Improved Sensor Configurations

2a. Sensor Included with Displacement Mechanism

With continued reference to FIGS. 5 and 6, the body TB1 of the tensor T comprises a sensor S configured to sense force applied to the upper paddle UP. The force can be applied to the upper paddle UP by the femur F, in which case the force is applied to a top surface of the upper paddle UP which contacts the femur F. Alternatively or additionally, the force can be applied to a bottom surface UBS of the upper paddle UP. For example, by an auxiliary paddle AP inserted between the upper and lower paddles UP, LP, which will be described in detail below. The sensor S can sense any of these forces in any axial direction. In the example shown in FIGS. 5 and 6, the sensor is a load cell. However, the sensor S can include one or more of a load cell, strain gauge, pressure sensor, or the like. The sensor S can sense force upwards of 400 Newtons.

In the example shown, the sensor S is located in the displacement mechanism DM and/or configured to move in accordance with movement of the displacement mechanism DM. In one implementation, the sensor S can be located between the ball screw nut BN and the ball spline shaft BSS. The displacement mechanism DM can comprise a sensor adapter SA disposed between the ball screw nut BN and the ball spline shaft BSS. The sensor adapter SA can be fixed to the ball spline shaft BSS and engaged to the ball screw nut BN with threads. The sensor S can be located between the sensor adapter SA and the ball screw nut BN. The sensor S can be attached directly to the sensor adapter SA or simply captured between the components. The sensor S will move in correspondence with the ball screw nut BN. Alternatively, the sensor S can be located between any other components of the displacement mechanism DM, such as any component in the load path of force applied to the upper paddle UP.

The sensor S can be ring-shaped or disc shaped such that the sensor S can be disposed around the ball screw BS. This annular configuration of the sensor S provides reliable and accurate load measurements for any directional force applied to the upper paddle UP. The sensor S can be wired along the inner surface of the body TB1 to circumvent the path of the ball screw nut BN and avoid pinching of the cable. The sensor S can be connected to the PCB. Again, any reference throughout to what the first body TB1 may include is fully applicable to what the second body TB1 may include and is not repeated for simplicity.

By having the sensor S located in, or moving with, the displacement mechanism DM, the tensor T provides several improvements. The load path between the upper paddle the sensor S is minimized in length because the sensor S is positioned closer to the applied force, thereby improving accuracy in measurement. The motor M can remain in an axially fixed position without being subjected to load from the upper paddle. In other words, the motor M is not required to axially move to enable the sensor S to sense the force because the sensor S is located above the motor M. Having the sensor S below the motor M will require the motor M to experience some axial force and will require additional flexure components to enable movement of the motor M. By having the sensor S in the displacement mechanism, the tensor T eliminates the need for adding complaint, flexure components and increases robustness of the drive assembly DA by maintaining the axial position of the motor M.

2b. Sensor Included with Paddle

Figure 42A:
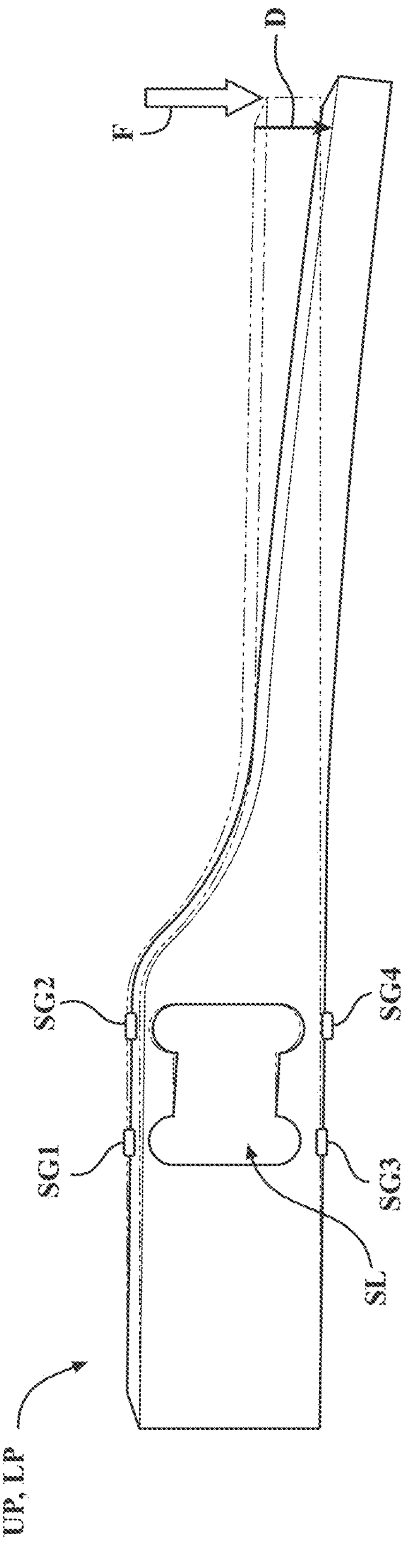
FIG. 42A is a side view of a paddle of the tensor implementing one example of a load cell for measuring force on the paddle, wherein the paddle is shown at-rest and deflected under load, according to one implementation.
Figure 42B:
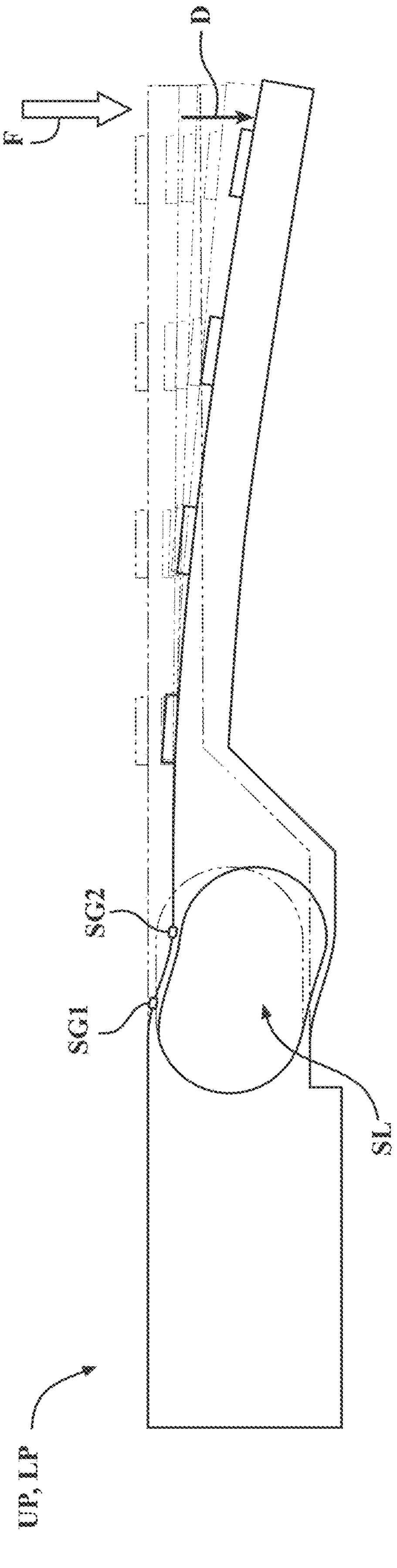
FIG. 42B is a side view of a paddle of the tensor implementing another example of a load cell for measuring force on the paddle, wherein the paddle is shown at-rest and deflected under load, according to another implementation.

In addition to, or instead of, having the sensor S in the displacement mechanism, the sensor S can be included directly with the paddle, as shown in FIGS. 42A and 42B. In the example of FIGS. 42A and 42B, an upper paddle UP is shown for illustrative purposes. However, the descried sensor S configuration can apply to the upper paddle UP, lower paddle LP, or both. In this example, the sensor S is disposed on the paddle UP, LP, disposed in the paddle UP, LP, or incorporated or integrated with the paddle UP, LP.

The paddle UP, LP can be configured with one or more openings or slots SL formed into the body of the paddle UP, LP. The slot SL can have any suitable shape, such as a circle, oval, pill, discorectangle, obround, stadium, rectangle, or any other complex shape. For example, as shown in FIG. 42A, the slot SL (at-rest) is formed by two vertical pill shapes spaced apart and connected by a rectangular shape. The pill shape(s) can extend along the body axis BA or along the axis along which the paddle may move up/down. In another example, as shown in FIG. 42B, the slot SL (at-rest) may be a single pill shape that is horizontally oriented, i.e., parallel or coincident to an axis defined along a length of the paddle UP, LP. The one or more slots SL may be formed to extend entirely through body of the respective paddle UP, LP. Alternatively, the one or more slots SL may be formed to extend partially into the body of the respective paddle UP, LP. In another example, the slot SL can be formed directly into the surface of the respective paddle UP, LP that experiences the force, such as the upper surface of the upper paddle UP that contacts the femur, or the lower surface of the lower paddle LP that contacts the tibia. Other configurations of slots SL are contemplated beyond those specifically shown and described.

The one or more slots SL are configured to deform in response to a load or force (shown as F) applied to the respective paddle UP, LP. The one or more slots SL are configured to provide a pivot point for the respective paddle UP, LP in response to the force applied to the respective paddle UP, LP. By deforming and providing a pivot point, the one or more slots SL enable the respective paddle UP, LP to experience a displacement (D) relative to the at-rest position of the paddle. For example, in response to an applied load to the paddle UP, LP, the one or more slots SL can create a four-bar type mechanism to enable the displacement D of the paddle. The flexion and corresponding displacement D of the paddle UP, LP depends on the magnitude of the applied force and the location and direction of the force relative to the length of the paddle. The respective paddle UP, LP can be formed of any suitable material to enable its deformation, including but not limited to stainless steel, such as 17-4, 440C, or 900 grade stainless steel.

The deformation of the one or more slots SL is proportional to, or correlated to, the applied force. Hence, the deformation of the one or more slots SL can be measured to deduce the respective force F applied to the paddle. The sensor S can be implemented by providing one or more strain gauges SG on the paddle. The strain gauge has wires (not shown) of a resistive element that attach to a surface adjacent to the slot SL. A length of the surface of the slot SL expands or contracts in response to the load. The strain gauge is a passive device that changes resistance in response to changes in strain on the surface adjacent to the slot SL. That is, a length of the wires changes in response to changes in the length of the surface. The resistance of the wires changes in response to changes to the length of the electrical wires. Resistance in the strain gauge increases when the surface goes into tension and the resistance in the strain gauge decreases when the surface goes into compression. Strain is proportional to the change in resistance of the strain gauge. The change in resistance is deduced by measuring the voltage across the strain gauge. Any suitable resistance measuring means may measure the change in electrical resistance. The one or more strain gauges can be located relative to the one or more slots SL. In these configurations, the sensor S can utilize the one or more slots SL and strain gauges SG to implement as a load cell.

In the example of FIG. 42B, two strain gauges SG1, SG2 are disposed on the paddle above the pill shaped slot SL, e.g., disposed above the slot SL and along the flat side of the pill shape. The two strain gauges can form half-bridge configuration. Here, the strain gauges are arranged in series circuit configuration such that if the resistance of one strain gauge goes up, the resistance in the other strain gauge(s) goes down. In the example of FIG. 42A, two strain gauges SG1, SG2 are disposed on the paddle above the slot SL and two other strain gauges SG3, SG4 are disposed on the paddle below the slot SL. For example, each respective strain gauge SG can be disposed above or below the pill shape end. The four strain gauges can form full bridge configuration, which comprises two half bridge configurations arranged in a parallel circuit configuration. The full-bridge configuration more sensitively measures small changes in voltage. The number and location of strain gauges SG can vary depending on whether the paddle is the upper or lower paddle, or the shape of the respective paddle and/or slot SL. Other configurations of strain gauge configurations are contemplated beyond those specifically shown and described.

The strain gauge(s) SG can be coupled to any of the described controller(s), such as the motor controller MC and behavior controller BC, which can be located in the tensor body TB. In one example, this coupling is made through electrical wires. To enable the wires to adapt to movement of the respective paddle UP, LP, the tensor body TB can include a channel for the wire and the wire may include a service loop to provide slack. Alternatively, the strain gauge (s) SG can communicate signals via wireless communication (e.g., radio frequency, or otherwise). A compact wireless communicate device can be embedded within the paddle, for instance.

By incorporating the slot SL and strain gauge SG configuration (e.g., load cell) directly on/into the body of the paddle, the described configurations provide a more compact sensor S design. Moreover, a more accurate force measurement is provided by having the load cell be located directly next to the source of the force on the paddle (e.g., as compared with further away from the force).

3. Paddle Configurations

Figure 11:
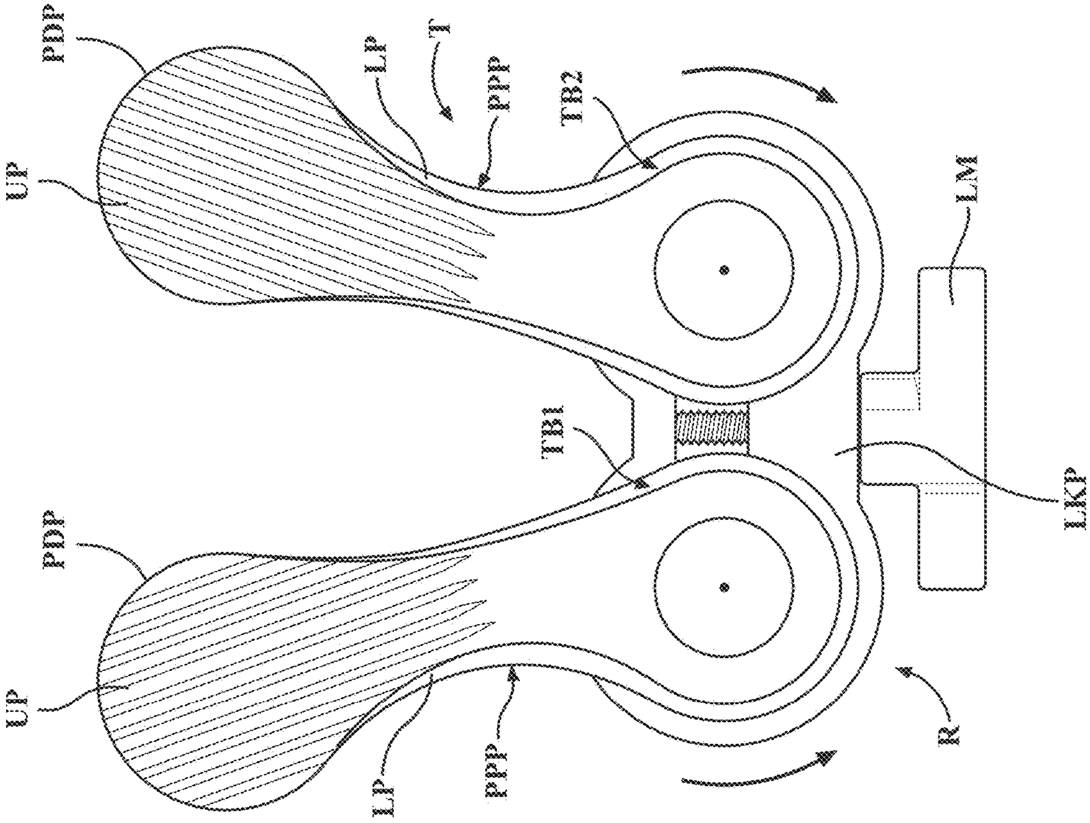
FIG. 11 is a top view of the tensor bodies being disposed within the retainer, wherein the bodies and their respective paddles are rotated in a second configuration, according to one implementation.
Figure 12:
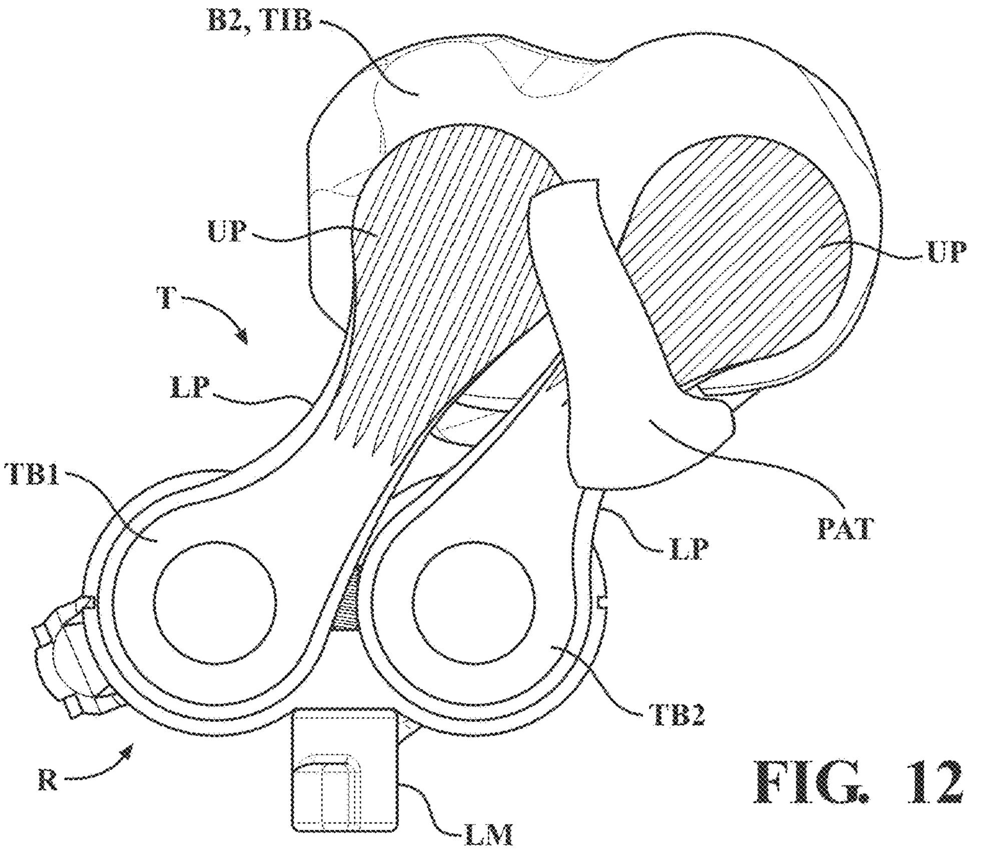
FIG. 12 is a top view of the tensor bodies and their respective paddles being disposed on a resected tibia of a right knee and rotated in a first configuration to enable one set of paddles to circumvent the patellar tendon, according to one implementation.

As shown in at least FIGS. 3 and 10-13, the tensor T is configured to be used a variety of different paddles. As shown in FIG. 3, for example, the upper paddles UP and the lower paddles LP can each have a perimeter profile that correspond to the other. Alternatively, the perimeter profile of the paddles can be different from one another, as shown in FIG. 12. For example, the lower paddle LP can be similar in shape, but slightly wider than the upper paddle UP. As shown in FIG. 3, the upper paddle UP and the lower paddle LP can contact one another with parallel, flush surfaces. Alternatively, as shown in FIG. 12, the lower paddle LP can define a recessed surface with side walls for capturing the upper paddle UP therein, when the upper paddle UP is lowered into contact with the lower paddle LP.

Figure 10:
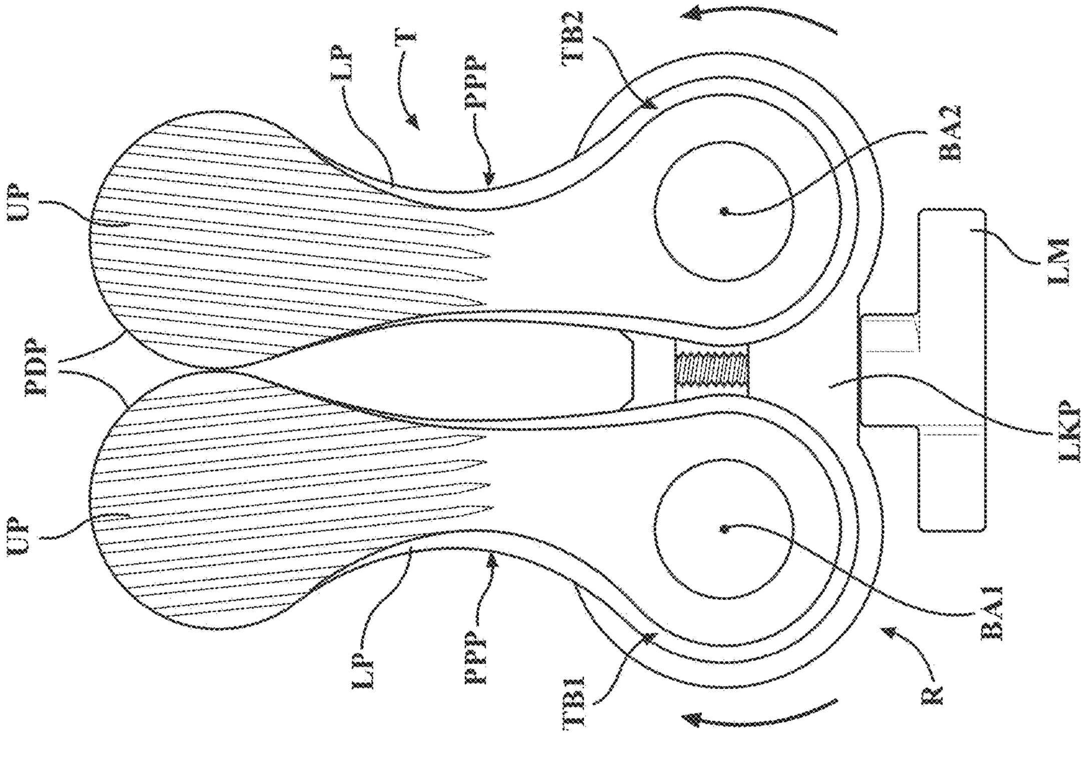
FIG. 10 is a top view of the tensor bodies being disposed within the retainer, wherein the bodies and their respective paddles are rotated in a first configuration, according to one implementation.

As shown in FIG. 4, the upper paddles UP and the lower paddles LP can each have a narrow proximal portion PPP and a distal portion PDP that is of greater surface area than the proximal portion PPP. The distal portion PDP of the upper paddle UP is configured to contact the femur F and the distal portion PDP of the lower paddle LP is configured to contact the tibia TIB. The distal portion PDP of each paddle can have a textured or rippled surface to prevent slippage between the distal portion PDP and the bone surface. The contact surface of each paddle, for example, can have one or more ridges or channels extending along the axis of the respective paddle. To facilitate quick engagement with both the left or right knee, without requiring removal of the paddles, and to avoid impingement of the patellar tendon PAT, each paddle can have an indented or concave profile in the region the proximal portion PPP. The concave profile can exhibit a smooth curve. The concave surface can be formed on one edge of each paddle, or on opposing edges of each paddle. For example, as shown in FIG. 10, the upper and lower paddles UP, LP of the first body TB1 are concave on an outer left edge of each paddle and the upper and lower paddles UP, LP of the second body TB1 are concave on an outer right edge of each paddle. In FIG. 12, on the other hand, the upper and lower paddles UP, LP of each body TB1, TB2 are symmetrically concave on both inner and outer edges of each paddle.

Additionally, by each body TB1, TB2 including a separate set of upper and lower paddles UP, LP, the footprint of the paddles can be reduced in size. For example, by including two smaller lower paddles LP, the design can eliminate a single lower paddle that has large profile with non-useful surface area. The small footprint of the paddles UP, LP can facilitate easy insertion of the tensor T into the knee joint AJ.

Advantageously, as shown in FIG. 4, the lower paddle LP can adequately contact a resected tibial surface without requiring the lower paddle LP to be invasively fastened to the resected tibial plane. The lower paddle LP does not require a keel opening for receiving a keel punch that is inserted into the tibia TIB to fix the lower paddle to the tibia TIB. The lower paddle LP maintains has sufficient length and contact surface area to contact the tibial plane without slipping. The configuration of the lower paddle LP thus enables quick evaluation of the joint AJ by eliminating additional surgical steps needed for a keel punch and eliminates unnecessary trauma to the bone from the keel punch. Eliminating a keel opening also reduces the potential of surgical debris from being captured within the keel opening, which could interfere with measurements.

4. Tensor Control System

With reference to FIG. 2, a tensor control system TCS is provided to support operation of the tensor T. The tensor control system TCS can be coupled to any one or more components of the control system 60 described above, including but not limited to, the navigation controller 36. The tensor control system TCS can include any number of one or more controllers or processors for implementing any functions described herein. The tensor control system TCS can be implemented remote from the tensor T. This remote configuration can be implemented through wireless or wired communication. For example, the tensor control system TCS can be implemented in a tensor control console TCC that is brought into the operating room, as shown in FIG. 1. The tensor control console TCC can provide wireless or wired communication to the tensor T. When wired, the cable C of the body TB1 can be attached to the control console TCC. Alternatively, the tensor control system TCS can be implemented within the navigation cart 24 or the manipulator cart 17 by attaching the cable C respectively thereto. The tensor control system TCS can be controlled through the clinical application CA and/or through user input devices TID on the tensor T itself. The tensor control system TCS can be implemented by software control modules within the tensor T or remote from the tensor T.

The tensor T can utilize, or can be utilized with, localizer 44 information derived from the tracked poses of the anatomical joint AJ, such as the poses of the femur and tibia. Optionally, the tensor T can be tracked by the navigation system 32. A tracker can optionally be coupled to the tensor T, or any moveable or static components of the tensor T, such as the paddles. In other instances, the tensor T need not be tracked.

Figure 7:
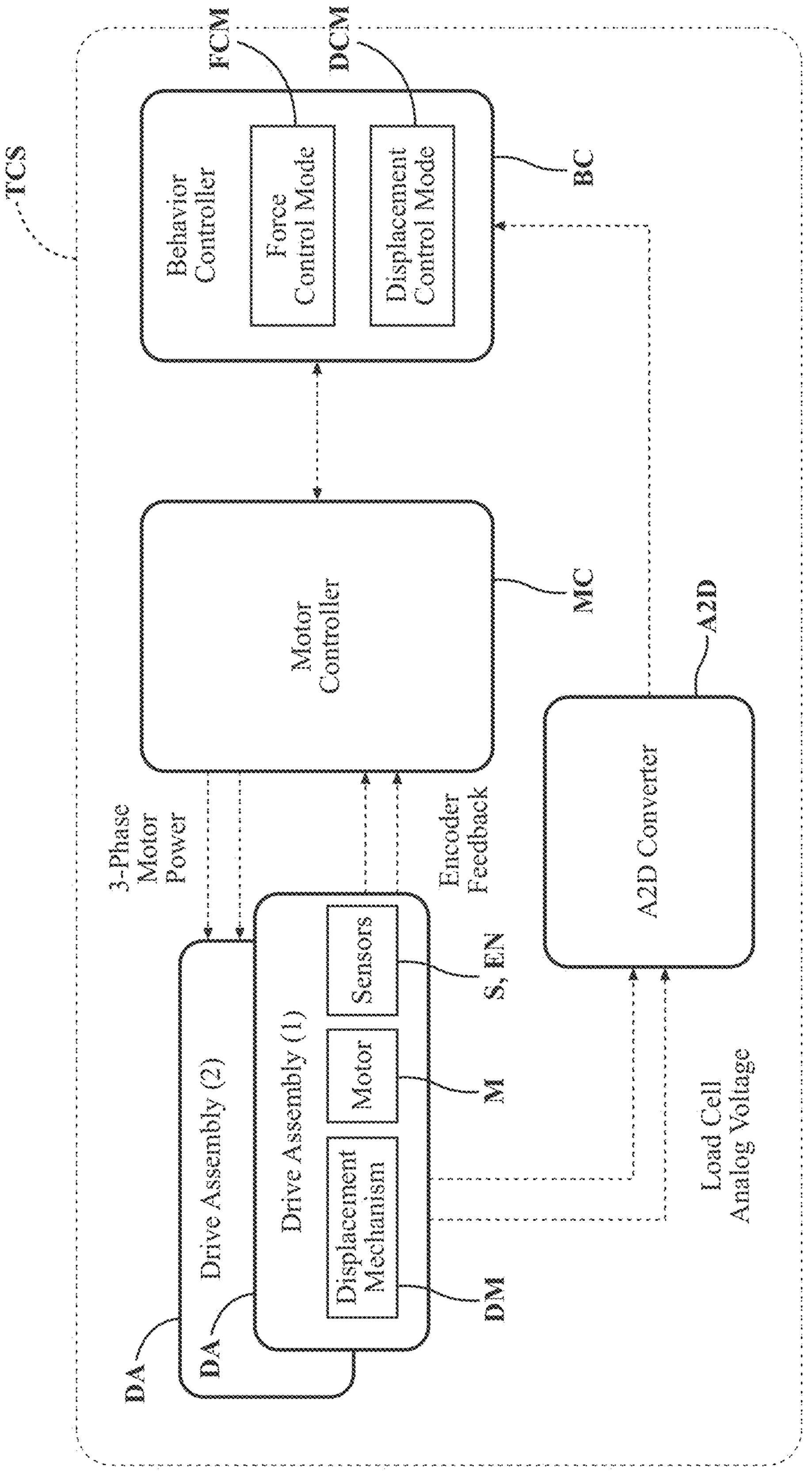
FIG. 7 is a block diagram of an example control system for controlling the tensor, according to one implementation.

FIG. 7 illustrates an example of the tensor control system TCS in greater detail. The tensor control system TCS is operatively coupled to the drive assemblies DA of the first body TB1 and the second body TB2. Any reference herein to what the first body TB1 may include is fully applicable to what the second body TB1 may include and is not repeated for simplicity. As described above, the drive assemblies DA include the displacement mechanism DM, the motor M, the sensor S, as well as the PCB and encoder EN. The tensor control system TCS can control the motor M for moving the displacement mechanism DM and obtain readings from the sensor S and the encoder EN. The tensor control system TCS can include a non-transitory computer readable medium for storing information related to the tensor T, such as sensor measurements, default settings, calibration settings, actions of the tensor, performance of the tensor, error signals, and the like.

The tensor control system TCS includes one or more motor controllers MC coupled to the drive assembly DA for executing a commanded action (position or force) for the drive assembly DA, and ultimately the upper paddle UP. The motor controller MC can control power to the drive assembly DA and its respective components. For example, the motor controller MC can provide 3-phase motor power to the motor M. The motor controller MC can be implemented on the PCB of each body TB1, TB2, or implemented remote from each body TB1, TB2. When implemented in the tensor T, each body TB1, TB2 can include its own dedicated motor controller MC. When implemented remote from the tensor T, one motor controller MC can be utilized to control both drive assemblies DA. The motor controller MC can receive feedback from the drive assembly DA, including feedback from the encoder EN, sensor S, or motor M. The motor controller MC can control the motor M based on the feedback signals. The feedback signals can relate to position, velocity, acceleration, force, commutation, gain, or any other parameters experienced by, or exhibited by any component of the drive assembly DA. In one version, the motor controller MC regulates the motor M and continually adjusts the torque that motor M outputs to, as closely as possible, ensure that the motor M drives the displacement mechanism DM to the commanded position or force. In some examples, the motor controller MC is proportional integral derivative (PID) controllers. Other types of controllers are contemplated.

The tensor control system TCS includes one or more behavior controllers BC. The behavior controller BC is coupled to the motor controller MC and provides commands to the motor controller MC. For example, the behavior controller BC can command the motor controller MC to move the upper paddle UP to a commanded position or until a force applied to the upper paddle UP is reached. Output from the sensor S or encoder EN can be utilized by the behavior controller BC when commanding the motor controller MC. For example, as shown in FIG. 7, analog voltage signals from the sensor S can be converted to digital signals using an analog to digital converter A2D coupled between the drive assembly DA and the behavior controller BC. The behavior controller BC can couple to the A2D using any type of communication technique, such as by using USB. The behavior controller BC can be implemented on the PCB of each body TB1, TB2, or implemented remote from each body TB1, TB2. When implemented in the tensor T, each body TB1, TB2 can include its own dedicated behavior controller BC. When implemented remote from the tensor T, one behavior controller BC can be shared among the bodies TB1, TB2. The behavior controller BC can receive control input from the clinical application CA and/or through user input TID devices on the tensor T itself. In one example, the behavior controller BC is a hard real-time operating system (RTOS) microkernel. The behavior controller BC can couple to the motor controller MC using any type of communication technique, such as by using Ethernet or EtherCat. Other types of controllers are contemplated.

4A. Force Control Mode

As shown in FIG. 7, the tensor control system TCS, through the behavior controller BC and motor controller MC, is configured to control the tensor T in a force control mode FCM. In the force control mode FCM, the drive assembly DA is commanded to move the displacement mechanism DM (and hence, the upper paddle UP) until a force is reached. The force can be sensed in many ways. In one example, the force is sensed by the sensor S. Additionally or alternatively, the force can be measured using electrical motor current, strain gauges, load cells, or the like. The sensed force can be applied to the upper paddle UP. For instance, the drive assembly DA may be commanded to move the displacement mechanism DM axially upwards to move the upper paddle UP upwards until a force of X Newtons (applied to the upper paddle UP) is detected by the sensor S. The force can be any value, such as up to 400N, or greater. The force control mode FCM can be the primary mode utilized for tensioning the anatomical joint AJ. Once the force is detected, the drive assembly DA may be commanded to stop or retract movement of the upper paddle UP. The force control mode FCM can be understood as a closed-loop or open-loop control scheme that uses feedback from the sensor S to reach or maintain the desired set point of the tensor T. The force can be a positive force applied downward on the upper paddle UP, or a negative force applied upward on the upper paddle UP. The force can be a discrete force or a range of forces. The force can be sensed continuously or intermittently. The force to be detected can be a predetermined force and can be stored in memory. For instance, the force can be a predetermined joint balancing force, a force based on a surgeon preference, a force obtained from statistical data, or a force previously recorded from actions of the tensor T. The force control mode FCM can be triggered or configured through the clinical application CA and/or through user input TID devices on the tensor T itself. For example, the user can input preferred threshold forces for the force control mode FCM. Each body TB1, TB2 of the tensor T can be selectively and independently operated in the force control mode FCM. Further uses of the force control mode FCM will be described below. For any aspect of force control mode, it is contemplated that the tensor control system TCS can monitor displacement of the tensor T. For instance, the tensor control system TCS can monitor the displacement of the tensor T as the force increases, or once the desired force is reached.

4B. Displacement Control Mode

As shown in FIG. 7, the tensor control system TCS, through the behavior controller BC and motor controller MC, is further configured to control the tensor T in a displacement control mode DCM. In the displacement control mode DCM, the drive assembly DA is commanded to move the displacement mechanism DM (and hence, the upper paddle UP) until a position/displacement of the upper paddle UP is reached. The displacement control mode DCM can be understood as the tensor T behaving as a spacer or tibial trail. Position and displacement can be interchangeable or equivalent in this control mode. In other words, this mode can alternatively be referred to as a position control mode. The position/displacement can be measured using any suitable means, such as using the encoder EN feedback or other parameters of the motor M. The position/displacement can also be measured using measurements from the navigation system. For example, tracking markers can be coupled to the tensor T, or paddles, and the localizer can detect the pose of the tracking markers to determine the position/displacement of the tensor T. The position of the paddle UP is the location of the paddle UP at a given time. The position can be a discrete position or a range of positions. Displacement of the paddle UP can be understood as the change in position of the upper paddle UP relative to a reference point, such as relative to the lower paddle LP. The displacement can be a discrete displacement or a range of displacements. The zero-displacement baseline condition may be set as the tensor T being in a closed position whereby the upper paddle UP is contacting the lower paddle LP. In one example, the drive assembly DA may be commanded to move the displacement mechanism DM axially upwards to move the upper paddle UP upwards until the upper paddle UP has been displaced relative to the lower paddle LP by X mm. The displacement can be any range, e.g., between 0-30 mm or 6-24 mm. Once the commanded position or displacement is obtained, the drive assembly DA may be commanded to stop or retract movement of the upper paddle UP. The displacement control mode DCM can be understood as an open-loop or closed-loop control scheme in which the outputted position/displacement of the paddle UP depends on the inputted commanded position/displacement, but not vice-versa. The position/displacement can be a positive position/displacement causing axial upward movement of the upper paddle UP, or a negative position/displacement causing axial downward movement of the upper paddle UP. The position/displacement can be predetermined be stored in memory. For instance, the position/displacement can be a predetermined joint balancing position/displacement, a position/displacement based on a surgeon preference, a position/displacement obtained from statistical data, or a position/displacement previously recorded from actions of the tensor T. The displacement control mode DCM can be triggered or configured through the clinical application CA and/or through user input TID devices on the tensor T itself. For example, the user can input preferred threshold position/displacement for the displacement control mode DCM. Each body TB1, TB2 of the tensor T can be selectively and independently operated in the displacement control mode DCM. Additionally, the tensor control system TCS can independently control each body TB1, TB2 to switch operation between the force control mode FCM and the displacement control mode DCM, or vice versa. For any aspect of displacement control mode, it is contemplated that the tensor control system TCS can monitor force of the tensor T. For instance, the tensor control system TCS can monitor the force applied to the tensor until, or when, the commanded displacement is reached. Further uses of the displacement control mode DCM will be described below.

4C. Force-Displacement Control Mode

It is contemplated that aspects of the force control mode FCM and the displacement control mode DCM can be simultaneously implemented or combined in a single mode, i.e., a force-displacement control mode. In one implementation, in the force-displacement control mode, the drive assembly DA is commanded to move the upper paddle UP according to a predetermined position/displacement until a predetermined force sensed by the sensor S is reached. In another implementation, in the force/displacement control mode, the drive assembly DA is commanded to move the upper paddle UP to apply a predetermined force until to a predetermined position/displacement is reached. Hence, in the force-displacement control mode, force and displacement can be commanded until one, or both, of the commanded force or displacement is reached. Any of the above aspects and implementations of the force control mode FCM and the displacement control mode DCM can be equally applied to the force-displacement control mode.

5. Tensor Body Adjustability

The tensor T can comprise one of many configurations to facilitate unique adjustability of the first and second bodies TB1, TB2. As will be understood from the following description, the adjustability of the tensor T enables the tensor T to accommodate various sized bones of any knee joint. The first and second bodies TB1, TB2 can be uniquely adjusted to enable quick evaluation of both the left knee or the right knee without requiring replacement of paddles or reconfiguration. Adjustability of the bodies TB1, TB2 further reduces the likelihood of slippage of the tensor T from the joint AJ and reduces the likelihood of impingement with the patellar tendon PAT.

5A. Tensor Body Retainer

Figure 9:
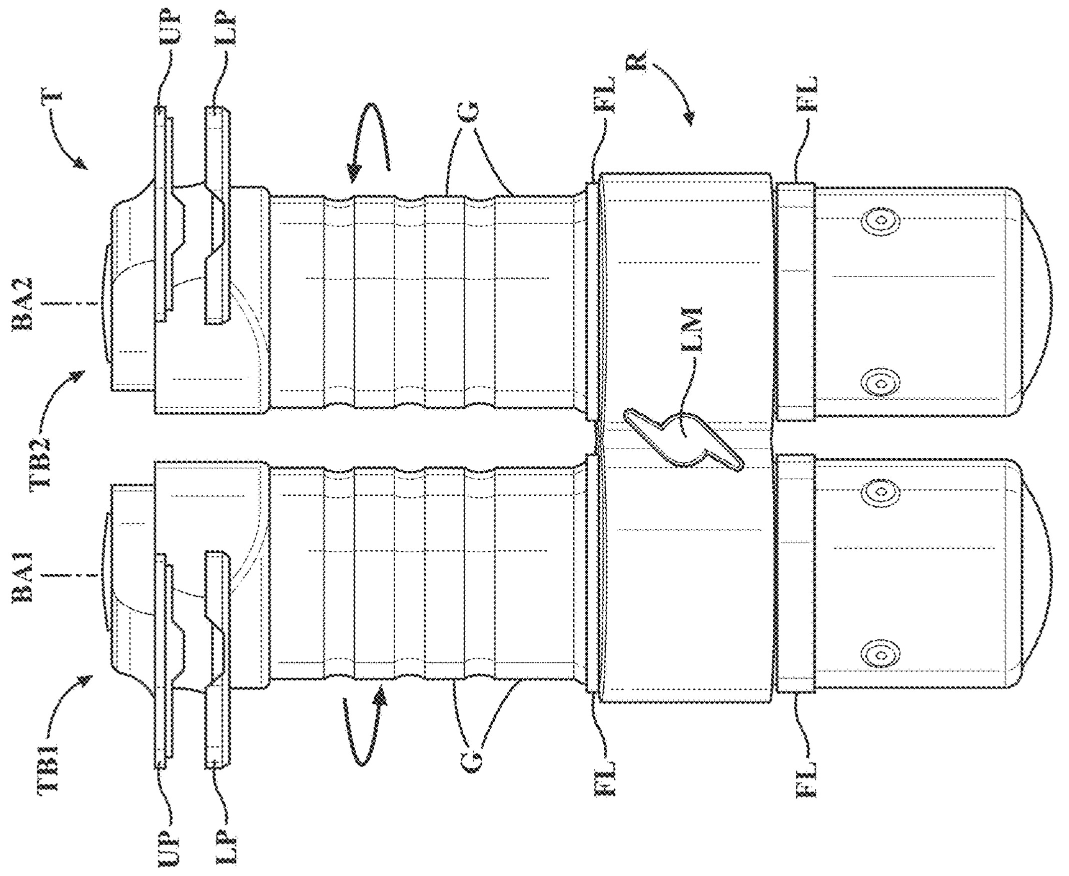
FIG. 9 is a perspective view of the two bodies of the tensor being installed into the retainer and configured to rotate within the retainer, according to one implementation.
Figure 8:
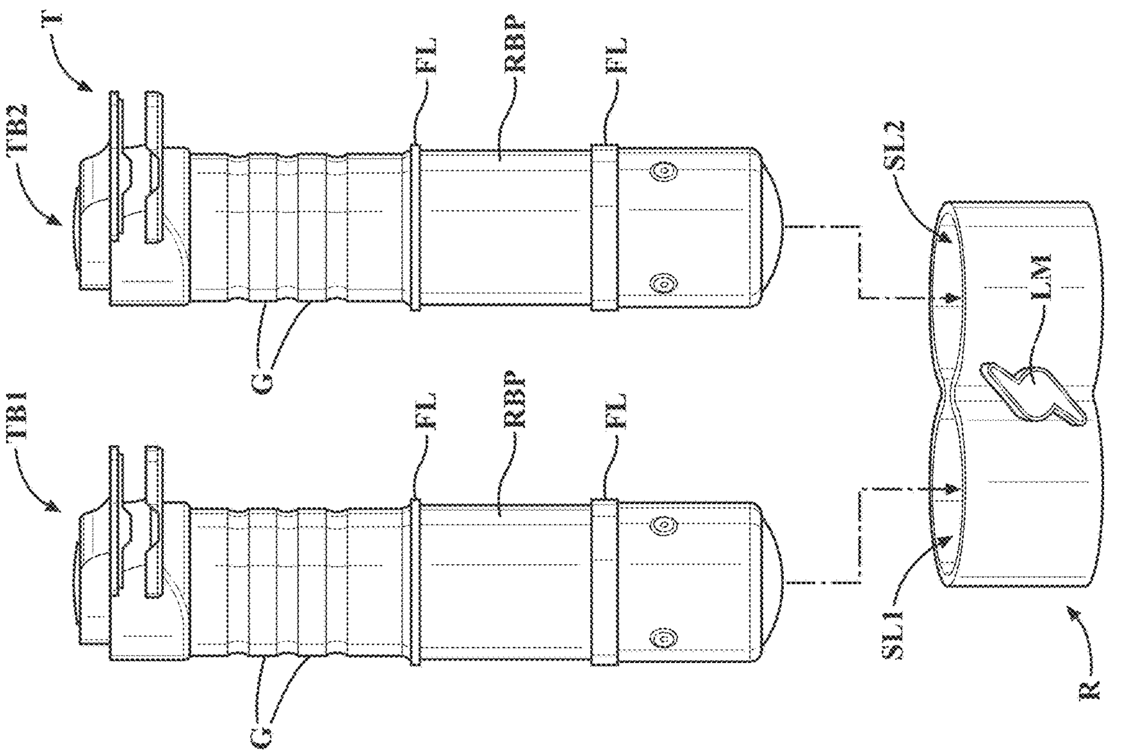
FIG. 8 is a perspective assembly view of two bodies of the tensor being insertable within a retainer, according to one implementation.

With reference to FIGS. 3-6 and 8-22, the tensor T comprises a retainer R that is configured to hold or couple the first body TB1 and the second body TB2 relative to one another. The retainer R is a component that is separable from the first and second bodies TB1, TB2. As shown in FIG. 8, the first and second bodies TB1, TB2 are inserted into the retainer R. The retainer R captures the bodies TB1, TB2. As shown in FIG. 9, after insertion, the first body TB1 is configured to rotate within the retainer R to enable rotational adjustment of the set of paddles UP, LP of the first body TB1. Similarly, the second body TB2 is configured to rotate within the retainer R to enable rotational adjustment of the set of paddles UP, LP of the second body TB2. A locking mechanism LM is coupled to the retainer R and is configured to be actuated to rotationally lock one, or both, of the first body TB1 and the second body TB2 relative to the retainer R. In other words, once the locking mechanism LM is actuated, the first and/or second bodies TB1, TB2 are prevented from rotating about their respective body axis BA1, BA2 (i.e., an axis longitudinally defined in along the direction of movement of the displacement mechanism DM, or upper paddle UP). When not rotationally locked by the locking mechanism LM, the bodies TB1, TB2 can freely rotate 360 degrees within the retainer R. With the retainer R, the paddles of the first and second bodies TB1, TB2, advantageously can be positioned in an infinite number of configurations. This allows fine-tuned rotational adjustment of the paddles UP, LP that can be customized for the specific anatomy of the patient. Once the desired orientation of the bodies TB1, TB2 is identified, the user can actuate the locking mechanism LM to fix the desired orientation.

The retainer R can facilitate quick release the bodies TB1, TB2 such that the bodies TB1, TB2 can be removed from the retainer R and separated from one another. This can be done by releasing the locking mechanism LM from a locked state into a released state. Advantageously, removing the bodies TB1, TB2 from the retainer R can facilitate case in cleaning or sterilization of the bodies TB1, TB2 and retainer R.

As shown throughout FIGS. 8-22, the retainer R can define a first sleeve SL1 configured to receive the first body TB1, and a second sleeve SL2 configured to receive the second body TB2 of the tensor T. The retainer R enables the first body TB1 to rotate within the first sleeve SL1 to enable rotational adjustment of the paddles of the first body TB1 and enables the second body TB2 to rotate within the second sleeve SL2 to enable rotational adjustment of the paddles of the second body TB2. Each of the first sleeve SL1 and the second sleeve SL2 can include a size, opening, width, length, or a diameter that is adjustable. The locking mechanism LM can be actuated to simultaneously decrease the size, opening, width, length, or a diameter of each of the first and second sleeves SL1, SL2 to rotationally lock the first body TB1 and the second body TB2 relative to the retainer R.

As shown in FIG. 8, the first sleeve SL1 and second sleeve SL2 each can have an opening configuration to hold a correspondingly shaped retainer body portion RBP formed on the outer surface of the first body TB1 and the second body TB2, respectively. The sleeves SL1, SL2 can have any opening shape (such as circular, oval, rectangular, polygonal, etc.) to conform to the correspondingly shaped retainer body portion RBP of the first and second bodies TB1, TB2. The retainer body portion RBP of the first body and the second body TB1, TB2 can each have a circumferential, annular, or perimeter-based feature that can respectively engage the first sleeve SL1 and the second sleeve SL2 to axially constrain the first body TB1 and second body TB2 relative to the retainer R. For example, as shown in FIGS. 8 and 9, the retainer body portion RBP of the first and second bodies TB1, TB2 include a perimeter flange FL that is wider than the opening of each respective sleeve SL1, SL2. The flange FL acts as a hard stop to prevent each sleeve SL1, SL2 from being sliding beyond the flange FL. The flange FL constrains the respective sleeve SL in one direction relative to the body axis BA. Alternatively, each retainer body portion RBP can include an upper flange and a lower flange wherein the distance between the upper flange and lower flange is sized to fit the sleeve SL. The upper and lower flanges can constrain the respective sleeve SL in two directions relative to the body axis BA. Alternatively, or additionally, each retainer body portion RBP can define a recessed surface around the perimeter of the respective body TB1, TB2 to capture the respective sleeve SL. This way, once the respective sleeve SL is captured around the respective body TB1, TB2, the sleeve SL can be flush with the remaining surface of the body TB1, TB2.

To facilitate ergonomic rotation within the retainer R, each body TB1, TB2 can have gripping features G located on a surface of the body. For example, as shown in FIG. 8, the gripping features can be ridges or channels formed around the respective body TB1, TB2. The user can grasp the respective body TB1, TB2 in the region comprising the gripping features G to facilitate rotation of the respective body TB1, TB2.

FIGS. 10 and 11 illustrate how the bodies TB1, TB2 can be rotated using the retainer R. Here, the retainer R holds the bodies TB1, TB2 in a fixed lateral direction such that the spacing between the body axes BA1, BA2 is fixed. In FIG. 10, the first body TB1 is rotated clockwise about the body axis BA and the second body TB1 is rotated counterclockwise about the body axis BA. The distal portions PDP of the paddles UP, LP are moved in close proximity to each other and can touch one another. This adjustment may enable the tensor paddles to be inserted into and fit a smaller sized knee joint. In FIG. 11, the first body TB1 is rotated counterclockwise about the body axis BA1 and the second body TB1 is rotated clockwise about the body axis BA2. This causes the distal portions PDP of the paddles UP, LP to be moved further away from other. This adjustment may enable the tensor paddles to be inserted into and fit a larger sized knee joint.

Figure 13:
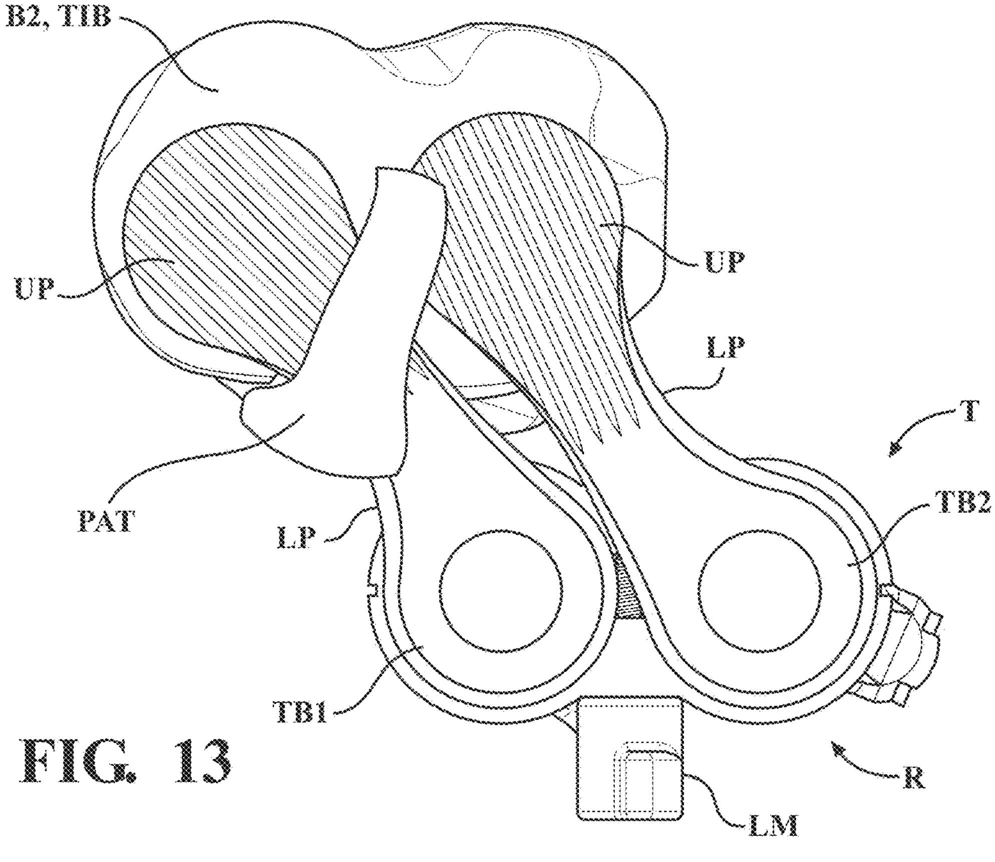
FIG. 13 is a top view of the tensor bodies and their respective paddles being disposed on a resected tibia of a left knee and rotated in a second configuration to enable a separate set of paddles to circumvent the patellar tendon, according to one implementation.

FIGS. 12 and 13 illustrate the practical implementation of the tensor T adjustability using the retainer R. In FIG. 12, the tensor T is inserted into a right knee and the bodies TB1, TB2 are both rotated clockwise within the retainer R such that the paddles UP, LP of the second body TB2 circumvent the patellar tendon PAT. The lower paddles LP of each respective body TB1, TB2 sufficiently contact the resected tibial plane (for a pre-resection workflow). Advantageously, the bodies TB1, TB2 can be rotated even while inserted into the knee joint. Once the surgeon rotates the bodies TB1, TB2 into the desired orientation, the surgeon can actuate the locking mechanism LM to fix the desired orientation of the paddles. Of course, if desired, the bodies TB1, TB2 can be rotated before inserting the tensor T into the knee joint. In FIG. 13, during the evaluation process (for the same patient), the locking mechanism LM is released to enable rotation of the bodies TB1, TB2 and the tensor T is inserted into a left knee. The bodies TB1, TB2 are both rotated counterclockwise within the retainer R such that the paddles UP, LP of the first body TB1 circumvent the patellar tendon PAT. FIGS. 12 and 13 further illustrate the beneficial ability of the tensor T to be used with right and left knees without requiring any changing of parts or time-consuming reconfiguration of the tensor T.

Referring to FIGS. 14-26, additional configurations of the retainer R and locking mechanism LM will now be described. The bodies TB1, TB2 of the tensor T are not illustrated in these figures for simplicity in illustration. For any of the configurations shown and described, it is understood that the bodies TB1, TB2 are designed to be inserted into the retainer R and rotationally locked by the locking mechanism LM.

Figure 15:
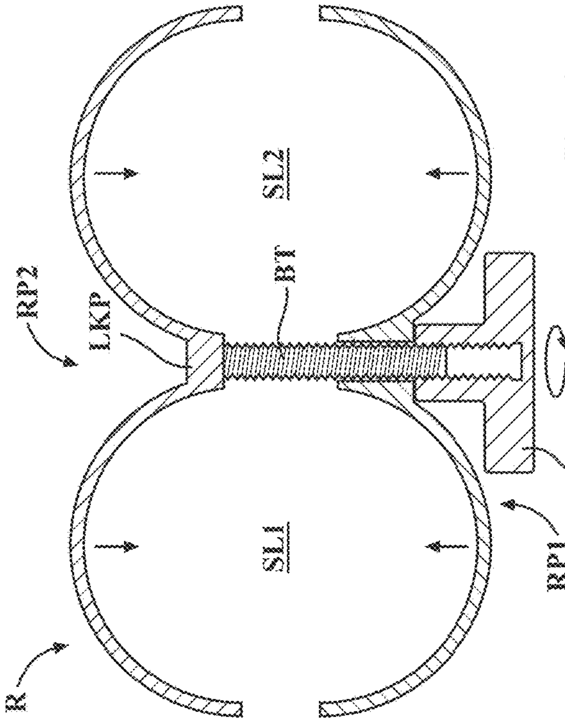
FIG. 15 is a top diagrammatic view of the retainer of FIG. 14 showing the retainer portions being separated in an open state and illustrating actuation of the locking mechanism to bring the retainer portions closer together, according to one implementation.
Figure 16:
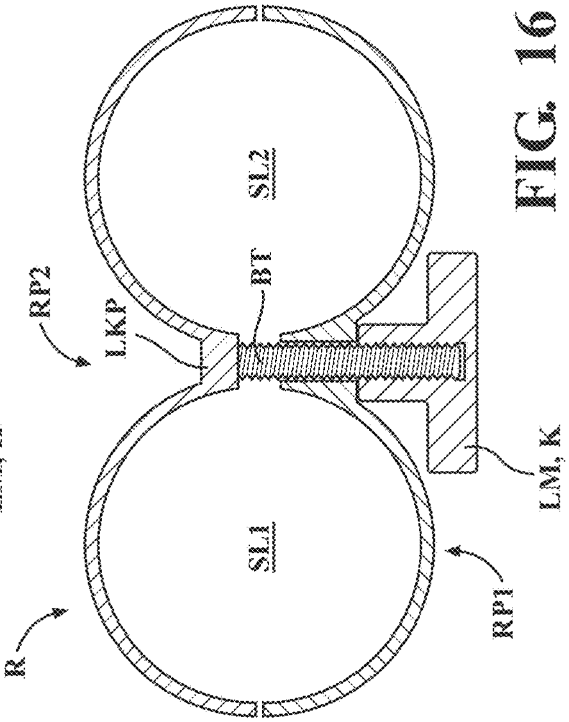
FIG. 16 is a top diagrammatic view of the retainer of FIG. 14 showing the retainer portions being placed in a closed state by the locking mechanism, according to one implementation.
Figure 14:
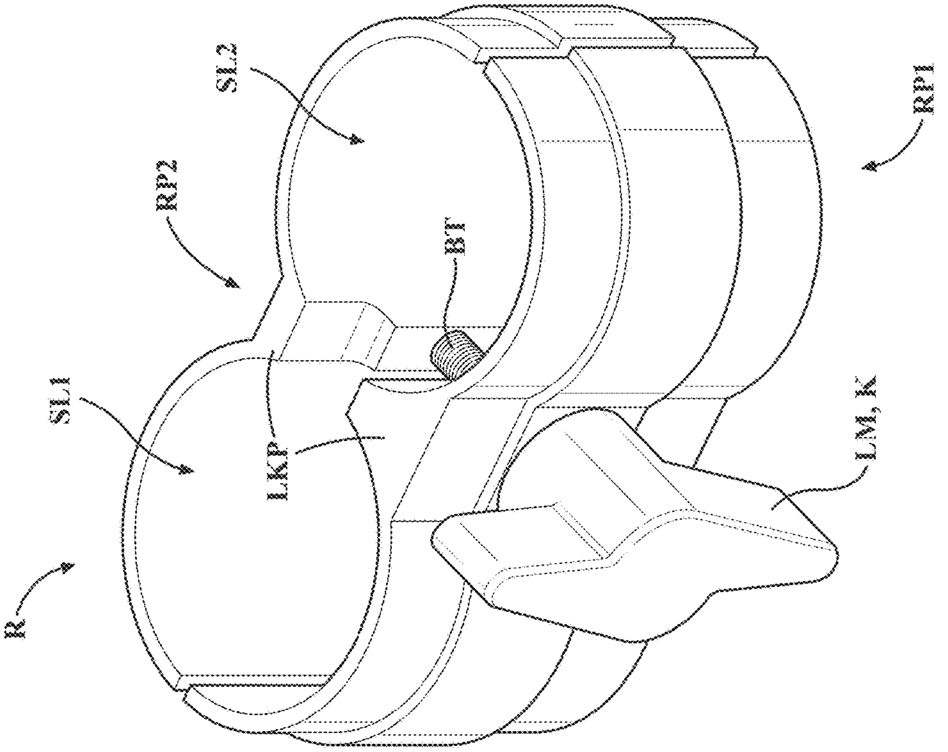
FIG. 14 is a perspective view of one configuration of the retainer for the tensor bodies, which includes according to one implementation, a locking mechanism comprising a knob and separable retainer portions.

With reference to FIGS. 14-16, one example is illustrated wherein the retainer R comprises dual sleeves SL1, SL2. The retainer R can be split into a first portion RP1 and a second portion RP2. Each of the first and second portions RP1, RP2 can partially define the first and second sleeves SL1, SL2. For example, when the sleeves have a circular or cylindrical shape, the first and second portions RP1, RP2 can partially define a half circle or half cylinder part of first and second sleeves SL1, SL2. Portions of the sleeves SL1, SL2 are laterally fixed relative to one another by a rigid link portion LKP coupled between the sleeve portions. The locking mechanism LM can be operatively coupled to the first and second portions RP1, RP2. As shown in FIG. 15, the locking mechanism LM can be actuated to simultaneously bring the first and second portions RP1, RP2 of the retainer R closer together. Although not shown for simplicity, the bodies TB1, TB2 can be inserted into the retainer R prior to this step of bringing the first and second portions RP1, RP2 together. As shown in FIG. 16, the locking mechanism LM can continue to be actuated until the first and second portions RP1, RP2 of the retainer R apply sufficient constraining force against the retainer body portions RBP of the bodies TB1, TB2 to rotationally lock the bodies TB1, TB2 relative to the retainer R. The constraining force can be radial (towards the body axis BA) and/or transverse to the body axis BA. The user can know that the bodies TB1, TB2 are retained when the locking mechanism LM can no longer be easily actuated. When rotationally locked, the first and second portions RP1, RP2 can remain slightly spaced from each other (as shown in FIG. 16) or the first and second portions RP1, RP2 may contact one another. To release the bodies TB1, TB2, the locking mechanism LM is rotated in the opposite direction to reopen the first and second portions RP1, RP2 (as shown in FIG. 15). The spacing between the first and second portions RP1, RP2 will enable sufficient clearance for the bodies TB1, TB2 to be removed from the retainer R.

In the example of FIGS. 14-16, the locking mechanism LM comprises at least one knob K accessible to the user from an external surface of the retainer R. The knob K can be coupled to a bolt BT that extends through the retainer R, and more specifically, through an opening formed in the first portion RP1. The bolt BT is fixed at the distal end to the second portion RP2. The knob K comprises a threaded opening inside the knob K for threadably engaging a proximal end of the bolt BT. As the knob K is rotated in a first direction, the knob K can move along the bolt BT towards the second portion RP2. The end of the knob K can press against a surface of the first portion RP1 to gradually slide the first portion RP1 along the bolt B. This causes the first portion RP1 to move towards the second portion RP2. As the knob K is rotated in a second (opposite) direction, the knob K can move along the bolt BT in a direction away from the second portion RP2. The knob K will create clearance for the first portion RP1 to slide along the bolt BT away from the second portion RP2 to rotationally release the bodies TB1, TB2. When retainer R is closed, the knob K and bolt BT do not interfere with the sleeve openings or rotation of the bodies TB1, TB2 with the sleeves SL. One configuration of the knob K and bolt B are shown. However, other configurations are possible.

Figure 17:
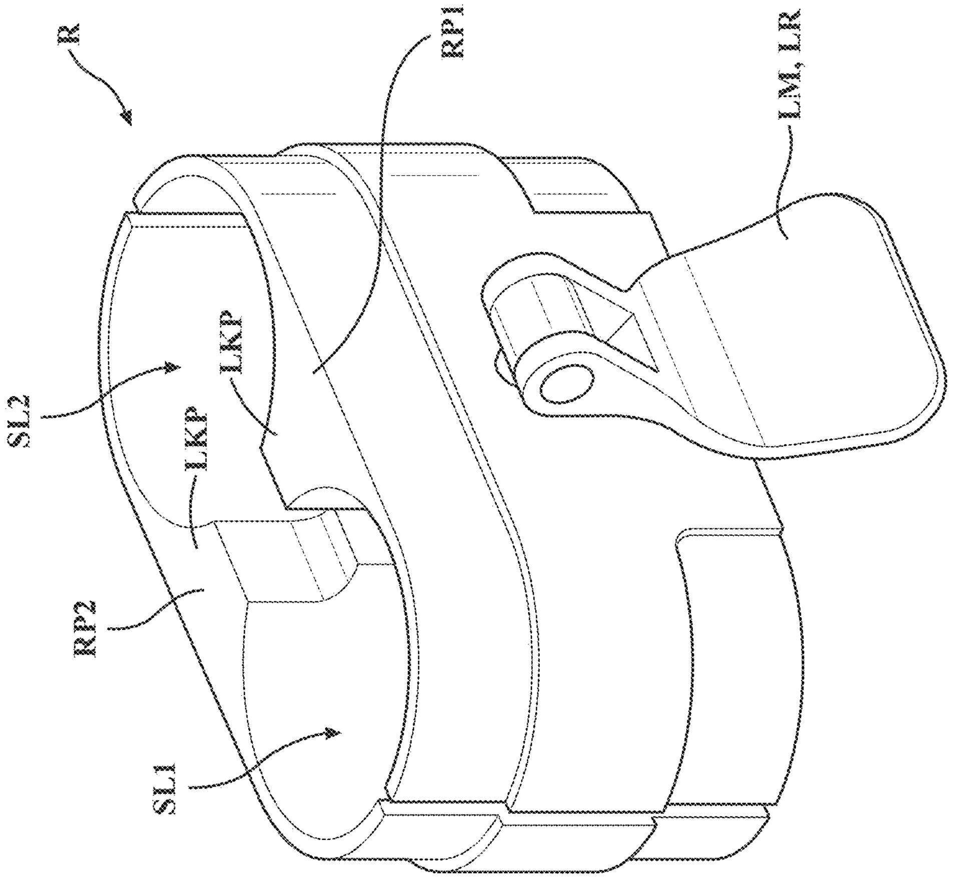
FIG. 17 is a perspective view of another configuration of the retainer for the tensor bodies, which includes according to one implementation, a locking mechanism comprising a lever and separable retainer portions.
Figure 18:
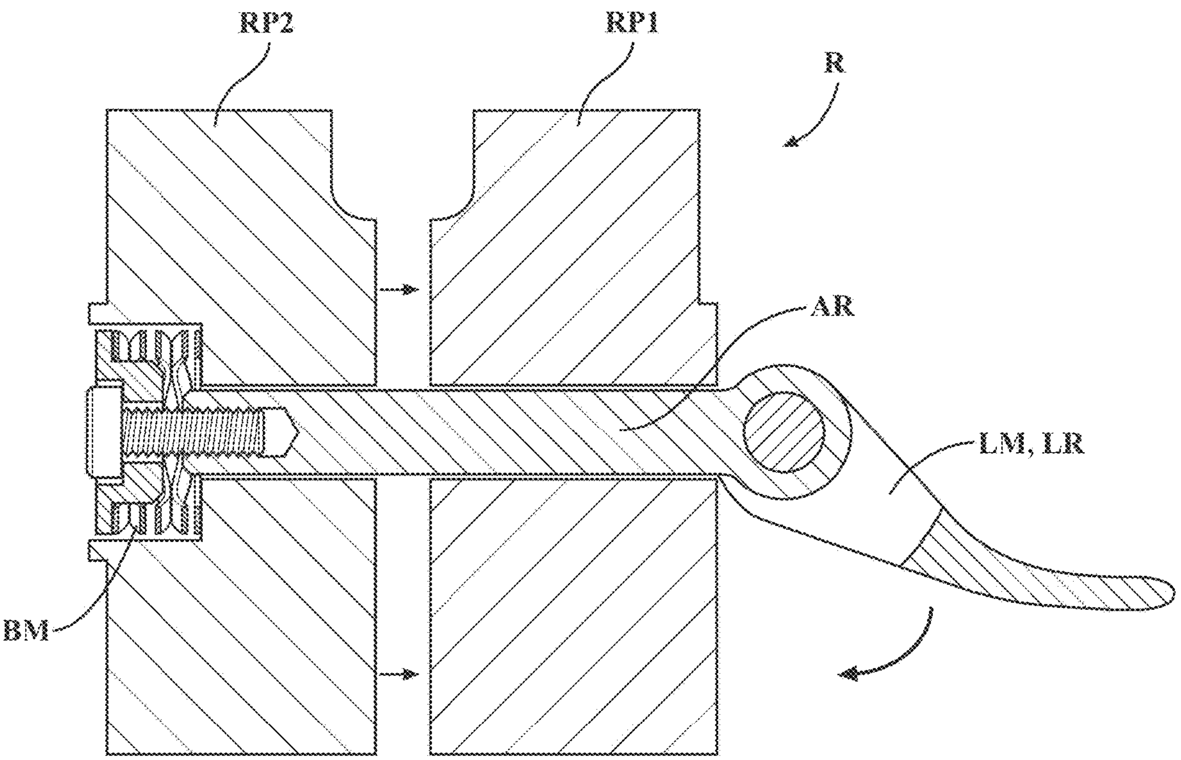
FIG. 18 is a side diagrammatic view of the retainer of FIG. 17 showing the retainer portions being separated in an open state and illustrating actuation of the locking mechanism to bring the retainer portions closer together, according to one implementation.
Figure 19:
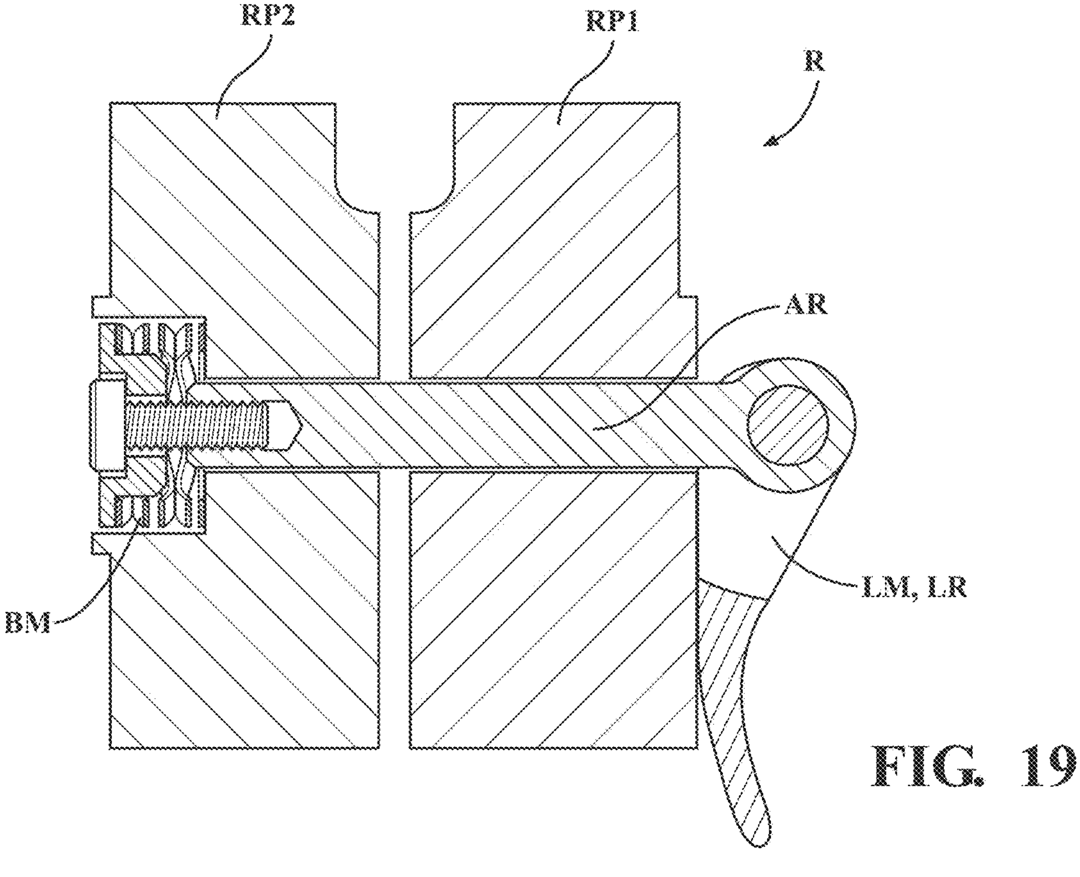
FIG. 19 is a side diagrammatic view of the retainer of FIG. 17 showing the retainer portions being placed in a closed state by the locking mechanism, according to one implementation.

In the example of FIGS. 17-19, another example is illustrated which includes the retainer R split into first and second portions RP1, RP2. Here, the locking mechanism LM comprises at least one lever LR accessible to the user from an external surface of the retainer R. FIGS. 18 and 19 illustrate the retainer R and locking mechanism LM from a side view. The lever LR can be coupled to an arm AR that extends through the retainer R, and more specifically, through an opening formed in the first portion RP1. The arm AR is coupled at the distal end to the second portion RP2, for example using a fastener. A biasing mechanism BM can be coupled to the second portion RP and the biasing mechanism BM can interface with a distal end of the arm AR. The biasing mechanism BM can be a coil spring or a Belleville spring, for example. The lever LR is eccentrically rotatable about a hinge. As shown in FIG. 18, as the lever LR is rotated in a first direction (e.g., pulled down), the lever LR pulls the arm AR in a first lateral direction that causes the second portion RP2 to move towards the first portion RP1. In FIG. 19, the lever LR is in the fully closed position and the second portion RP2 is moved to close the retainer R and capture the bodies TB1, TB2 (when inserted). When the bodies TB1, TB2 are inserted in the retainer R and the lever LR is in the fully closed position (FIG. 19), the biasing mechanism BM can be extended to move the second portion RP2 slightly away from the first portion RP1. The biasing mechanism BM is extended due to the counterforce of the bodies TB1, TB2 acting on the second portion RP2. In turn, the biasing mechanism BM regulates the forces acting the bodies TB1, TB2 to ensure the bodies TB1, TB2 are sufficiently captured by the retainer R while preventing damage to the bodies TB1, TB2 or the retainer R. The biasing mechanism BM can also function as a preload to ensure the lever LR applies the appropriate tension for constraining the bodies TB1, TB2 within the retainer R. To release the bodies TB1, TB2, the lever LR can be rotated in a second direction (e.g., pulled up). As a result, the lever LR pushes the arm AR in a second (opposite) lateral direction that pushes the second portion RP2 away from the first portion RP1 to open the retainer R.

Figure 20:
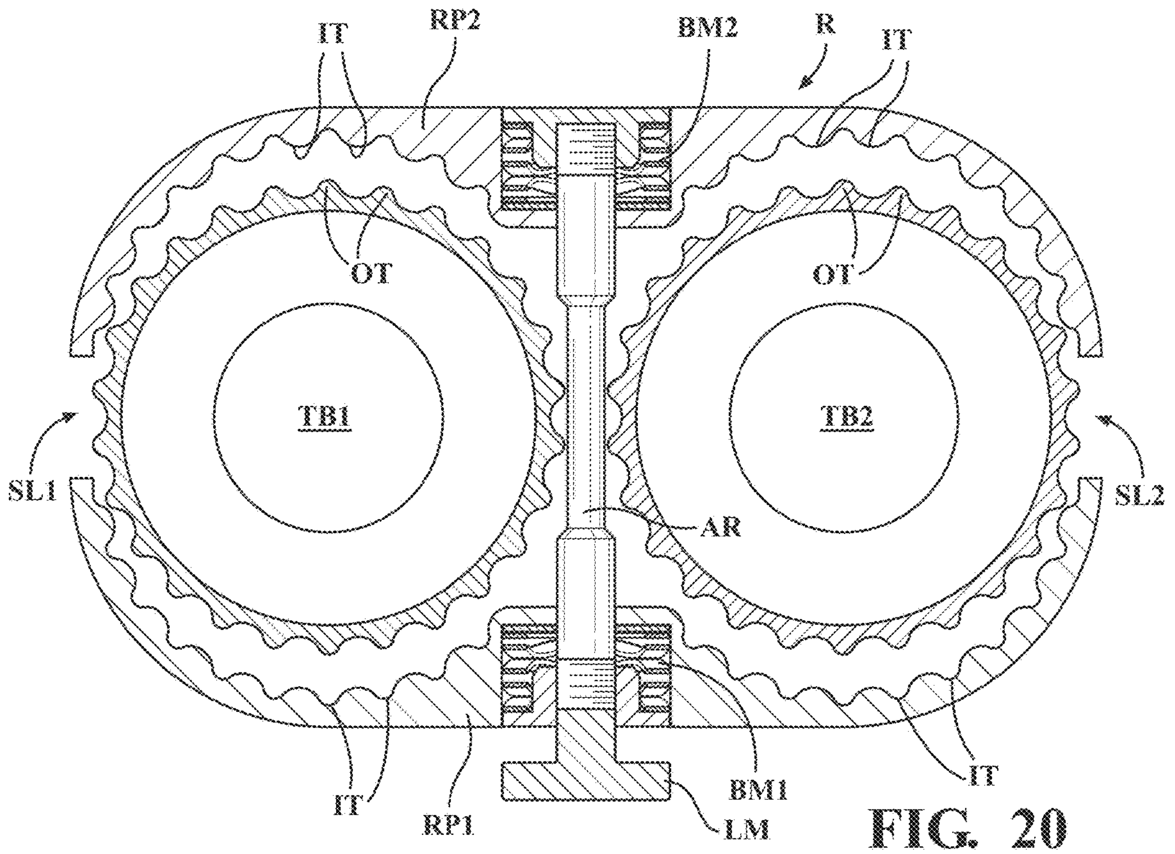
FIG. 20 is a top diagrammatic view showing a configuration of the retainer disposed around the tensor bodies, wherein the retainer portions are separated in an open state and the retainer portions and the tensor bodies comprise corresponding teeth for engaging one another, according to one implementation.
Figure 21:
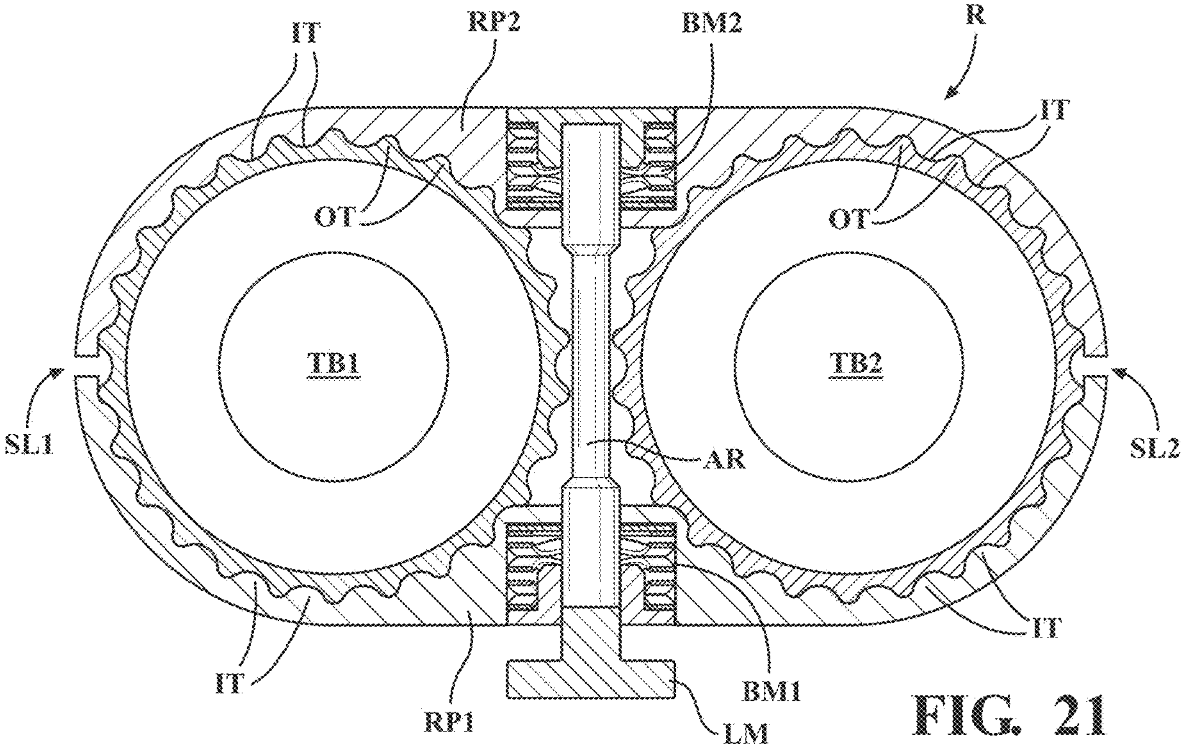
FIG. 21 is a top diagrammatic view of the configuration of FIG. 20 showing the retainer portions being placed in a closed state by the locking mechanism and the corresponding teeth engaging one another to rotationally lock the tensor bodies to the retainer, according to one implementation.

FIGS. 20 and 21 illustrate yet another example of the retainer R and locking mechanism LM. In this example, the retainer R is once again split into first and second portions RP1, RP2. The first portion RP1 and the second portion RP2 each define inner teeth IT defined in the respective sleeve portions. The first and second bodies TB1, TB2 are shown within the retainer R and are modified to include outer teeth OT which are formed on an external surface of each body TB1, TB2. The inner teeth IT and outer teeth are formed with complementary shapes and sizes so that the teeth IT, OT can easily engage one another. Any number of teeth IT, OT can be provided beyond the number of teeth IT, OT shown. Increasing the number of teeth IT, OT will increase the number of discrete rotational positions in which the bodies TB1, TB2 can be locked. In this example, the locking mechanism LM includes an arm AR coupled between the first and second portions RP1, RP2. A first biasing mechanism BM1 is located on the first portion RP1 and a second biasing mechanism BM2 is located on the second portion RP2. The arm AR is coupled between the biasing mechanism BM1, BM2. The locking mechanism LM can include any example user interface (such as the knob K, lever L, push button, etc.) for actuating the locking and unlocking of the portions RP1, RP2. In FIG. 20, the portions RP1, RP2 are in an open state and the bodies TB1, TB2 can freely rotate within the retainer R because the teeth IT, OT are not yet engaged. In FIG. 20, the locking mechanism LM is actuated causing the one, or both of the portions RP1, RP2 to move closer together into a closed state whereby the teeth IT, OT fully engage to rotationally and simultaneously lock the bodies TB1, TB2 relative to the retainer R. In this example, a lever LR could be placed on one portion, or on both portions RP1, RP2. The biasing mechanisms BM1, BM2 perform the same beneficial functions as described in the preceding example. In this example, it is contemplated to use only one biasing mechanism BM instead of two biasing mechanisms BM1, BM2.

In another example, the locking mechanism LM can include a button that can be coupled to a mechanical or electromechanical system for facilitating locking of the retainer R. For example, the retainer R could comprise a motor that is coupled to a lead screw that is coupled between the portions RP1, RP2 (like that shown in FIGS. 15 and 16). The button sends a signal to a motor controller to cause the motor to drive the lead screw in a first direction to move portions RP1, RP2 closer together to close the retainer R. The same button (or another button) can send another signal to the motor controller to cause the motor to drive the lead screw in an opposite direction to move portions RP1, RP2 away from each other to open the retainer R.

Figure 22:
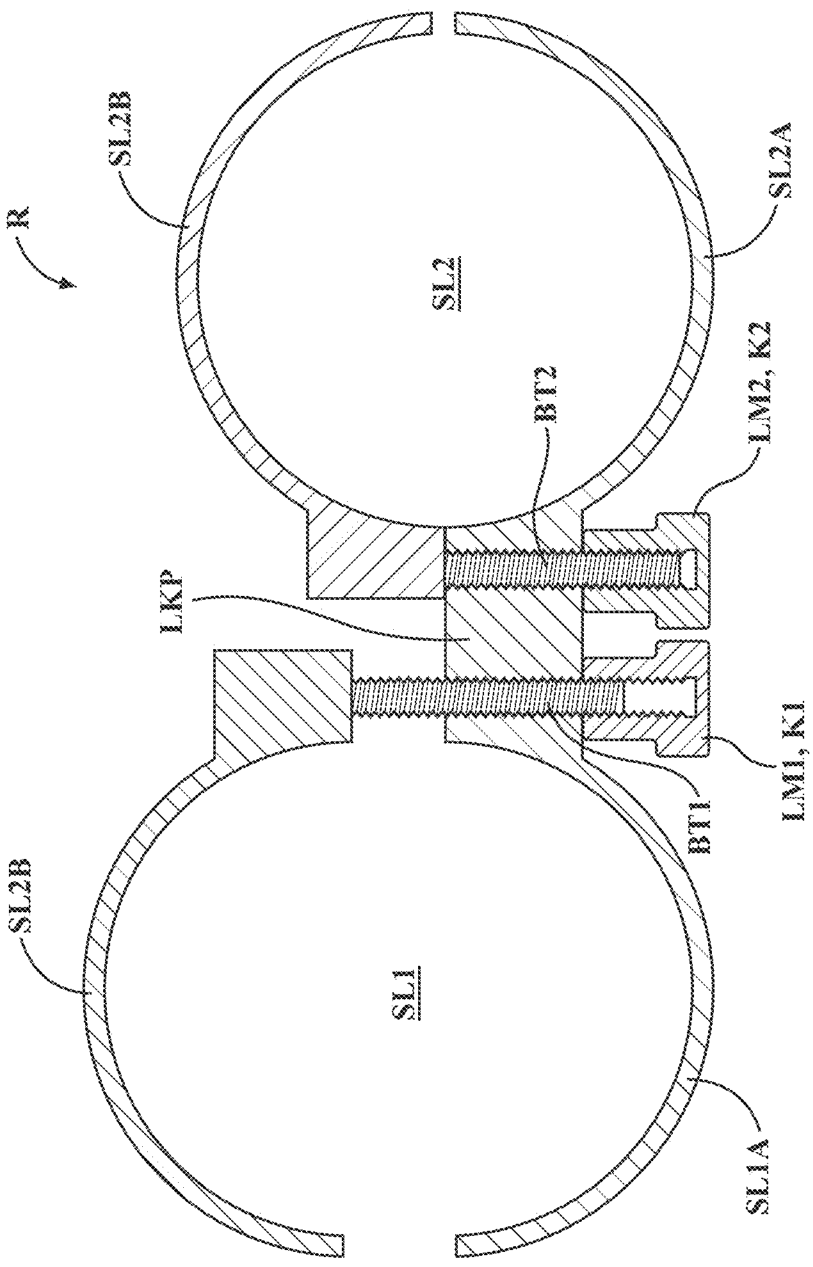
FIG. 22 is a top diagrammatic view showing a configuration of the retainer comprising separately and independently moveable sleeves, with each sleeve comprising a dedicated locking mechanism, according to one implementation.

It is contemplated to have the sleeves SL2, SL2 of the retainer R be individually and/or separably actuated. FIG. 22 illustrates one example of this configuration. The example of FIG. 22 is like that of FIG. 15, but with each sleeve SL1, SL2 comprising each its own dedicated locking mechanism LM1, LM2, respectively. A first locking mechanism LM1 is coupled to the first sleeve SL1 and can be actuated to rotationally lock the first body TB1 to the first sleeve SL1. A second locking mechanism LM2 is coupled to the second sleeve SL2 and can be actuated to rotationally lock the second body TB2 to the second sleeve SL2. Each sleeve SL1 and SL2 is separately split into sleeve portions SL1A, SL1B and SL2A, SL2B, respectively. Each locking mechanism LM1, LM2 respectively includes a knob K1, K2 coupled to the bolt BT1, BT2 that extends through a shared link portion LKP of the retainer R. Each bolt BT1, BT2 is fixed at the distal end to the second sleeve portion SL2A, SL2B. Each knob K1, K2 can be separately rotated to open and close the respective sleeve SL1, SL2. This example illustrates use of the locking mechanisms LM1, LM2 with knobs and bolts. However, this configuration is possible with any of the described examples (e.g., levers, teeth, push buttons, etc.). By including separate locking mechanisms LM1, LM2, the retainer R is provided with the ability to hold one of the bodies TB1, TB2 in place, while enabling rotational adjustment or removal of the other one of the bodies TB1, TB2. This configuration could be advantageous in situations where only one body TB1, TB2 requires adjustment or where only one body TB1, TB2 needs to be removed. The tensor T could be left inserted into the knee joint with the one body TB1, TB2 rotationally locked in position, while the other body TB1, TB2 can be rotationally adjusted or removed (separate from the locked body). The one body may be locked in a preferred pose that the surgeon wants to maintain without affecting the preferred pose by adjusting the other body. Removal of one body could be for purposes, such as adjusting, replacing, or changing a paddle, or for performing a temporary cleaning of the one body.

5B. Adjustable Link Portion

Several retainer R configurations described above include the link portion LKP rigidly coupled between the sleeves SL1, SL2 for fixing the lateral position of the sleeves SL1, SL2, or sleeve portions, relative to one another. In this section, and with reference to FIGS. 23-26, several examples are described of an adjustable link portion ALKP with one or more link portion joints LPJ. The adjustable link portion ALKP advantageously enables adjustment of the sleeves SL1, SL2 relative to another to provide additional degrees of freedom for the tensor T. The examples shown in FIGS. 23-26 include the sleeves SL2, SL2 of the retainer R being individually and/or separably actuated (as described in the example of FIG. 22). This way, the bodies TB1, TB2 can be rotationally adjusted and locked within each respective sleeve SL1, SL2. With the adjustable link portion ALKP and the rotatable bodies TB1, TB2, the tensor T could potentially provide two or more degrees of freedom for each body TB1, TB2.

In these examples, it is contemplated that the adjustable link portion ALKP may be utilized in addition to the retainer R or without the retainer R. For example, the sleeves SL1, SL2 could be non-adjustable such that the sleeves SL1, SL2 could be permanently or semi-permanently coupled to each respective body TB1, TB2. Hence, the locking mechanism LM may or may not be utilized for each sleeve SL1, SL2. Alternatively, the adjustable link portion ALKP may be directly coupled to each respective tensor body TB1, TB2 so that no sleeve is required. The degrees of freedom provided by the adjustable link portion ALKP may be sufficient to enable the rotational adjustment of each body TB1, TB2.

Figure 23:
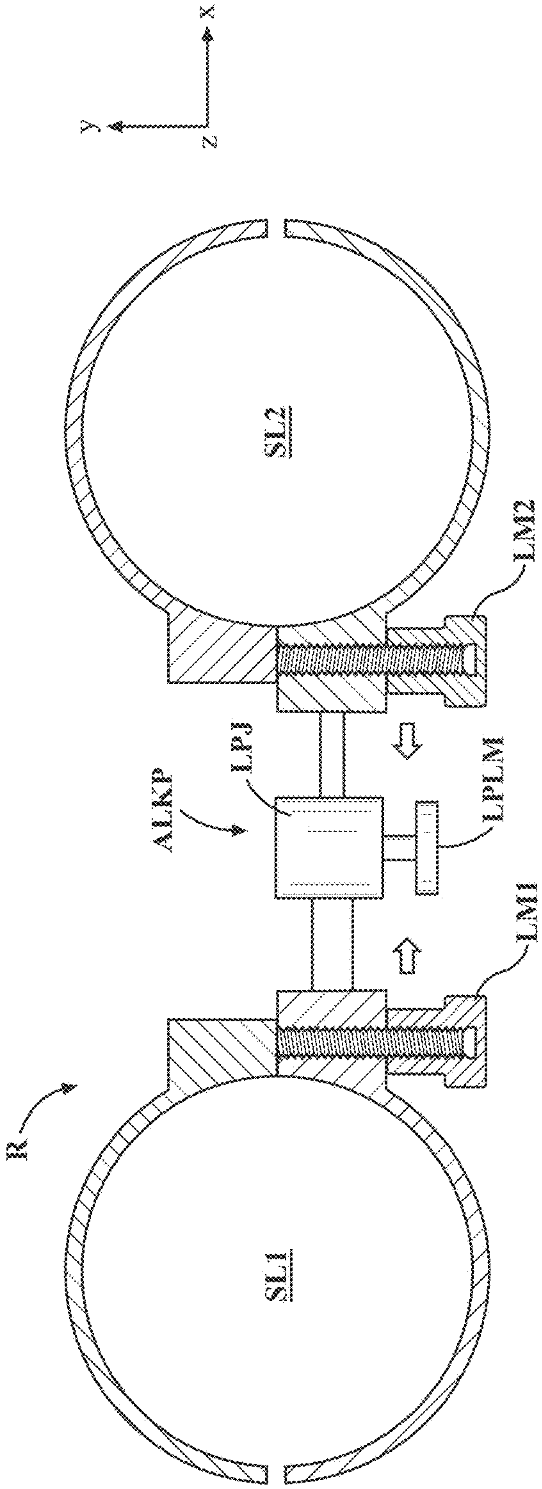
FIG. 23 is s a top diagrammatic view showing a configuration of a holding device for holding the tensor bodies including an adjustable linking portion with a translational joint coupled between sleeves, and wherein the holding device holds the sleeves in a laterally spaced configuration, according to one implementation.
Figure 24:
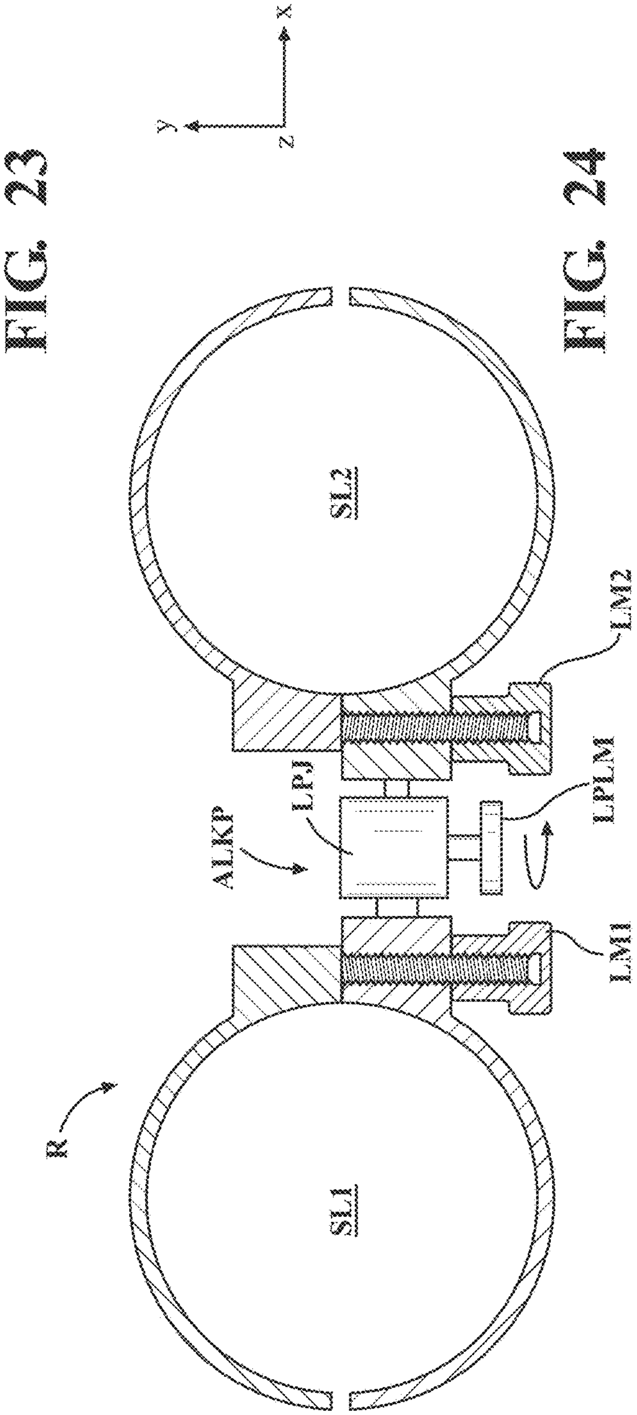
FIG. 24 is a top diagrammatic view of the configuration of FIG. 23 showing the holding mechanism in a laterally closed state and a locking mechanism to lock the translational joint of the linking portion, according to one implementation.

In the example of FIGS. 23 and 24, the adjustable link portion ALKP separates the sleeves SL1, SL2 and the link portion joint LPJ is a translational joint. The translational direction will be perpendicular to the axes BA1, B2, of the bodies TB1, TB2. The translational link portion joint LPJ can enable one degree of freedom (e.g., along the X-direction) translational adjustment of the sleeves SL1, SL2 so as to increase or decrease the lateral distance between the bodies TB1, TB2. By doing so, the adjustable link portion ALKP enables translational adjustment of paddles UP, LP of each body TB1, TB2. In FIG. 23, the adjustable link portion ALKP is placed in a laterally extended position to maximize separation between the sleeves SL1, SL2. In FIG. 24, the adjustable link portion ALKP is placed in a laterally retracted position to minimize separation between the sleeves SL1, SL2. This design can aid the tensor T to further adjust for different sized knees or bones. The translational link portion joint LPJ can be a telescoping bar, a prismatic joint, a slide linkage, or the like. Additionally, the adjustable link portion ALKP may comprise more than one translational link portion joint LPJ. For example, a second translational link portion joint LPJ may be provided perpendicular to the translational link portion joint LPJ shown in FIGS. 23 and 24. The second translational link portion joint LPJ can enable independent adjustment of a second degree of freedom (e.g., along the Y-direction) translational adjustment of the sleeves SL1, SL2. It is contemplated to have a third translational link portion joint LPJ perpendicular to the first and second translational link portion joints LPJ to enable independent adjustment of a third degree of freedom (e.g., Z-direction) translational adjustment of the sleeves SL1, SL2.

Optionally, a link portion locking mechanism LPLM can be operatively coupled to the link portion joint LPJ to facilitate locking and unlocking of the link portion joint LPJ. In turn, the link portion locking mechanism LPLM can translationally lock/unlock the sleeves SL1, SL2, and the bodies TB1, TB2 relative to one another. For any of the example described herein, the link portion locking mechanism LPLM can include a configuration or user interface similar to the locking mechanism LM described in the examples of FIGS. 14-22 (e.g., knob lever, teeth, push button, etc.).

Figure 25:
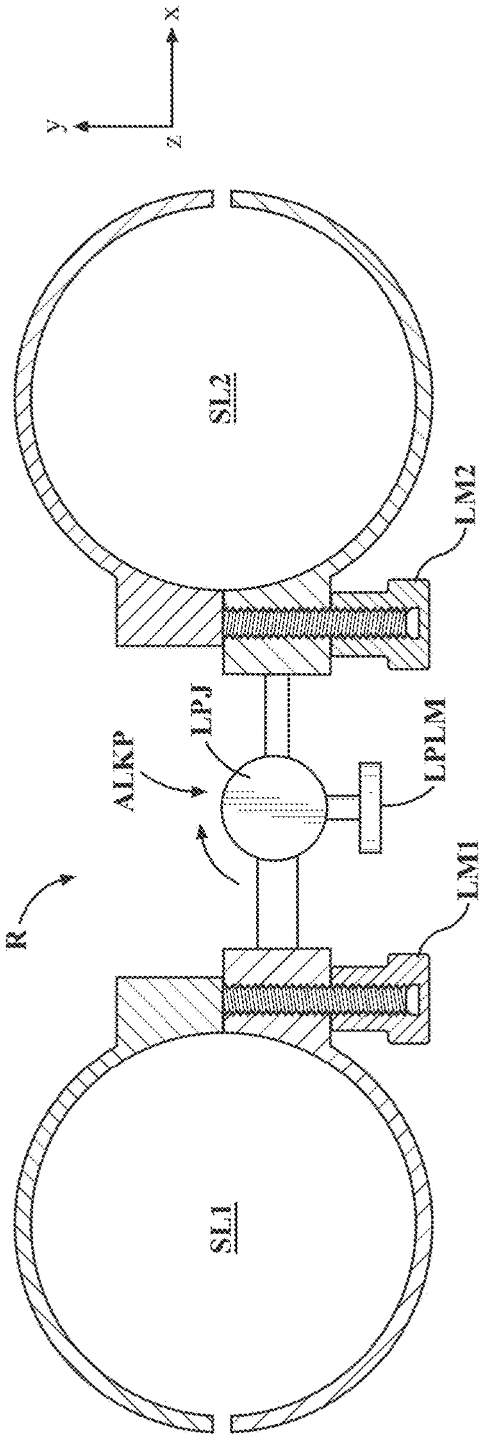
FIG. 25 is s a top diagrammatic view showing a configuration of a holding device for holding the tensor bodies including an adjustable linking portion with a rotational joint coupled between sleeves, and wherein the holding device holds the sleeves in a rotationally neutral state, according to one implementation.
Figure 26:
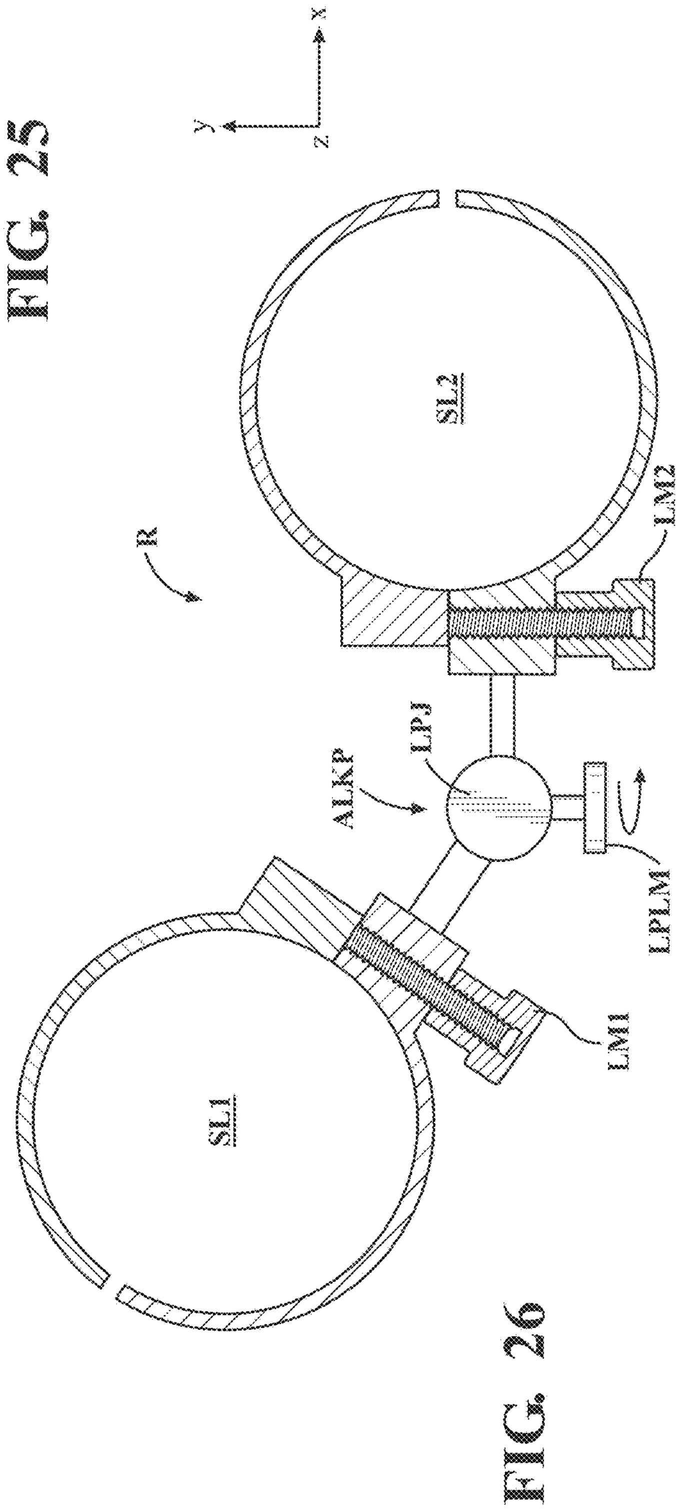
FIG. 26 is a top diagrammatic view of the configuration of FIG. 25 showing the holding mechanism in a rotationally adjusted state and a locking mechanism to lock the rotational joint of the linking portion, according to one implementation.

In the example of FIGS. 25 and 26, the adjustable link portion ALKP comprises the link portion joint LPJ being a rotational joint. The rotational direction can be parallel to the axes BA1, B2, of the bodies TB1, TB2. In one example, the rotational link portion joint LPJ can enable one degree of freedom (e.g., about the Z-direction) rotational adjustment of the sleeves SL1, SL2 so as to increase or decrease the angle or arc length between the bodies TB1, TB2. By doing so, the adjustable link portion ALKP enables angular or arc length adjustment of paddles UP, LP of each body TB1, TB2. In FIG. 23, the adjustable link portion ALKP is placed in a rotationally neutral position to maintain in-line (e.g., 0 degree) positioning between the sleeves SL1, SL2. In FIG. 24, the adjustable link portion ALKP is rotated (e.g., to about 40/140 degrees) to rotationally adjust the angle or arc length distance between sleeves SL1, SL2. The rotational link portion joint LPJ can be adjusted up to 360 degrees. This design can aid the tensor T to further adjust for different sized knees or bones or to provide fine-tuning of the pose of the paddles to provide additional contact coverage or to circumvent the patellar tendon PAT. The rotational link portion joint LPJ can be a spherical joint, gimbal joint, swivel joint, revolute joint, helical joint, universal joint, knuckle joint, or the like.

Additionally, the adjustable link portion ALKP may comprise more than one rotational link portion joint LPJ or the rotational link portion joint LPJ providing greater than one degree of freedom in rotation. For example, a second rotational link portion joint LPJ may be provided perpendicular to the rotational link portion joint LPJ shown in FIGS. 25 and 26. The second rotational link portion joint LPJ can enable independent adjustment of a second degree of freedom (e.g., about the Y-direction) rotational adjustment of the sleeves SL1, SL2. It is contemplated to have a third rotational link portion joint LPJ perpendicular to the first and second rotational link portion joints LPJ to enable independent adjustment of a third degree of freedom (e.g., about Z-direction) rotational adjustment of the sleeves SL1, SL2. Instead of multiple rotational joints, a single spherical joint, gimbal joint, swivel joint or universal joint can provide these three degrees of rotational freedom.

The link portion locking mechanism LPLM can be operatively coupled to the link portion joint LPJ to facilitate locking and unlocking of the link portion joint LPJ. In turn, the link portion locking mechanism LPLM can rotationally lock/unlock the sleeves SL1, SL2, and the bodies TB1, TB2 relative to one another. For example, a knob can be used to lock/unlock a gimbal joint.

Additionally, the adjustable link portion ALKP may combine the above implementations in any manner to include one or more link portion joints LPJ that provide both translational and rotational degrees of freedom (up to six degrees of freedom).

6. Auxiliary Paddle Components and Methods of Use

Referring to FIG. 27-32 and described herein are configurations and uses of an auxiliary paddle AP that can expand the functionality of the tensor T. The tensor T described in the examples above includes (in some configurations) the lower paddle LP designed with a planar bottom surface LBS, which is suitable to interact with a resected tibial surface, e.g., in a mid-resection workflow. However, a planar lower paddle LP may not be optimally suited for interacting with a non-resected tibia, a native tibia, or the articular surface of a tibial implant. The auxiliary paddle AP provides a work-around for enabling the tensor T to interact with a non-resected tibia, native tibia, or articular surface of the tibial implant. The auxiliary paddle AP advantageously expands the functionality of the tensor T without requiring removal or replacement of any of paddles UP, LP attached to the respective bodies TB1, TB2. This function is beneficial because a surgeon may desire to first perform a pre-resection evaluation of the knee joint (wherein the native tibial surface is in intact), and subsequently perform a mid-resection evaluation of the knee joint (wherein the tibia has been resected). The auxiliary paddle AP can easily be inserted into the tensor T to enable the tensor T to be utilized for the pre-resection evaluation. Thereafter, the auxiliary paddle AP can be easily removed from the tensor T to enable the tensor T to perform the mid-resection evaluation, e.g., with the upper and lower paddles UP, LP. Other uses for the auxiliary paddle AP are possible beyond the pre-resected evaluation. For example, the auxiliary paddle AP can be utilized in a post-implantation evaluation of the knee joint wherein a femoral prosthetic is implanted in the femur and a tibial prosthetic is implanted in the tibia. The auxiliary paddle AP thus can interact with any native (non-resected) articular bone surface(s) or any artificial articular bone surface(s).

Figure 29:
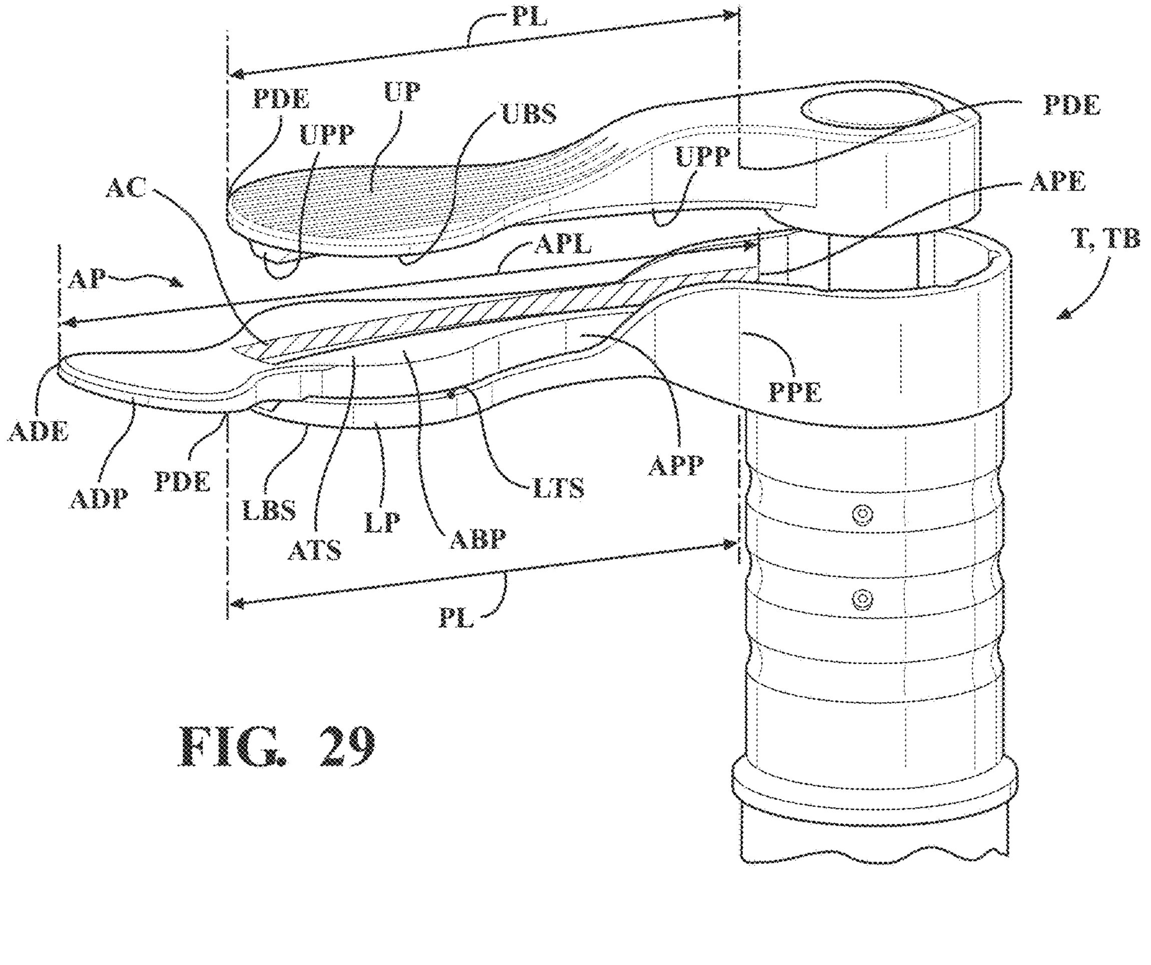
FIG. 29 is a perspective view of an assembly including the auxiliary paddle being inserted between the upper and lower paddles of one tensor body, according to one implementation.
Figure 30:
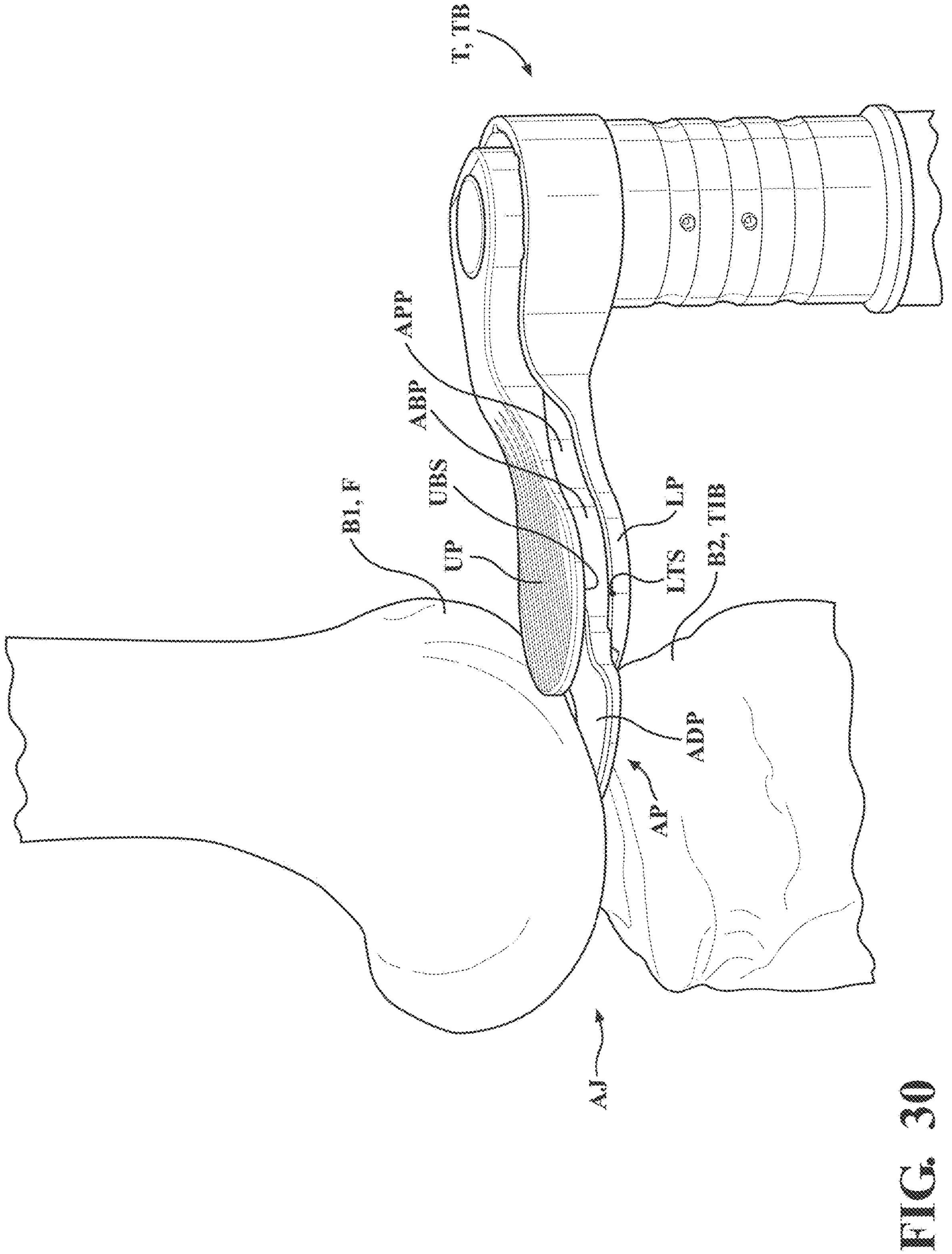
FIG. 30 is a perspective view of the assembly of FIG. 29 showing the auxiliary paddle captured between the paddles of the tensor body and a distal portion of the auxiliary paddle being used to manipulate the femur and tibia of the knee joint, according to one implementation.

The auxiliary paddle AP is configured to be inserted between and captured by the upper paddle UP and the lower paddle LP of one body TB1. More specifically, the auxiliary paddle AP is configured to be captured between the bottom surface UBS of the upper paddle UP and the top surface LTS of the lower paddle LP (as can be seen in FIGS. 29 and 30). For simplicity, the respective Figures illustrate a single auxiliary paddle AP utilized with the first body TB1. One auxiliary paddle AP can be utilized with each body TB1, TB2 (one at a time) or the tensor T may be utilized simultaneously with two separate auxiliary paddles AP (one for each body TB1, TB2). In some instances, the tensor T can include a common lower paddle LP shared among the bodies TB1, TB2. In this case, the one auxiliary paddle AP can be configured to be concurrently utilized with both bodies TB1, TB2. The orthopedic tensor T can include the auxiliary paddle or paddles AP, as part of a kit or assembly.

6A. Auxiliary Paddle Designs

Figure 27:
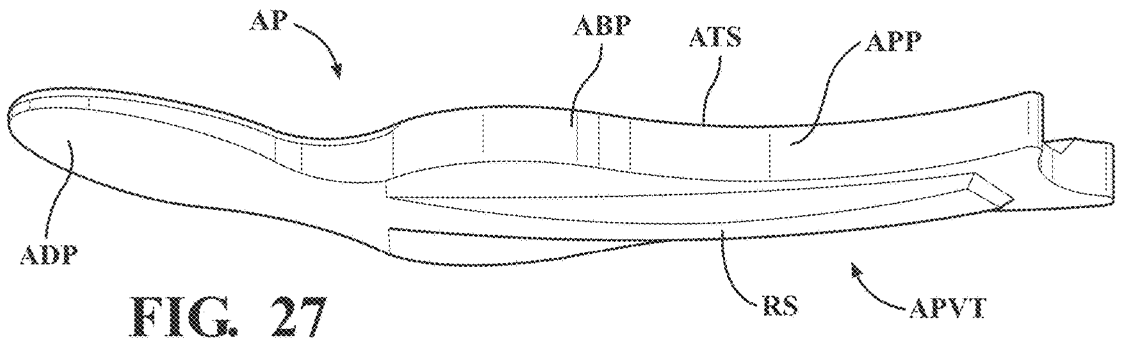
FIG. 27 is a perspective view of an auxiliary paddle that is configured to be used with the tensor, according to one implementation.
Figure 28:
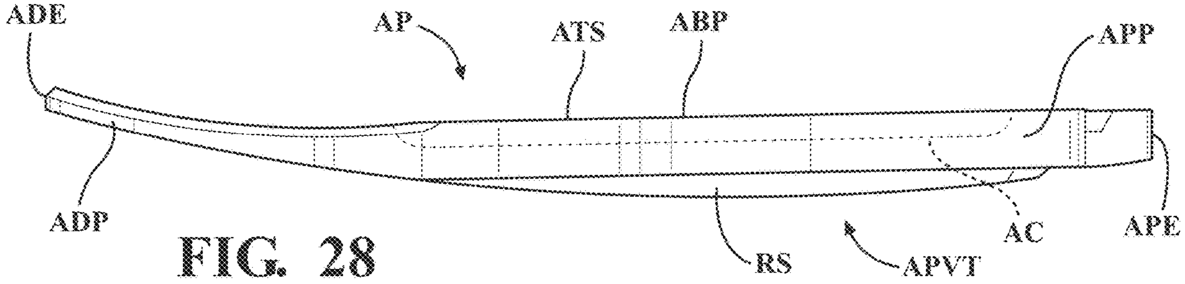
FIG. 28 is a side view, partially in phantom, of the auxiliary paddle of FIG. 27.

The configurations and implementations of the auxiliary paddle AP will now be described. With reference to one example, as shown in FIGS. 27-29, the auxiliary paddle AP comprises a body APB that includes a proximal portion APP and a distal portion ADP. In one example, the proximal portion APP is configured to be captured between the upper and lower paddles UP, LP. As shown in FIG. 29, the proximal portion APP can rest upon on the top surface LTS of the lower paddle LP prior to being captured. The body APB or proximal portion APP of the auxiliary paddle AP can have a shape that substantially conforms to a shape of the lower paddle LP (as shown in FIG. 29).

The distal portion ADP extends from the proximal portion APP. The distal portion ADP is the part of the auxiliary paddle AP that is configured to directly contact the first and second bones B1, B2 of the anatomical joint AJ. Once the auxiliary paddle AP is inserted into the tensor T, the distal portion ADP will extend beyond a distal end PDE of each of the paddles UP, LP. As will be described below, there are instances in which portions of the distal portion ADP may be captured between the upper and lower paddles UP, LP.

As shown in FIG. 29, the upper and lower paddles UP, LP each include a length PL defined between a proximal end PPE and the distal end PDE of each paddle. The paddle length PL may be the same or slightly different between the upper and lower paddles UP, LP. The auxiliary paddle AP has a length APL defined between a proximal end APE of the auxiliary paddle AP and a distal end ADE of the distal portion ADP of the auxiliary paddle AP. The length APL of the auxiliary paddle AP can be greater than the length PL of each of the upper and lower paddles UP, LP.

The auxiliary paddle AP comprises a pivot APVT being provided on the body APB of the auxiliary paddle AP and/or coupled to the distal portion ADP of the auxiliary paddle AP. The pivot APVT is designed to enable the auxiliary paddle AP to apply force to the upper paddle UP in response to the distal portion ADP contacting the first and/or second bones B1, B2 of the anatomical joint AJ. The effort exerted by the bones on the distal portion ADP causes the auxiliary paddle AP to apply a load to the upper paddle UP. The auxiliary paddle AP is utilized in conjunction with the existing paddles UP, LP and the tensor control system TCS. When the auxiliary paddle AP is captured, the distal portion ADP of the auxiliary paddle AP can be understood as a substitute for the upper and lower paddles UP, LP with respect to contacting the bones.

In the example shown in FIGS. 27-30, the pivot APVT is provided or formed on the body APB of the auxiliary paddle AP. Here, the auxiliary paddle AP includes a rocker surface RS. The rocker surface RS can engage the top surface LTS of the lower paddle LP. In the example shown, the rocker surface RS can comprise a convex, contoured, or curved portion bottom surface of the body ABP and/or a projecting extending from the bottom surface of the body ABP. The rocker surface RS can enable the auxiliary paddle AP to pivot or provide a fulcrum to enable the auxiliary paddle AP to function as a lever in response to the distal portion ADP contacting the bones. The auxiliary paddle AP can comprise a top surface ATS opposite the rocker surface RS. The top surface ATS can be planar and configured to engage the bottom surface UBS of the upper paddle UP to securely capture the auxiliary paddle AP and improve measurement accuracy. Within the top surface ATS, a channel AC can be formed to enable the auxiliary paddle AP to engage with a correspondingly shaped projection UPP formed or disposed on the bottom surface UBS of the upper paddle UP. The projection UPP enters into the channel AC once the auxiliary paddle AP is captured. Engagement between the projection UPP and channel AC can aid in ensuring the auxiliary paddle AP is securely attached to the body TB once captured without possibility of slipping out.

As shown in the example of FIGS. 27-29, the distal portion ADP has a tongue-like configuration with opposing top and bottom surfaces that are designed to contact the first and second bones B1, B2, respectively (as shown in FIG. 30). The distal portion ADP can comprise a curvature. The curvature can be provided to improve the mechanical advantage in forcing the bones apart. The curved distal portion ADP can extend above a plane of the top surface ATS. Alternatively, the curved distal portion ADP can be flat, or curved downwards, e.g., below the plane of the top surface ATS. To facilitate a smooth lever action for the auxiliary paddle AP, the curvature of the distal portion ADP can be along the same radius or arc of the rocker surface RS. In the example shown, the distal portion ADP shares a common surface, and seamlessly transitions to, the rocker surface RS. The distal portion ADP can include a configuration other that specifically shown. For example, the distal portion ADP could include a wider tongue, or two surfaces that flare apart from one another (e.g., flared apart horizontally or vertically).

In some instances, same configuration of the auxiliary paddle AP (as shown in FIGS. 27-30) can be utilized in a flipped-over manner. When flipped over, the top surface ATS of the auxiliary paddle AP engages the top surface LTS of the lower paddle LP and the rocker surface RS of the auxiliary paddle AP engages the bottom surface UBS of the upper paddle UP. Alternatively, the auxiliary paddle AP can include an opposite design from what is shown, wherein the rocker surface RS is located on the top surface ATS instead of the bottom surface of the auxiliary paddle AP.

The body APB of the auxiliary paddle AP, including the distal portion ADP, the rocker surface RS, and the top surface ATS can be part of a single, unitary, or monolithic body or integrally formed of a common material. The common material can be a metal, metal alloy, PTFE, or the like. Alternatively, any features of the body APB could be separate components that are assembled onto the body. For example, the rocker surface RS could include a separate component formed of different material than the body APB.

Figure 31:
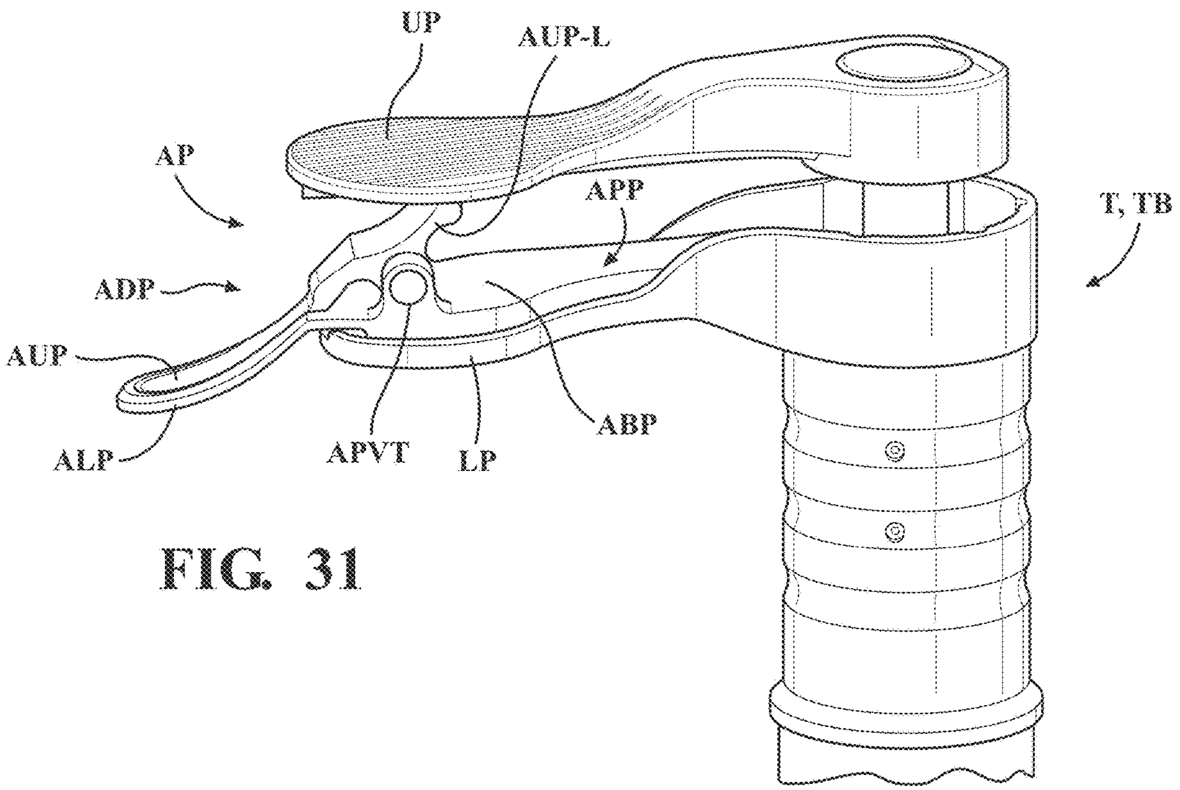
FIG. 31 is a perspective view of an assembly including another configuration of the auxiliary paddle being inserted between the upper and lower paddles of one tensor body, wherein the paddles of the tensor body are in an open state, and the auxiliary paddle comprises hinged auxiliary distal paddles being in a closed state, according to one implementation.
Figure 32:
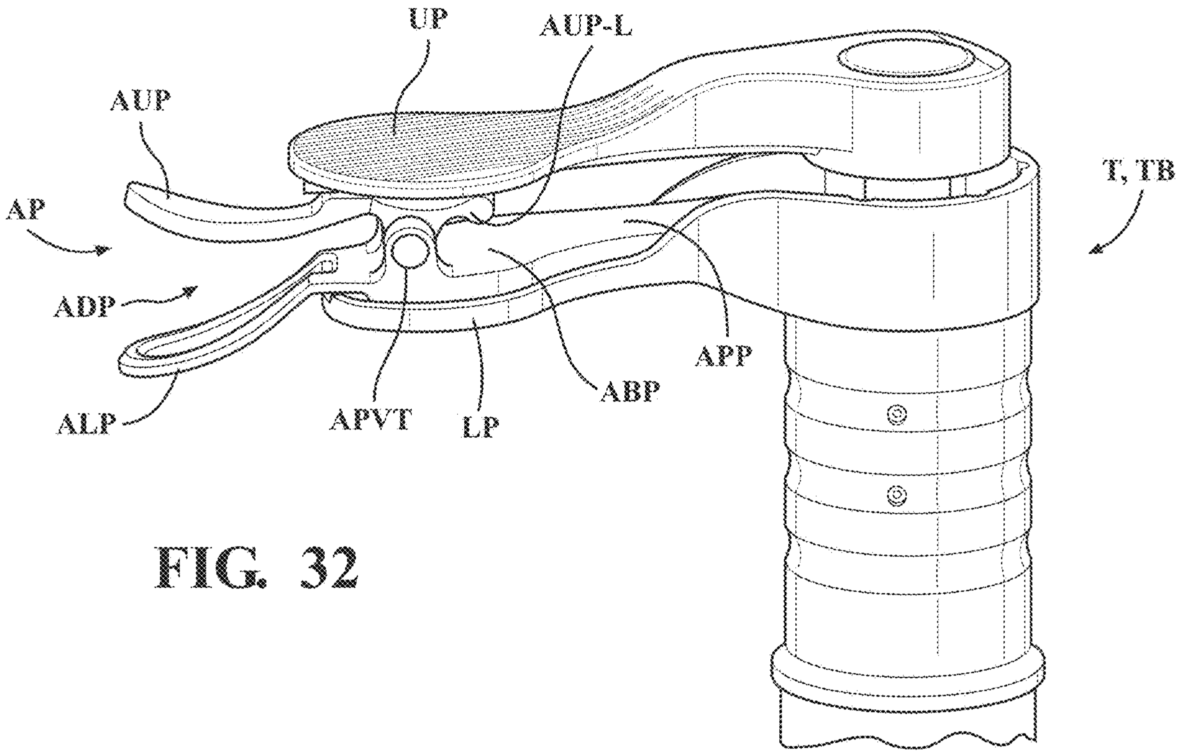
FIG. 32 is a perspective view of the assembly of FIG. 32 wherein the paddles of the tensor body are in a closed state, and the hinged auxiliary distal paddles being in an open state, according to one implementation.

In another example shown in FIGS. 31 and 32, the pivot APVT of the auxiliary paddle AP is implemented with hinged components. The distal portion ADP of the auxiliary paddle AP includes an auxiliary upper paddle AUP that is configured to contact the upper paddle UP and contact the first bone B1. The distal portion ADP also includes an auxiliary lower paddle ALP that is configured to contact the lower paddle LP and contact the second bone B2. The auxiliary upper paddle AUP is pivotable relative to the auxiliary lower paddle ALP to apply force to the upper paddle UP in response to the distal portion ADP contacting the first and second bones B1, B2. The pivot APVT is a hinge coupled between the auxiliary upper paddle AUP and auxiliary lower paddle ALP. The body APB of the auxiliary paddle AP can rest on the lower paddle LP. The auxiliary lower paddle ALP can be in a fixed relationship relative to the body APB and the auxiliary upper paddle AUP can be in a pivoting relationship relative to the body APB. When the auxiliary paddle AP is inserted into the tensor T, the pivot APVT can be located between the upper and lower paddles UP, LP. The auxiliary upper paddle AUP includes a lever AUP-L that extends rearward of the pivot APVT and is designed to engage the bottom surface UBS of the upper paddle UP.

As shown in FIG. 31, the body TB1 of the tensor T has the paddles UP, LP in a spaced relationship wherein the upper paddle UP touches, but does not yet press down on, the auxiliary upper paddle AUP. In this configuration, the auxiliary upper paddle AUP and the auxiliary lower paddle ALP can be in a closed state wherein the distal paddles AUP, ALP arc touching. The paddles UP, LP can be placed in this position to hold the auxiliary paddle AP in the closed state. The auxiliary lower paddle ALP can define a spacing that is configured to receive and surround the perimeter of the auxiliary upper paddle AUP in the closed state. The auxiliary paddle AP can be inserted into the anatomical joint JP while in the closed state (similar to FIG. 31). The distal paddles AUP, ALP can interact with the first and second bone B1, B2, respectively, while in the closed state. The distal paddles AUP, ALP can comprise corresponding curvatures to improve the mechanical advantage in forcing the bones apart.

An open state of the auxiliary paddle AP is demonstrated in FIG. 32. The upper paddle UP can be commanded to move downwards towards the lower paddle LP. The upper paddle UP presses down on the lever AUP-L which causes the auxiliary upper paddle AUP to rotate about the pivot APVT. As a result, the auxiliary upper paddle AUP becomes spaced apart from the auxiliary upper paddle AUP (e.g., in the open state). The auxiliary paddle AP can be inserted between the bones in the closed state and subsequently changed to the open state. This process can cause the bones to separate or distract to enable the tensor control system TCS to obtain readings related to the joint AJ. Movement of the upper paddle UP can cause movement of the distal paddles AUP, ALP from the closed state to open state, from the open state to the closed state, or to any position in between the states.

Modifications are contemplated to the auxiliary paddle AP configuration of FIGS. 31 and 32. For example, the auxiliary lower paddle ALP could alternatively or additionally move in response to corresponding movement of the upper paddle UP. The pivot APVT can be any type of hinge or rotational joint other than what is shown. The pivot APVT could be placed at a location other than what is shown. The distal paddles AUP, ALP could be planar or flat. The lever AUP-L could be additionally or alternatively provided for the auxiliary lower paddle ALP.

6B. Tensor Control Schemes for Use with Auxiliary Paddle

Here, operation of tensor control system TCS will be described in conjunction with use of the auxiliary paddle AP. The tensor control system TCS can be utilized to facilitate capture the auxiliary paddle AP and to facilitate sensing of displacement or force caused by the auxiliary paddle AP interacting with the bones.

First, the auxiliary paddle AP is inserted into the tensor T or body TB1, e.g., between the paddles UP, LP (as shown in FIG. 29 for example). The auxiliary paddle AP at this stage can passively rest atop the top surface LTS of the lower paddle LP. The tensor control system TCS controls the drive assembly DA to move the upper paddle UP (e.g., downwards) relative to the lower paddle LP. As a result of the upper paddle movement UP, the auxiliary paddle AP becomes captured between the paddles UP, LP. Alternatively, or additionally, the auxiliary paddle AP may be captured by movement of the lower paddle LP relative to the upper paddle UP, or captured by movement of both paddles UP, LP. The auxiliary paddle AP can be secured to the tensor T solely by being captured between the paddles UP, LP, e.g., the opposing forces provided on the auxiliary paddle AP by the paddles UP, LP. In some instances, the auxiliary paddle AP and/or the lower paddle LP can include a retention feature for temporarily retaining the auxiliary paddle AP to the lower paddle LP before capture. For example, the lower paddle LP can include side walls that are designed or shaped to temporarily hold and to prevent the auxiliary paddle AP from sliding off the lower paddle LP before capture. When the auxiliary paddle AP is captured, the distal portion ADP of the auxiliary paddle AP will be extending beyond the distal end PDE of each of paddle UP, LP. The distal portion ADP is then utilized to contact the bones of the anatomical joint (as shown in FIG. 30 for example).

As described in the preceding sections, the tensor T can operate in the displacement control mode DCM, force control mode FCM, or force-displacement control mode. Any of these modes can be utilized to capture the auxiliary paddle AP and to obtain measurements resulting from the auxiliary paddle AP contacting the bones. The tensor control system TCS can be controlled to trigger the capture of the auxiliary paddle AP through the clinical application CA and/or through user input TID devices on the tensor T itself.

To capture the auxiliary paddle AP in the displacement control mode DCM, the tensor control system TCS commands displacement of the upper paddle UP towards the lower paddle LP. This process can be manually guided or automatically implemented. In one example, the tensor control system TCS can automatically lower the upper paddle UP until a predetermined capture displacement between the upper paddle UP and lower paddle LP is detected or reached. The predetermined capture displacement can be utilized to prevent overdriving the upper paddle UP onto the auxiliary paddle AP and possibly damaging the system components. The predetermined capture displacement can be detected by a displacement or position sensor, such as the motor encoder M, or any other sensing system described herein. The predetermined capture displacement can be indicative of the auxiliary paddle AP being appropriately or sufficiently captured between the paddles UP, LP. For example, the tensor control system TCS can include predetermined data related to the geometry of the auxiliary paddle AP and derive the predetermined capture displacement from such data. In one example, the predetermined capture displacement can be defined by a difference between a current spacing between the paddles UP, LP and the thickness of the auxiliary paddle AP. In another example, the paddles UP, LP may be automatically placed in a maximum opened position and then the upper paddle UP can be automatically lowered by the predetermined capture displacement. The maximum opened position can provide a consistent reference displacement to avoid additional calculations related to the various possible paddle spacing. In another example, the user can utilize the clinical application CA and/or user input devices TID on the tensor T itself to lower the upper paddle UP in the displacement control mode DCM. The user-implemented lowering of the upper paddle UP can be regulated by the tensor control system TCS so as to not exceed the predetermined capture displacement. In other words, the user can control the tensor T to lower the upper paddle UP until the tensor control system TCS determines that the auxiliary paddle is sufficiently captured. Thereafter, the tensor control system TCS can disable further movement of the upper paddle UP and/or provide a visual confirmation to the user on a display device that the auxiliary paddle AP has been captured and is ready for use. Such visual guidance can be presented on any of the displays described herein, including the head-mounted display.

To utilize the auxiliary paddle AP to obtain joint measurements in the displacement control mode DCM, the distal portion ADP of the auxiliary paddle AP contacts the bones, and in response, the auxiliary paddle AP will apply force to the upper paddle UP. The displacement or position sensor can measure a resulting displacement between the paddles UP, LP in response to force applied to the upper paddle UP by the auxiliary paddle AP. Alternatively, or additionally, the force sensor S can be utilized to measure a resulting force applied to the upper paddle UP by the auxiliary paddle AP. The tensor control system TCS can utilize the measured displacement and/or force to obtain readings about the joint AJ, such as laxity, stiffness, ligament balance, kinematics, flexion, extension and/or range of motion. In the displacement control mode DCM, the tensor control system TCS can also be configured to control the paddles UP, LP in a manner that places the auxiliary paddle AP (of FIG. 31-32) in the open or closed state. For example, the tensor control system TCS can include predetermined data related to the geometry of the auxiliary paddle AP and use the predetermined data to move the upper paddle UP in a manner required to open or close the distal paddles AUP, ALP.

To capture the auxiliary paddle AP in the force control mode FCM, the tensor control system TCS commands movement of the upper paddle UP towards the lower paddle LP. This process can be manually guided or automatically implemented. In one example, the tensor control system TCM can automatically lower the upper paddle UP until a predetermined capture force applied to the upper paddle UP by the auxiliary paddle AP is detected or reached. The predetermined capture force can be utilized to prevent overdriving the upper paddle UP onto the auxiliary paddle AP and possibly damaging the system components. The predetermined capture force can be detected by the force sensor S. The predetermined capture force can be indicative of the auxiliary paddle AP being appropriately or sufficiently captured between the paddles UP, LP. For example, the tensor control system TCS can include predetermined data related to the geometry of the auxiliary paddle AP and derive the predetermined capture force from such data. Alternatively, or additionally, the predetermined capture force can be derived from factory measurements based on tests involving capturing of the auxiliary paddle AP. The predetermined capture force can also be a maximum allowable force of the tensor T or any arbitrary force less than the maximum allowable force. In another example, the paddles UP, LP may be automatically placed in a maximum opened position and then the upper paddle UP can be automatically lowered until the predetermined capture force is reached. In another example, the user can utilize the clinical application CA and/or user input devices TID on the tensor T itself to lower the upper paddle UP in the force control mode FCM. The user-implemented lowering of the upper paddle UP can be regulated by the tensor control system TCS so as to not exceed the predetermined capture force. In other words, the user can control the tensor T to lower the upper paddle UP until the tensor control system TCS determines that the predetermined capture force is reached and the auxiliary paddle is sufficiently captured. Thereafter, the tensor control system TCS can disable further movement of the upper paddle UP and/or provide a visual confirmation to the user on a display device that the auxiliary paddle AP has been captured and is ready for use. Such visual guidance can be presented on any of the displays described herein, including the head-mounted display.

To utilize the auxiliary paddle AP to obtain joint measurements in the force control mode FCM, the distal portion ADP of the auxiliary paddle AP contacts the bones, and in response, the auxiliary paddle AP will apply force to the upper paddle UP. The force sensor S can measure a resulting force applied to the upper paddle UP by the auxiliary paddle AP. The tensor control system TCS can utilize the measured force to obtain readings about the joint AJ, such as laxity, stiffness, ligament balance, kinematics, flexion, extension and/or range of motion. In the force control mode FCM, the tensor control system TCS can also be configured to control the paddles UP, LP in a manner that places the auxiliary paddle AP (of FIG. 31-32) in the open or closed state. For example, the tensor control system TCS can include predetermined forces indicative of the open state and closed state and move the upper paddle UP in a manner required to open or close the distal paddles AUP, ALP.

The tensor control system TCS can combine the above-described functions or features of displacement and/or force to capture the auxiliary paddle AP and utilize the auxiliary paddle AP to obtain joint measurements in the force-displacement control mode.

The tensor control system TCS can capture the auxiliary paddle AP in any one of the described modes and utilize the auxiliary paddle AP to obtain joint measurements in any other one of the described modes. The same mode need not be utilized for both purposes. Additionally, the tensor control system TCS can utilize, or switch between, any two modes to capture the auxiliary paddle AP. Also, the tensor control system TCS can utilize, or switch between, any two modes to utilize the auxiliary paddle AP to obtain joint measurements. In other implementations, the upper paddle UP may be pressed down manually by the user to capture the auxiliary paddle AP (without regard to any control mode). Then, the tensor control system TCS can lock the position of the upper paddle UP once the user confirms that the auxiliary paddle AP is captured. In yet another implementation, the tensor control system TCS may simply space the paddles UP, LP apart with just enough space required to receive the auxiliary paddle AP. Then, the user can insert the auxiliary paddle AP while the paddles UP, LP remain in this spaced position.

7. Augments/Spacers for Paddles

Figure 43:
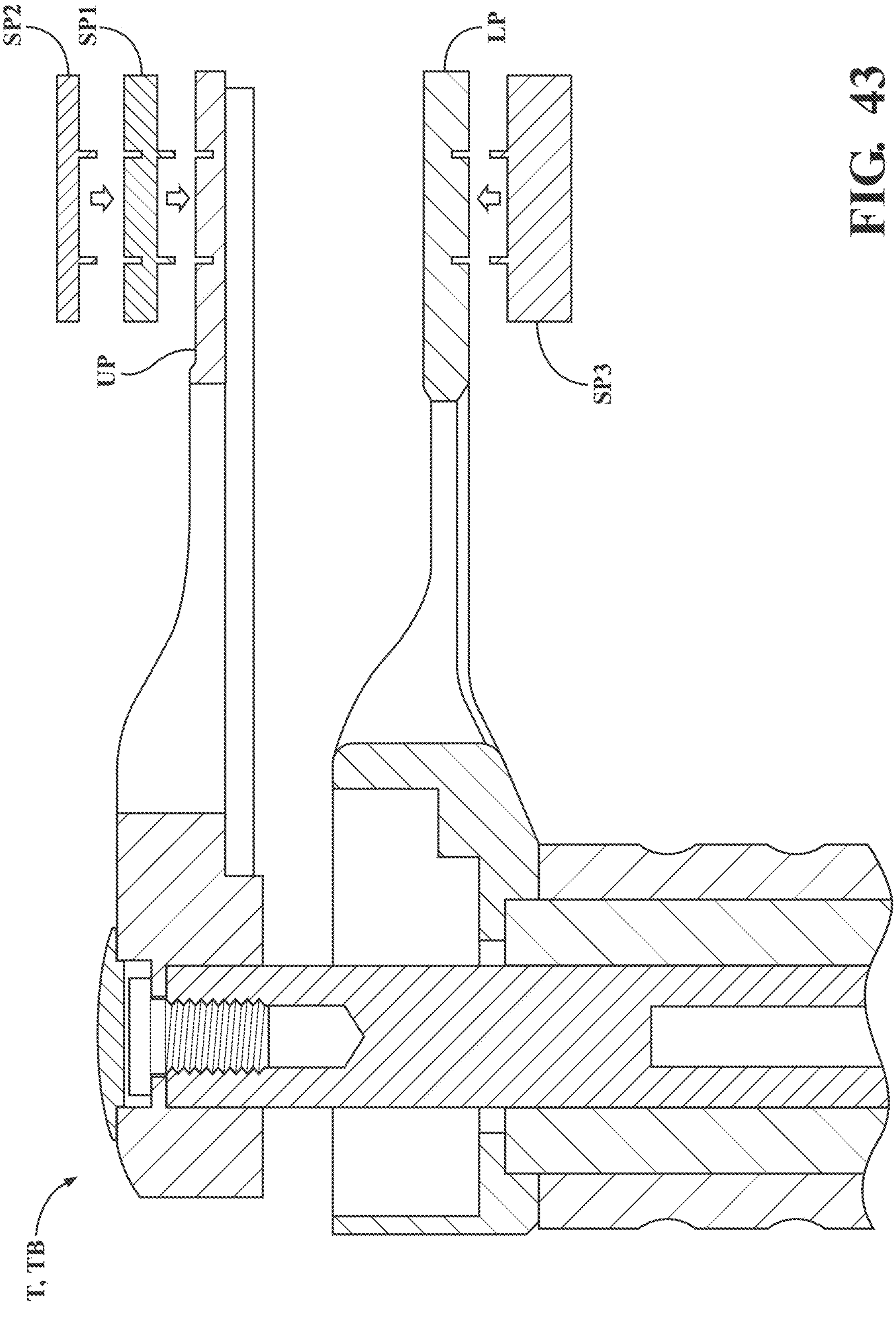
FIG. 43 is side view of the tensor whereby spacers are configured to be coupled to the paddles to increase the distraction distance range, according to one implementation.

Referring to FIG. 43, it is contemplated to include augments or spacers (SP) to any one or more paddles UP, LP, or the tensor T. The spacers (SP) can add height to any of the one or more paddles UP, LP to enable the paddles to exhibit a larger distraction distance. By providing a larger distraction distance, such spacers (SP) enable the tensor T to be more versatile and used in a greater range of applications. For example, the larger distraction distance provided by the spacers (SP) can be advantageous for a TKA revision procedure and/or for primary procedures where the tibia is resected first or where the patient has a large joint gap.

The spacer(s) SP are configured to be removably coupled to any paddle UP, LP. For instance, as shown in FIG. 43, two spacers SP1, SP2 are coupled to the bone contacting surface of the upper paddle UP and one spacer SP3 is coupled to the bone contacting surface of the lower paddle LP. The spacer(s) SP can be applied to only the upper paddle UP, only the lower paddle LP, or to both paddles simultaneously, or at different times. The coupling between the spacer(s) SP and the respective paddle UP, LP can be implemented in various ways. The spacer(s) SP can be coupled to the respective paddle UP, LP using a magnetic coupling, a mechanical coupling, or a temporary adhesive coupling, or the like. For example, as shown in FIG. 43, the spacer(s) SP or the respective paddle can have one or more projections (e.g., post or boss) and the other can have one or more corresponding holes that are configured to receive the projection(s) to secure the components together. This projection/hole technique can be utilized with a magnetic coupling to ensure the lower paddle spacer (SP) remains coupled. To increase spacer height, the spacers SP can be stacked upon one another by incorporating similar coupling techniques (e.g., as shown by SP1, SP2 and UP).

The spacers SP can be of any suitable thickness (e.g., height) and size. For example, the tensor T can be accompanied by a kit of spacers SP of incremental thicknesses (e.g., 2 mm, 5 mm, . . . 20 mm, etc.) and incremental sizes (size 1, 2, 3 . . . 10, etc.). SP of different thickness and/or size can be applied to different paddles, e.g., depending on the desired distraction range. For example, where the tensor T has separate medial and lateral upper paddles, the spacer SP on the medial upper paddle may be different size and/or thickness than the spacer SP on the lateral upper paddle. Additionally, for TKA revision procedures, the spacer(s) SP may be conveniently designed to be augment thickness increments to match the augment bone prep (e.g., the bone removed to make room for an augment implant).

The spacers SP can be of any suitable shape. For example, the spacers SP can be disc shapes or shapes that conform to a shape of the respective paddle. The spacers SP may have substantially flat upper and lower surfaces. In another example, the bone contacting surface of the spacer SP may be curved or contoured to provide an articular surface to enable the contacting bone to rotate on the spacer SP during joint evaluation. The curvature or contouring may be generic or patient-specific and additively manufactured.

The spacers SP can be used during any type of procedure and during any stage of the procedure. For example, for a primary case, the spacers SP can be used to contact native bone surfaces (prior to bone preparation), bone surfaces after preparation, or implant surfaces (after the implants are installed). The spacers SP can be used once both the femoral and tibial surfaces are resected/prepared, or once one of the femoral and tibial surfaces are resected/prepared. In a revision procedure, the spacers SP can be used to contact any of the described surfaces, as well as a primary implant (from a prior procedure). In another example, for primary or revision procedures, the spacer SP can be used to mimic the geometry of a trial implant. In yet another example, instead of attaching to a respective paddle, the spacers SP can be coupled to the (primary or revision) implant itself.

8. Tensor Methods and Workflows

With reference to FIGS. 33-41, the following section will describe numerous examples of how any of the above-described configurations of the tensor T can be utilized to assess the anatomical joint AJ. As described, the tensor T can be utilized to assess multiple parameters of the joint, such as laxity, stiffness, ligament balance, kinematics, flexion, extension and/or range of motion. In these examples, the tensor T utilizes advantages of computer aid, such as the surgical navigation system 32 and/or clinical application CA. Therefore, the surgeon need not rely on their subjective knowledge and skill to predict the state of the joint. In turn, the joint evaluation and surgical outcome can be optimized with the methods and workflows described herein.

Throughout the description of the following methods, it should be understood that the method can be utilized with one tensor body, or with two tensor bodies TB1, TB2. Depending on the configuration of the tensor T, certain steps may be performed on the knee joint once, i.e., with one tensor body TB or with simultaneous action of two tensor bodies TB1, TB2, or the steps could be performed twice, i.e., once for each respective tensor body TB1, TB2. Therefore, although some steps of the method are described in a singular manner for simplicity of description, it is contemplated that these steps can be performed in plural, simultaneous, serial, or parallel manners.

8A. Knee Extension Test

One particularly challenging part of the knee evaluation process involves determining the optimal laxity of the knee joint required to enable the knee to reach full extension (e.g., ~0 degrees knee flexion). Distracting the knee with any tensor at 0 degrees (full extension) will likely produce inaccurate measurements due to posterior capsule tightness. To assess the tension of the knee at full extension, described herein are enhanced workflows and methods for using the tensor T. The workflows and methods provide a seamless and optional automated or semi-automated assisted process for the surgeon to evaluate the knee extension while also avoiding the surgeon needing to use trial-and-error or educated guesses to adjust the tensor T or evaluate the knee joint. The techniques described herein reduce duration of evaluation process, produce accurate results, and is convenient to the surgeon.

Figure 33:
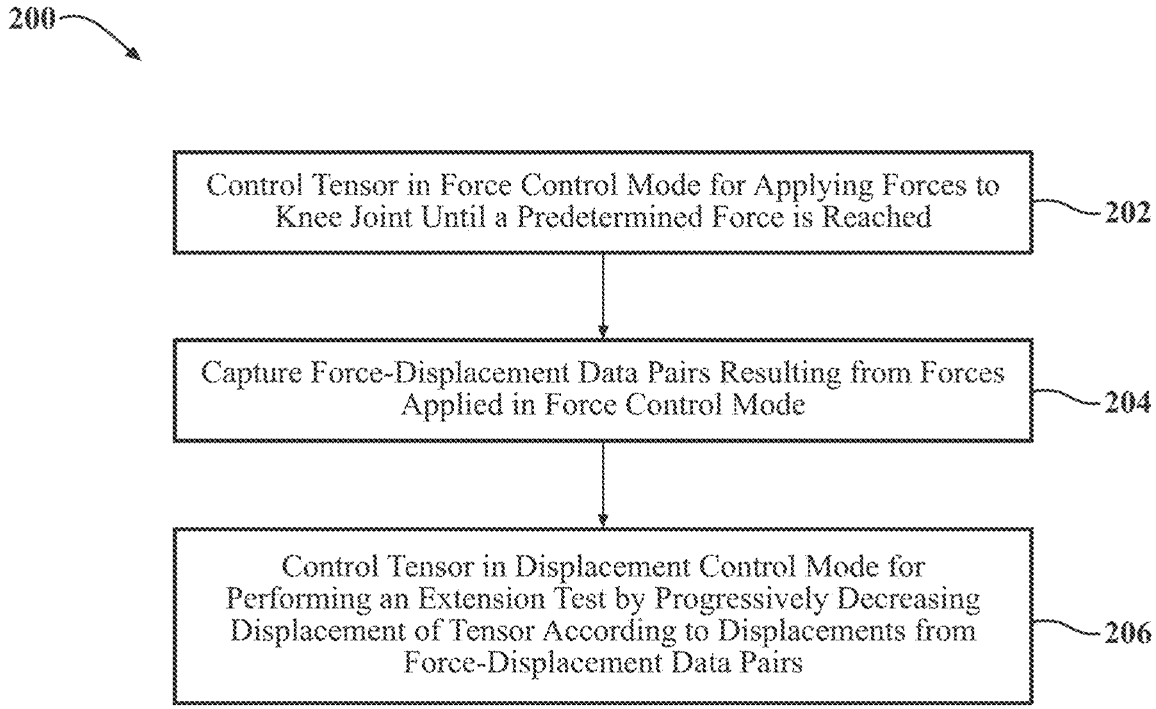
FIG. 33 is a flowchart of a method of controlling the tensor, according to one implementation.

FIG. 33 describes an example method 200 of using the tensor T to perform an “extension test”. The term “extension test” is used herein to describe the process of using the tensor T to evaluate whether the knee joint AJ can reach an acceptable full extension. The acceptable full extension pose may be a full extension (e.g., ~0 degrees of knee flexion). Alternatively, depending on the patient soft tissue and bony anatomy, as well as surgeon preferences, and surgical plan, the acceptable full extension pose may not be a completely full extension. For example, the acceptable full extension pose can be any value within a range of −1 to 5 degrees of full extension. The acceptable full extension pose could be a single value or a range of values. The acceptability of the full extension can be defined by the surgeon, the surgical plan, implant parameters, or be based on automated planning predictions made by the system 10.

The method 200 includes a first step 202 of controlling, with the tensor control system TCS, the tensor T in the force control mode FCM for applying forces to the knee joint AJ until a predetermined force is reached. In some cases, it is contemplated that the force control mode FCM can be initiated once the paddle(s) contact the bone and some initial force or resistance is measured. For example, the tensor T can be used in a displacement control mode or the paddles can be moved according to a constant velocity until some force or resistance is measured. Thereafter, the tensor T can be operated in the force control mode FCM for applying forces to the knee joint AJ until the predetermined force is reached.

Then, at step 204, the tensor control system TCS captures a plurality of force-displacement data pairs from the tensor T resulting from the tensor T applying forces in the force control mode FCM. At step 206, the tensor T is operated in the displacement control mode DCM by progressively decreasing a displacement of the tensor T according to displacements from the plurality of force-displacement data pairs. Decreasing the displacement can occur until the knee joint AJ can reach the acceptable full extension pose. The knee joint may reach acceptable full extension pose during, or after completion of, the extension test. Specific aspects, implementations, and variations of this method 200 will be described below.

Figure 34:
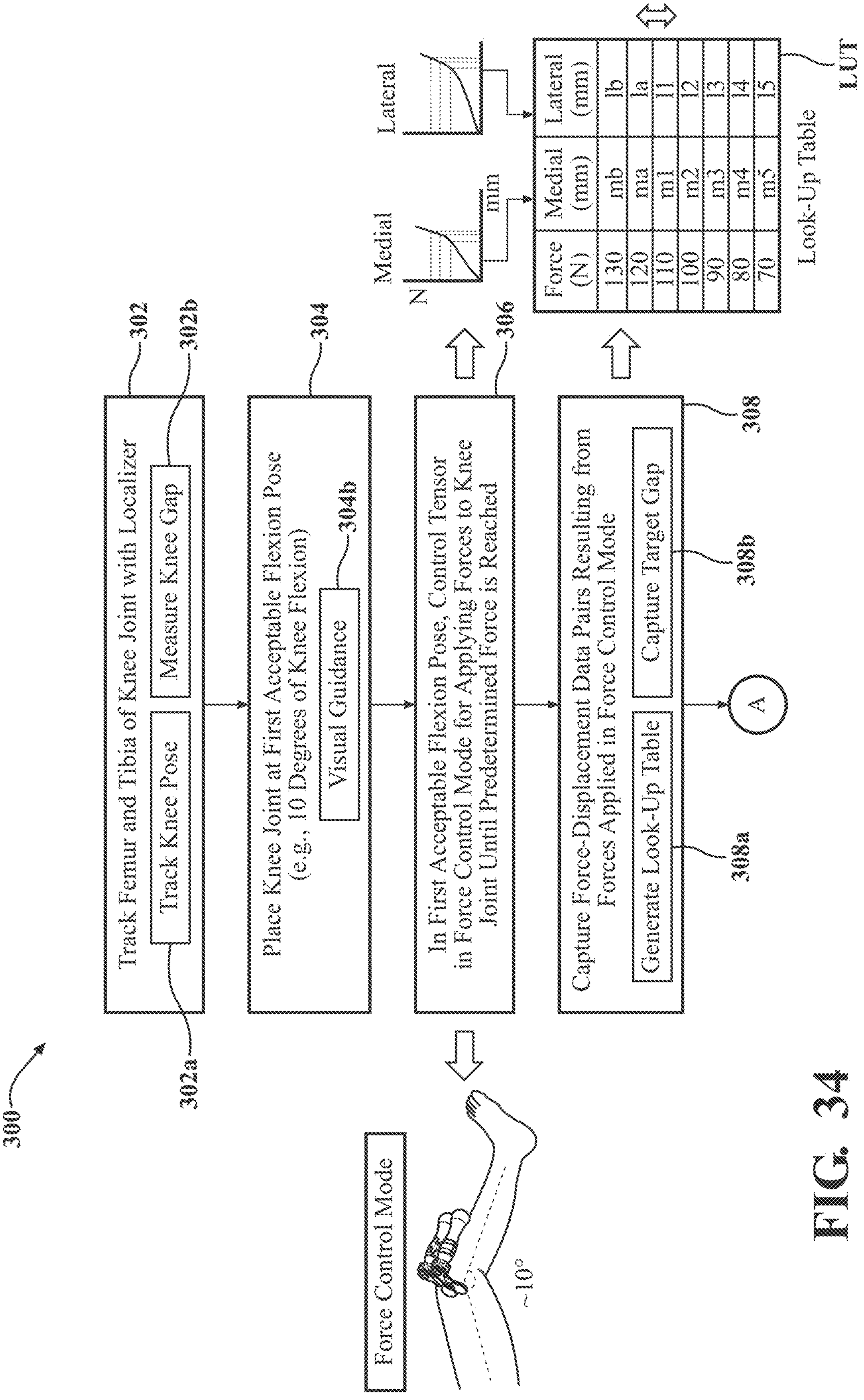
FIG. 34 is a first part of a flowchart of another method of utilizing the tensor to evaluate the anatomical joint, according to one implementation.
Figure 35:
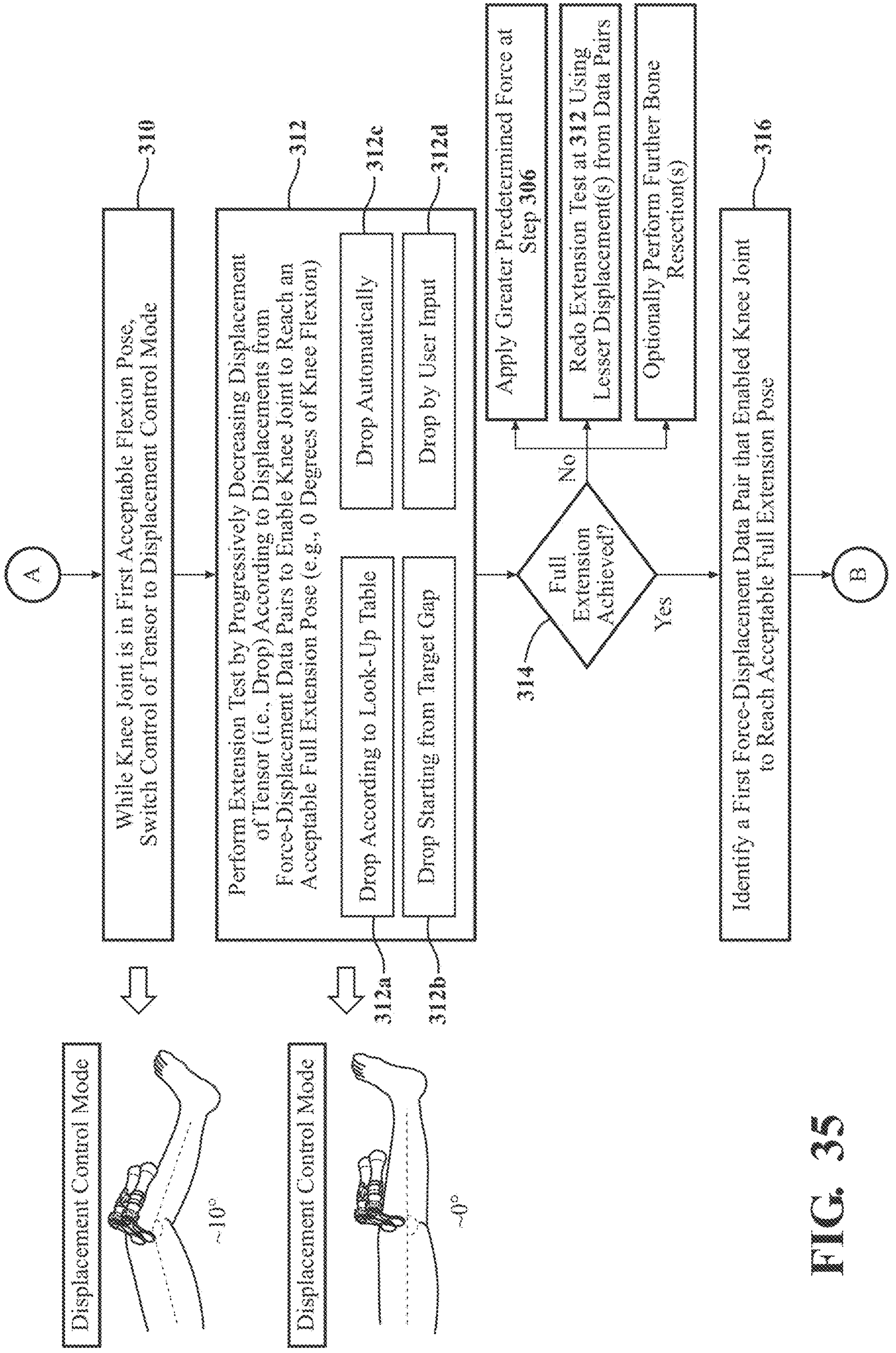
FIG. 35 is a second part of the flowchart of the method of utilizing the tensor to evaluate the anatomical joint, according to one implementation.
Figure 36:
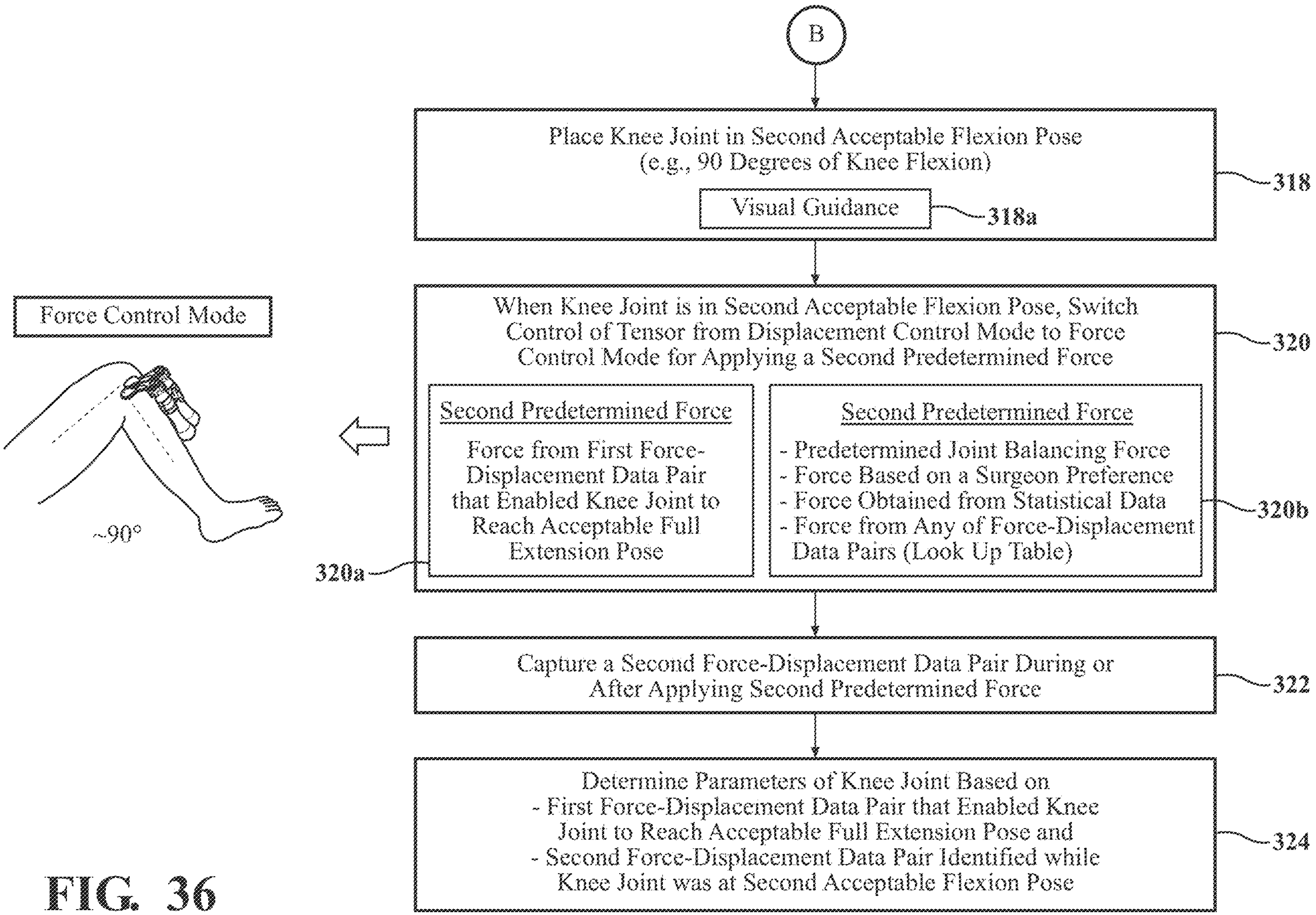
FIG. 36 is a third part of the flowchart of the method of utilizing the tensor to evaluate the anatomical joint, according to one implementation.

With reference to FIGS. 34-36, a method 300 is illustrated of utilizing the tensor T to evaluate the anatomical joint AJ, e.g., by performing the extension test. The steps of method 300 need not be performed in the order shown. Furthermore, the invention is not limited to require every step illustrated. There are possible uses for the tensor T which may utilize select steps in various order and for different uses other than assessing the extension of the knee joint. For example, the tensor T could use the certain steps of the described method 300 for assessing whether the knee joint could reach other poses, such as a mid-flexion pose or a flexion pose (such as ~90 degrees).

At step 302, the navigation system 32 utilizes the localizer 44 to track the femur F and the tibia TIB of the knee joint AJ. This can be performed using aspects of the tracking system described above, e.g., using the anatomical trackers 54, 56, or any other tracking modality. This step 302 is optional but can provide useful information to aid the surgeon in understanding the parameters of the knee joint AJ.

At 302*a*, the information from the localizer 44 can be utilized to dynamically track a pose of the knee joint AJ. The femur F and tibia TIB can be registered to the navigation system 32. By knowing the respective pose of the femur F and tibia TIB, the navigation controller 36 can compute the relationship between the respective long axes of the bones. FIG. 38-41 illustrate examples of a graphical user interface GUI of the clinical application CA that can show the output of tracking the femur F and tibia TIB on the display device 38. The graphical user interface GUI can show a virtual representation of the femur F' and the tibia T' and the pose of the virtual bones can dynamically be adjusted depending on the pose of the bones tracked by the localizer 44. The relationship between the bones can be a flexion/extension angle or a varus/valgus angle. For example, in FIG. 38, the knee joint is in 15 degrees flexion and the virtual representations F', TIB' are correspondingly shown in a 15 degrees flexed pose. Furthermore, the knee joint pose exhibits 2 degrees of varus alignment. The navigation system 34 can record the poses over time, including changes in the pose, and output pose data for display to the graphical user interface GUI. Additionally, or alternatively, such information can be presented on any of the displays described herein, including the head-mounted display.

At 302*b*, the information from the localizer 44 can be utilized to dynamically track a gap of the knee joint AJ. The gap is the spacing or distance between a surface of the femur F and a surface of the tibia TIB. When measuring the gap, the surface of any bone may be resected, non-resected, partially resected. Any resected surface may be smooth (such as a tibial resection) or irregular (such as for a revision procedure). Furthermore, the surface may be an articular surface of the bone or an existing implant in the bone. The articular surface may be a native articular surface (e.g., the native condyles of the femur), or an artificial articular surface (e.g., the artificial condyle components of a femoral implant or a surface of a trial implant). Computing the gap from the surfaces could be based on distal-most point(s) of each surface or could be based on an average taken from certain distal points. The navigation system 34 can record the gap over time, including changes in the gap, and output gap data for display to the graphical user interface GUI. In other cases, the gap can be measured based on virtual surfaces of the bones rather than actual surfaces. For example, 3D virtual models of the bones can be compared to determine the gap of the joint, e.g., at discrete poses or over a range of motion. Implants may be virtually planned relative to the 3D virtual bone models and the gap can be compared relative to the surfaces of the virtual implants. The tracked movements of the bones by the localizer 44 can cause corresponding movements of the virtual bone models and/or virtual implants to evaluate the gap. Any of the described examples of computing the gap can be used individually or in combination.

At step 304, the knee joint AJ is placed in a first acceptable flexion pose. The acceptable flexion pose is a pose of the knee joint between full extension and full flexion, e.g., a mid-flexion or semi-flexion pose. In one example, the first acceptable flexion pose can be a value between 2-15 degrees of knee joint flexion, such as 10 degrees (as illustrated in FIG. 34). The first acceptable flexion pose could be a single value or a range of values. The acceptability of the first acceptable flexion pose can be defined by the surgeon, the surgical plan, implant parameters, or be based on automated planning predictions made by the system 10. The term "first" is not intended to limit the first acceptable flexion pose to being the initial pose of the knee joint, but rather used as a modifier to distinguish this knee pose from others described herein. In other examples, as will be described below, the knee joint AJ can initially be placed in a mid-flexion or semi-flexion pose (e.g., ~90 degrees).

Figure 38:
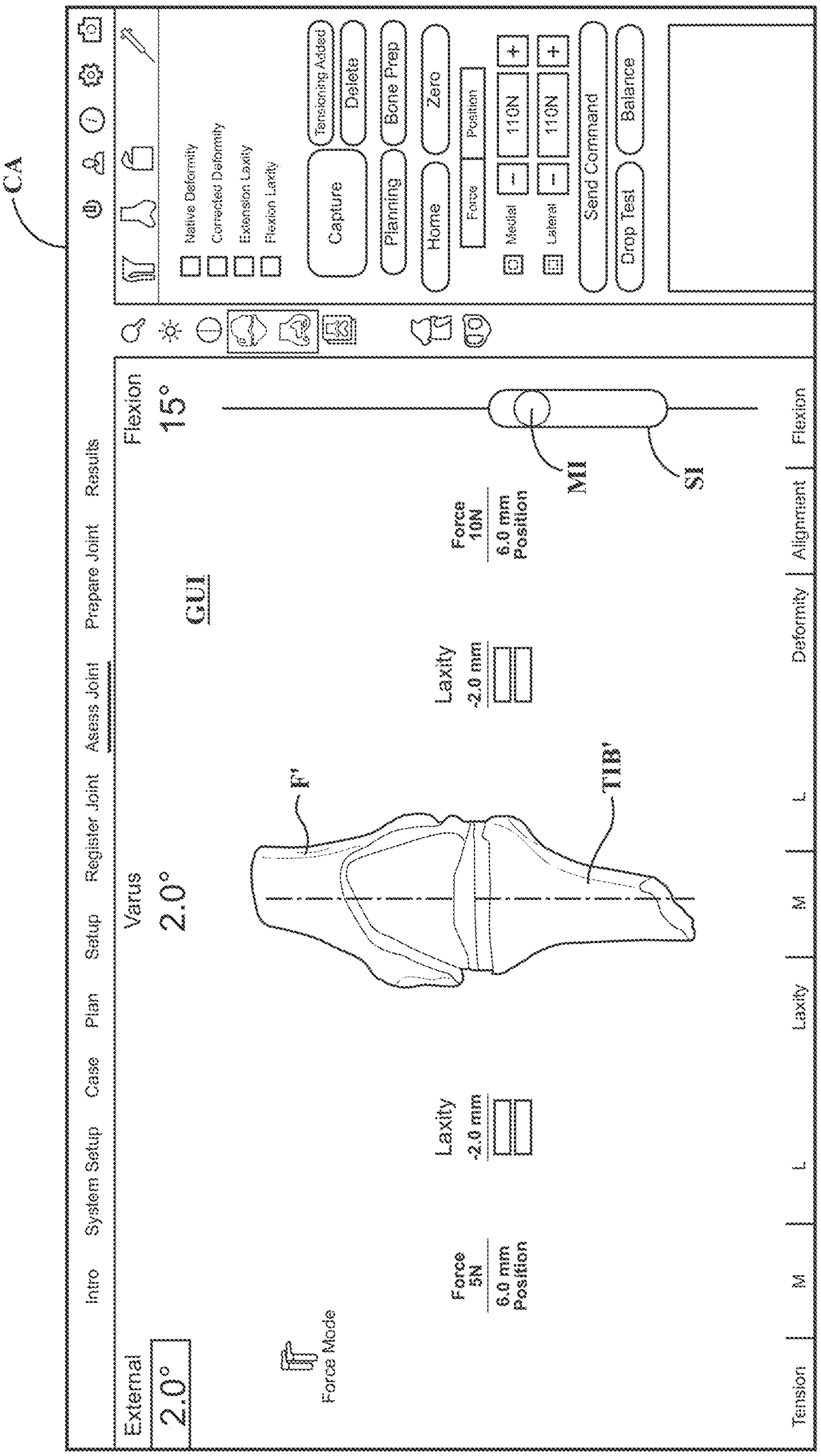
FIG. 38 illustrates a first example of a graphical user interface, provided on a display device, which can be utilized with the tensor and its methods of use, according to one implementation.

The process of placing the knee joint AJ in the any pose described herein (including the first acceptable flexion pose) can be a manual, automated or semi-automated process. When manually performed, the surgeon or technician physically moves the knee joint AJ into the first acceptable flexion pose. At 304*b*, for example, the navigation system 34, using the graphical user interface GUI, can provide visual guidance to aid the surgeon or technician in placing the knee joint AJ into the first acceptable flexion pose. For example, as shown in FIG. 38, the GUI illustrates the angle of the current pose of the knee joint, in this case 15 degrees of flexion. The GUI can further represent the current pose of the knee joint AJ with a moving indicator MI. The moving indicator MI, in the example, is a shape object (e.g., circle) that moves along a bar pursuant to flexion of the knee joint. The bar indicates the total flexion range of the joint. A static indicator SI (e.g., an oval shape) is located on the bar in a region indicative of a range for the first acceptable flexion pose. When the moving indicator MI is within, or at, the static indicator SI range, the GUI can provide confirmation to the user that the knee joint is in the first acceptable flexion pose. The confirmation can be to change the color of cither indicator MI, SI, e.g., by changing the color to green. Additionally, or alternatively, the GUI can provide a textual or graphical indicator to convey that the knee joint is in the first acceptable flexion pose. The indicators shown are one of many possible examples of techniques to convey the aforementioned information. The inventors have contemplated other graphical techniques, such as showing a side view comparison between a representation of current pose of the knee joint and the first acceptable flexion pose.

Alternatively, the knee joint AJ can be placed in any pose described herein (such as the first acceptable flexion pose) automatically or semi-automatically. The automated or semi-automated movement may be predefined or set by a surgeon or staff. Parameters of the automated movement can be discrete positions, continuous motions, prescribed manners, target pose(s), target range(s), or the like. An anatomical manipulator, such as a robotically controlled limb holder, may be coupled to the knee joint AJ to provide automated motion at or between different poses. The automated manipulator may reposition and/or re-orient the knee joint AJ in any suitable manner. The anatomical manipulator can include mechanisms for extending or flexing the knee joint AJ. For example, the anatomical manipulator can be supported by a sled, which moves along a support bar. The automated movement may involve moving the sled along the support bar to accomplish a desired movement the knee joint AJ. The anatomical manipulator may also rotate or tilt the knee joint AJ medially or laterally (toward or away from a centerline of the patient). Securing mechanisms can be used for securing the other portions of the leg or knee to the holder. The anatomical manipulator can be locked in any given pose described herein. Of course, the anatomical manipulator may have various other configurations and may be manipulated in various other ways. In another implementation, the manipulator 14 itself is used as the anatomical manipulator. For instance, a limb holder end effector could be attachable to the manipulator 14 to enable movement of the knee joint AJ. Afterwards, the limb holder end effector can be swapped for the end effector 22 to manipulate tissue during the procedure. In this example, the one or more controllers 60, 36, 26 can control the manipulator 14 to move the limb holder end effector in any suitable automated fashion as described. In some instances, the force/torque sensor S can detect forces/torques that are indicative of target poses or target ranges of the knee joint AJ. The one or more controllers 60, 36, 26 can detect these forces/torques to identify that the knee joint AJ has been moved. In other implementations, the one or more controllers 60, 36, 26 can capture and analyze joint encoder data and/or joint motor torque to determine the knee joint AJ has been moved. The anatomical manipulator can be like those described in: US Patent Application Pub. No. 20190262203, entitled "Motorized Joint Positioner", U.S. Pat. No. 10,390,737, entitled "System and Method of Controlling a Robotic System for Manipulating Anatomy of a Patient During a Surgical Procedure", and/or U.S. patent application Ser. No. 18/135,280, entitled "Systems and Methods for Guided Placement of a Robotic Manipulator", the entire contents of each of which are hereby by reference in their entirety.

At step 306, the knee joint AJ has been placed in the first acceptable flexion pose and the tensor control system TCS controls the tensor T in the force control mode FCM to apply forces to the knee joint AJ until a predetermined force. For this step, the force control mode FCM can be automatically triggered by the tensor control system TCS in response to detection of the knee joint AJ being placed in the first acceptable flexion pose. Alternatively, the user may utilize the clinical application CA or the tensor input device(s) TID to selectively activate the force control mode FCM. The process of applying forces to the knee joint AJ can involve both tensor bodies TB1, TB2 of the tensor T. The upper paddle UP of the first tensor body TB1 engages one condyle (medial/lateral) of the femur F and the upper paddle UP of the second tensor body TB2 engages the other condyle (medial/lateral) of the femur F. The lower paddle LP of the first tensor body TB1 and the lower paddle LP of the second tensor body TB2 collectively engage the tibia. In one example, the tibia TIB is resected in a mid-resection workflow. In the force control mode FCM each respective upper paddle is commanded to move until the predetermined force is reached. The predetermined force can be detected by the sensor S within each tensor body TB1, TB2 and recorded by the tensor control system TCS. The applied force will gradually increase until the predetermined force is reached. For the tensor bodies TB1, TB2 commanded movement can be simultaneous or separate. In one example, the predetermined force is a value within the range of 50-150 N, such as 100 N. Other values and ranges of the predetermined force are contemplated. The predetermined force may be the same for both tensor bodies TB1, TB2, or could be different depending on a variety of factors, such as predetermined information about the laxity of the medial/lateral components, or the like. The predetermined force may be reached at the same time, or at various times, for medial and lateral compartments of the knee joint AJ.

At step 308, pursuant to applying the forces at step 306, the tensor control system TCS, optionally in conjunction with the navigation system 34, can capture a plurality of force-displacement data pairs. The process of obtaining these force-displacement data pairs advantageously provides for a testing or sampling of the laxity of the knee joint in a non-fully extended pose instead of the fully extended pose, which presents challenges for evaluating the knee joint. As will be described below, one of the force-displacement data pairs can present an optimal data set for enabling the knee joint to reach full extension. The force-displacement data pairs each include one force measurement and one displacement measurement. For a plurality of discrete forces applied at step 306, a corresponding displacement of the knee joint AJ is captured. In one example, each corresponding displacement value is the displacement between the upper paddle UP and lower paddle LP for each respective tensor body TB. The displacement can be measured using the tensor encoder EN described above. In another example, each corresponding displacement value is the gap of the knee joint as measured by the localizer 44. The force-displacement data pairs can be captured separately for the medial and lateral compartments, e.g., using tensor bodies TB1, TB2. In one example, at 308*b*, the tensor control system TCS, and/or navigation system 34, can generate a look-up table LUT (as illustrated in FIG. 34) based on the plurality of force-displacement data pairs. The look-up table LUT may be visualized to the user using the graphical user interface GUI or may be hidden from the user but stored for back-end use. In the example shown, the look-up table LUT illustrates seven discrete forces applied at step 306, ranging from 70N-130N. For each discrete force, a corresponding medial and lateral displacement is provided. The data from the look-up table LUT can be utilized to generate laxity curves for the medial and lateral components, which can also be visualized using the GUI.

At 308*b*, the tensor control system TCS, and/or navigation system 34, can capture a target displacement of the tensor T at a time when the predetermined force was reached. The target displacement can be indicative of a target gap of the knee joint. The target gap can be an optimal or preferred gap of the knee joint. As described, the navigation system 34 can utilize the localizer to measure the gap of the knee joint. The target gap may be utilized in a later step (312) during which the extension test is performed.

FIG. 38 illustrates what the GUI may display during the process of steps 306 and 308. The knee joint is virtually represented in the first acceptable flexion pose (e.g., 15 degrees). Digital buttons are provided on the GUI for selecting the mode of operation. The GUI indicates the selected mode of operation of the tensor T, i.e., the force control mode. The predetermined force (e.g., 110N) can be selected and set on the GUI for the medial and lateral compartments. The GUI may include a "send command" button for triggering the tensor T to apply the predetermined forces. Real time force-displacement data (e.g., Force X N, Position X mm) can be shown for the medial and lateral compartments. Real time laxity values (e.g., X mm) can be shown for the medial and lateral compartments. Laxity can be shown using a bar graph that can show directionality in the positive (up) or negative (down) direction depending on the laxity values. This GUI or any aspects thereof can be presented on any of the displays described herein, including the head-mounted display.

In FIG. 35, the method 300 continues to step 310 from step 308 in FIG. 34. At step 310, the tensor control system TCS switches the tensor T from the force control mode FCM to the displacement control mode DCM. For this step 310, the mode switch can be automatically triggered by the tensor control system TCS in response to capturing of the force-displacement data pairs. Alternatively, the user may utilize the clinical application CA or the tensor input device(s) TID to selectively activate the displacement control mode DCM. This step can be performed while the knee remains in the first acceptable flexion pose. Furthermore, this step can be performed while the medial and lateral compartments remain under tension from the tensor T applying the forces (after step 308). For example, the pose of the tensor T may be locked after reaching the predetermined force and the tensor T can be switched to the displacement control mode DCM while the tensor T remains in this locked pose. Alternatively, in response to switching to the displacement control mode DCM, the tensor T can assume a nominal or default pose, such as a closed paddle state.

At step 312, with the tensor T being in the displacement control mode DCM, the extension test can begin. The tensor control system TCS can control the tensor T in the displacement control mode DCM to perform the extension test by commanding or changing displacement of the tensor T according to displacements from the plurality of force-displacement data pairs (captured at step 308). In one example, the tensor T progressively decreases (e.g., drops or lowers) the displacement of the upper paddle UP (relative to the lower paddle LP) according to displacements from the plurality of force-displacement data pairs. When two tensor bodies TB1, TB2 are utilized, the tensor T progressively decreases the displacement of the medial upper paddle UP of one body TB and the lateral upper paddle UP of the other body TB, according to respective medial and lateral displacements from the plurality of force-displacement data pairs.

Progressively decreasing the displacement of the upper paddle(s) UP can be performed according to various methods. In one example, at 312*a*, the tensor T can lower the upper paddle UP according to the specific values of displacement stored in the look-up table LUT. For example, the tensor control system TCS first drops to upper paddle UP to the largest displacement value from the table LUT, then drops the upper paddle UP to the second largest displacement value from the table LUT, etc. The process can continue for each displacement value, in decreasing order, as needed to conclude the extension test. For example, the process can continue until a displacement value is identified that enabled the knee to reach the acceptable full extension pose (as will be described below at 316). Alternatively, the process can continue for each displacement value, in decreasing order, until the last (or smallest) displacement value from the table LUT is reached. When transitioning from one displacement value to the next, the tensor control system TCS can continuously or smoothly transition between displacement values or can wait a predetermined amount of time (e.g., 1 second) between transitions. Advantageously, as will be described below, by lowering the upper paddle UP according to the specific values of displacement stored in the table LUT, the tensor control system TCS can make correlations to the forces in table LUT to make determinations about parameters of knee joint.

Additionally, or alternatively, at 312*b*, progressively decreasing the displacement of the upper paddle(s) UP can be performed with reference to the target displacement. As described at 308*b*, the target displacement of the tensor T can be captured at a time when the predetermined force was reached. The target displacement can be indicative of a target gap of the knee joint. Prior to performing the extension test, the tensor control system TCS can control the tensor T in the displacement control mode DCM to place the tensor T at the target displacement and/or perform the extension test by progressively decreasing the displacement of the tensor T starting from the target displacement. Here, the lowering of the upper paddle UP can be progressively decreased (starting from the target displacement) as needed to conclude the extension test. For example, the paddle UP can be lowered according to the displacement values from the data pairs, or until the paddles reached a predetermined state, e.g., a fully closed state.

In one implementation, at 312*c*, the tensor control system TCS can perform the extension test by automatically decreasing the displacement of the tensor T. In other words, once the extension test is commanded, the tensor T automatically lowers the upper paddle UP according to the displacement from the data pairs (and without further user intervention). The automatic extension test can be triggered through the clinical application CA and/or through user input TID devices on the tensor T itself.

In another implementation, at 312*d*, the tensor control system TCS can perform the extension test by decreasing the displacement of the tensor T according to user input. The user can utilize the clinical application CA and/or user input TID devices on the tensor T itself to provide input to the tensor control system TCS to drop the upper paddle UP to a first displacement from the data pairs. Once the first displacement is reached, the user provides a subsequent input to the tensor control system TCS to drop the upper paddle UP to the next displacement from the data pairs. This process can be repeated as needed to conclude the extension test.

The process of performing the extension test on the knee joint AJ can involve both tensor bodies TB1, TB2 of the tensor T. The upper paddle UP of the first tensor body TB1 engages one condyle (medial/lateral) of the femur F and the upper paddle UP of the second tensor body TB2 engages the other condyle (medial/lateral) of the femur F. The lower paddle LP of the first tensor body TB1 and the lower paddle LP of the second tensor body TB2 collectively engage the tibia. In one example, the tibia TIB is resected in a mid-resection workflow. In the displacement control mode DCM, each respective upper paddle is commanded to move according to displacement values specifically captured for the respective tensor body and medial and lateral compartments. The commanded displacements can be detected by the encoder EN within each tensor body TB1, TB2 and recorded by the tensor control system TCS. The commanded displacements for the upper paddles UP can be simultaneous or separate. The commanded displacements may be the same for both tensor bodies TB1, TB2, or could be different depending on a variety of factors, such as predetermined information about the laxity of the medial/lateral components, or the like. The acceptable full extension pose can be reached at the same time, or at various times, for medial and lateral compartments of the knee joint AJ.

Pursuant to any variation or combination of techniques described above at step 312, the tensor T displacement is progressively decreased in attempt to assess whether the knee joint AJ to reach the acceptable full extension pose.

Hence, the method 300 includes a step at 314 of evaluating whether the knee joint AJ is able to reach the acceptable full extension pose pursuant to the extension test. As described above, the acceptable full extension pose may be a full extension (e.g., ~0 degrees of knee flexion). Alternatively, depending on the patient soft tissue and bony anatomy, as well as surgeon preferences, and surgical plan, the acceptable full extension pose may not be a completely full extension. For example, the acceptable full extension can be any value within a range of −1 to 5 degrees of full extension.

It is possible that the knee joint AJ is unable to reach the acceptable full extension pose pursuant to the extension test. For example, the ligaments of the knee joint AJ may exhibit flex contracture or hyperextension preventing full extension. If the knee joint AJ is unable to reach the acceptable full extension pose, the method 300 can return to any prior one of step 306, 308, 310, and 312 to re-execute aspects of the method.

For example, if hyperextension is present at step 314, then step 306 can be re-performed, whereby in the first acceptable flexion pose, the tensor can be controlled in the force control mode to apply forces to the knee joint until an incrementally greater predetermined force is reached (as compared with the predetermined force utilized in the first iteration). For example, the greater predetermined force can be chosen to be incrementally higher than the highest force value of the prior look-up table LUT. Based on the greater predetermined force, the captured force-displacement pairs will change and the look-up table LUT will be repopulated (at step 308). Then, steps 310 and 312 can be redone to determine if the knee joint reaches the acceptable full extension pose.

If flex contracture is present at step 314, the input parameters of the extension test can be changed. For example, alternative displacement values from the data-pairs (e.g., from step 308) may be utilized to perform the extension test. The alternative displacement values could be displacement values from the table LUT that were not utilized in the first iteration of the extension test. These displacement values may be, for example, displacement values that are lesser than the smallest displacement value utilized in the first iteration of the extension test. For instance, the first iteration may have utilized, from the table LUT, displacement values of 13, 12.5, 12, 11.5, 10, and 9 mm. On the second iteration, the parameters of the extension test can be modified to lower the range of the displacement values to: 12.5, 12, 11.5, 10, 9, and 8 mm. The alternative displacement values can be from the table LUT or interpolated or predicted based on the previously utilized displacement values using any statistical or mathematical approach, such as linear regression, standard deviation, or the like. The second iteration can then be executed using any variation or combination of the techniques described at step 306, 308, 310 and 312 to determine if the full extension pose can be reached. If the acceptable full extension pose cannot be reached, the surgeon may be required to resect more material from one or both bones prior to re-performing any one of steps 306-312.

If the knee joint AJ is unable to reach the acceptable full extension pose, it is also contemplated that the method 300 can return to step 306 to re-perform the process of applying forces to the knee joint until the predetermined force is reached. Here, the predetermined force can be adjusted. For instance, the predetermined force can be increased or decreased, thereby changing the force-displacement data pair values that will be subsequently captured. The predetermined force can also be computed or predicted based on the force values from the table LUT. For instance, the predetermined force can be increased by a default value of 10%. In another example, the predetermined force may be computed, or predicted, based on the smallest displacement value utilized in the first iteration of the extension test.

Ideally, as a result of the methodical considerations described herein, the knee joint AJ should be able to reach the acceptable full extension pose pursuant to performing the extension test only one time. If so, the method 300 proceeds to step 316. At 316, during, or after completion of, the extension test, the tensor control system TCS can identify a first force-displacement data pair that enabled the knee joint AJ to reach the acceptable full extension pose. In other words, when the knee joint AJ reaches the acceptable full extension pose, it would have reached so according to a commanded displacement by the tensor T, wherein the commanded displacement includes a corresponding force value. The first force-displacement data pair includes the value of the displacement that enabled the knee to reach the acceptable full extension pose, as well as the force value corresponding to the displacement value. The term "first" with respect to first force-displacement data pair is merely used to distinguish this data pair from others that will be described below. The term "first" is not limited to mean that the data pair is the initial or first data pair in a list of data pairs.

Figure 39:
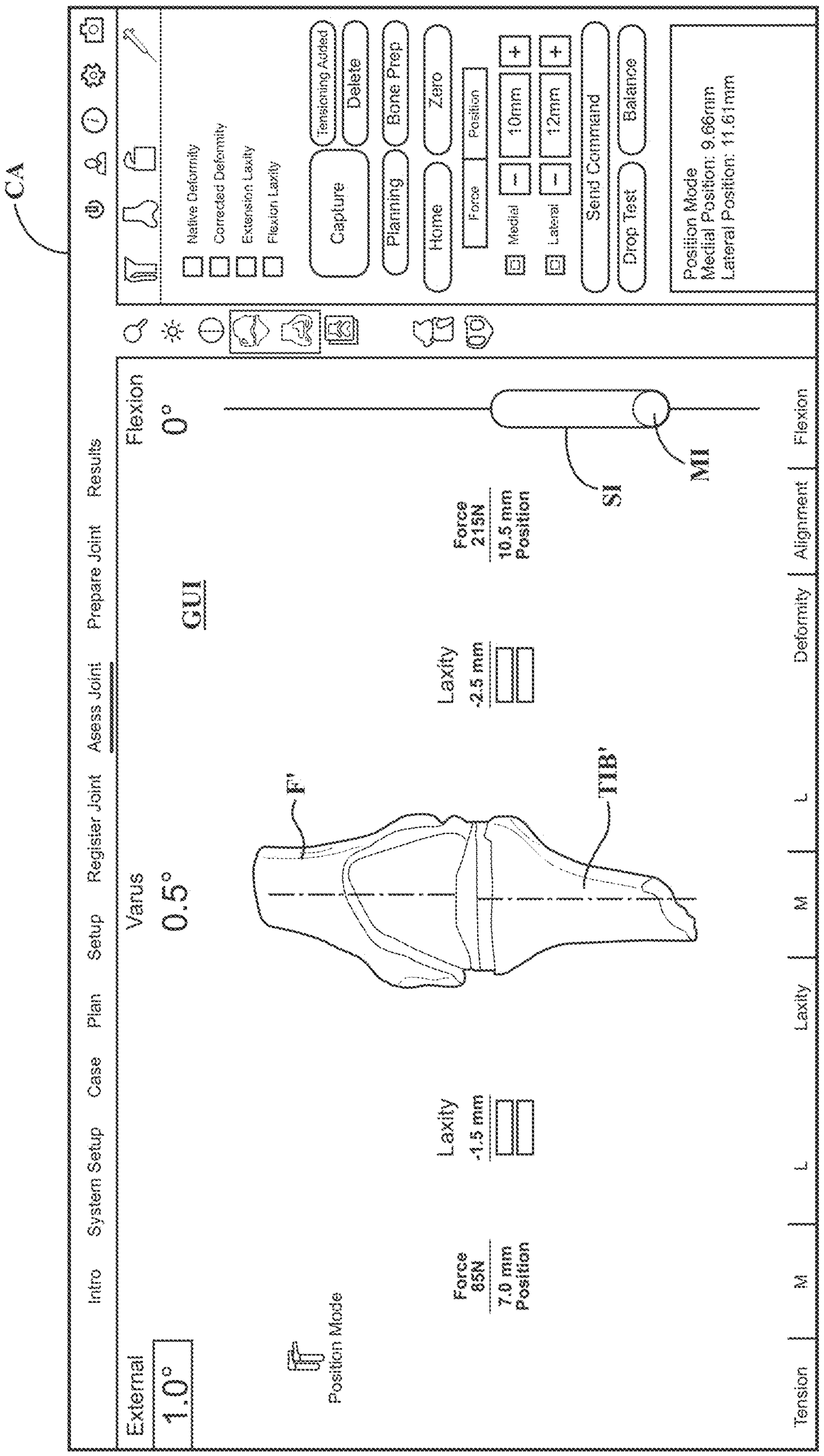
FIG. 39 illustrates a second example of a graphical user interface, provided on a display device, which can be utilized with the tensor and its methods of use, according to one implementation.

FIG. 39 illustrates what the GUI may display after successful completion of the extension test. The knee joint is virtually represented in the acceptable full extension pose (e.g., 0 degrees flexion). The GUI illustrates the angle of the current pose of the knee joint, in this case 0 degrees of flexion. The GUI can provide confirmation that the knee joint reached the acceptable full extension pose by illustrating the moving indicator MI being within, or at, the static indicator SI range for the acceptable full extension pose and optionally changing the of cither indicator MI, SI. Additionally, or alternatively, the GUI can provide a textual or graphical indicator to convey that the knee joint has reached the acceptable full extension pose. The GUI also indicates the selected mode of operation of the tensor T, i.e., the displacement control mode. The GUI may include a "send command" button for triggering the tensor T to perform the extension test. The identified first force-displacement data pairs (e.g., Force X N, Position X mm) from step 316 can be shown for the medial and lateral compartments, respectively. Real time laxity values (e.g., X mm) can be shown for the medial and lateral compartments.

In FIG. 36, the method 300 continues to step 318 from step 316 in FIG. 35. At step 318, the knee joint AJ is placed in a second acceptable flexion pose. The second acceptable flexion pose can be a mid-flexion or semi-flexed pose of the knee joint. In one example, the second acceptable flexion pose can be a value from 80-105 degrees of knee joint flexion, such as 90 degrees (as illustrated in FIG. 36). The second acceptable flexion pose could be a single value or a range of values. The acceptability of the second acceptable flexion pose can be defined by the surgeon, the surgical plan, implant parameters, or be based on automated planning predictions made by the system 10. As described, the process of placing the knee joint AJ in the any pose described herein (including the second acceptable flexion pose) can be a manual, automated or semi-automated process. When manually performed, the surgeon or technician physically moves the knee joint AJ into the second acceptable flexion pose.

Figure 40:
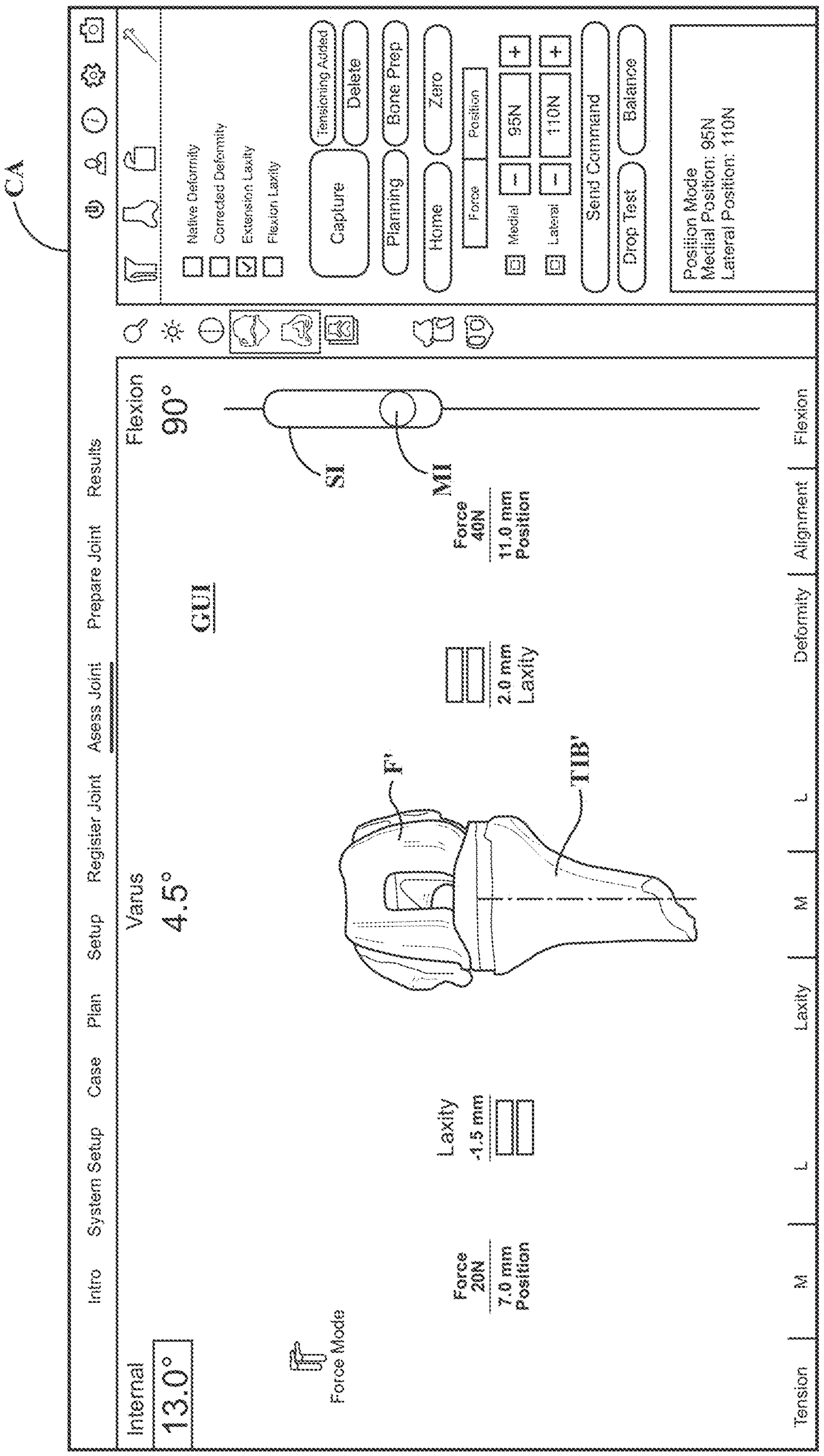
FIG. 40 illustrates a third example of a graphical user interface, provided on a display device, which can be utilized with the tensor and its methods of use, according to one implementation.

At 318*a*, the navigation system 34, using the graphical user interface GUI, can provide visual guidance to aid the surgeon or technician in placing the knee joint AJ into the second acceptable flexion pose. For example, as shown in FIG. 40, the GUI illustrates the angle of the current pose of the knee joint, in this case 90 degrees of flexion. The GUI can further represent the current pose of the knee joint AJ with the moving indicator MI relative to the static indicator SI representing the second acceptable flexion pose. When the moving indicator MI is within, or at, the static indicator SI range, the GUI can provide confirmation to the user that the knee joint is in the second acceptable flexion pose. The confirmation can be to change the color of either indicator MI, SI, e.g., by changing the color to green. Additionally, or alternatively, the GUI can provide a textual or graphical indicator to convey that the knee joint is in the second acceptable flexion pose. In another example, the GUI can provide a side view comparison between a representation of current pose of the knee joint and the second acceptable flexion pose. Furthermore, the knee joint AJ can be placed in any pose described herein (such as the second acceptable flexion pose) automatically or semi-automatically using the anatomical manipulator, described above (and not repeated for simplicity in description).

At step 320, when the knee joint AJ is in the acceptable full extension pose, the tensor control system TCS switches control of the tensor T from the force control mode FCM to the displacement control mode DCM. Here, the tensor control system TCS controls the tensor T in the force control mode FCM to apply a second predetermined force to the knee joint when the knee joint is in a second acceptable flexion pose. The term "second" with respect to second predetermined force is merely utilized to distinguish from the predetermined force applied in step 306. The term "second" effectively means "another" force and is not limited to specifically mean the second force in a sequence of forces.

For step 320, the force control mode FCM can be automatically triggered by the tensor control system TCS in response to detection of the knee joint AJ being placed in the second acceptable flexion pose. Alternatively, the user may utilize the clinical application CA or the tensor input device(s) TID to selectively activate the force control mode FCM. The process of applying the second predetermined force to the knee joint AJ can involve both tensor bodies TB1, TB2 of the tensor T. The upper paddle UP of the first tensor body TB1 engages one condyle (medial/lateral) of the femur F and the upper paddle UP of the second tensor body TB2 engages the other condyle (medial/lateral) of the femur F. The lower paddle LP of the first tensor body TB1 and the lower paddle LP of the second tensor body TB2 collectively engage the tibia. In one example, the tibia TIB is resected in a mid-resection workflow. In the force control mode FCM each respective upper paddle is commanded to move until the second predetermined force is reached. The second predetermined force can be detected by the sensor S within each tensor body TB1, TB2 and recorded by the tensor control system TCS. The applied force will gradually increase until the second predetermined force is reached. For the tensor bodies TB1, TB2 commanded movement can be simultaneous or separate. The second predetermined force may be the same for both tensor bodies TB1, TB2, or could be different depending on a variety of factors, such as predetermined information about the laxity of the medial/lateral components, or the like. The second predetermined force may be reached at the same time, or at various times, for medial and lateral compartments of the knee joint AJ.

The second predetermined force that is applied at step 320 can be derived or obtained from various sources. At 320*a*, the tensor control system TCS can obtain the second predetermined force from a force value of the first force-displacement data pair that enabled the knee joint to reach the acceptable full extension pose (at step 316). Advantageously, by using the force from the first force-displacement data pair, the knee joint can be tensioned in the second acceptable flexion pose using a force value that was captured (but not applied) while the knee was in the acceptable full extension pose. The process of extracting this force value from its corresponding displacement value avoids having to forcibly distract the knee joint with the tensor T in the full extension pose. In turn, the force value is an accurate measurement that is not subjected to inaccuracies resulting from posterior capsule tightness in the fully extended pose. Alternatively, or additionally, at 320*a*, the tensor control system TCS can obtain the second predetermined force from a predetermined joint balancing force, a force based on a surgeon preference, a force obtained from statistical data, or any force from any of the force-displacement data pairs.

At step 322, pursuant to applying the second predetermined forces at step 320, the tensor control system TCS, optionally in conjunction with the navigation system 34, can capture or identify a second force-displacement data pair. The process of obtaining the second force-displacement data pair advantageously provides for a testing or sampling of the laxity of the knee joint in the second acceptable flexion pose. The term "second" with respect to second force-displacement data pair is merely utilized to distinguish from the first force-displacement data pair identified in step 316. Here, the term "second" effectively means "another" force-displacement data pair and is not limited to specifically mean the second data pair in a sequence or table of data pairs. The second force-displacement data pair includes one force measurement and one displacement measurement. The second force-displacement data pair can include a force component that is the second predetermined force that was applied at step 320. Alternatively, the second force-displacement data pair can include a force component that is different, or less than, the second predetermined force that was applied at step 320. The displacement component of the second force-displacement data pair can be the displacement of the knee joint AJ that was reached pursuant to the second predetermined force applied at step 320. The displacement can be derived from the displacement of the upper paddle UP and/or derived from the gap of the knee joint as measured by the localizer 44 tracking the bones. At step 322, it is contemplated that the tensor control system TCS, and/or navigation system 34, can generate another look-up table LUT (similar to that illustrated in FIG. 34) which includes another set of force-displacement data pairs. The second force-displacement data pair can be selected from the look-up table LUT. Two separate second force-displacement data pairs can be captured for the respective medial and lateral compartments, e.g., using tensor bodies TB1, TB2. In this case, the second force-displacement data pairs can have force and/or displacement values that are the same as one another, or different from one another.

Figure 41:
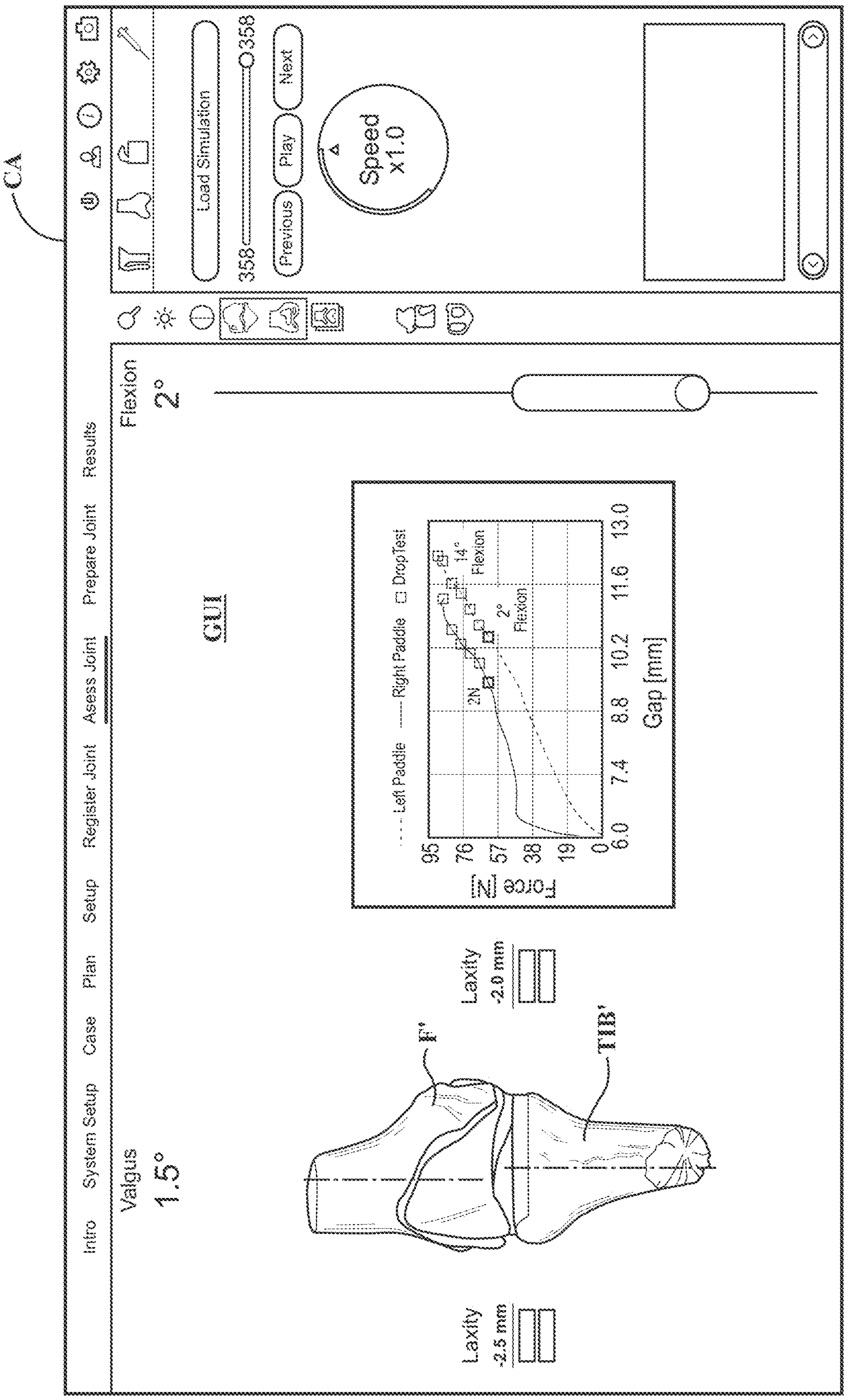
FIG. 41 illustrates a fourth example of a graphical user interface, provided on a display device, which can be utilized with the tensor and its methods of use, according to one implementation.

At step 324, the tensor control system TCS, and optionally in conjunction with the navigation system 34, can determine parameters of the knee joint AJ based on (1) the first force-displacement data pair (from step 316) that enabled the knee joint to reach the acceptable full extension pose and based on (2) the second force-displacement data pair (from step 322) identified while the knee joint was at the second acceptable flexion pose. The parameters can be laxity, stiffness, ligament balance, kinematics, flexion, extension and/or range of motion of the anatomical joint AJ. The parameters can be laxity of medial and lateral compartments of the knee joint. For instance, the two force-displacement data pairs can provide four laxity data points (two force and two displacement) defined in the range of full extension to full or near full flexion (90-120 degrees). FIG. 41 illustrates one example of knee parameters that can be provided by the GUI pursuant to application of the method 300 described above. The GUI can display a force-displacement curve for the medial and lateral components of the knee joint AJ. The force-displacement curve is derived from the data captured throughout performance of the above-described steps of the method 300, such as any one or more of steps 306, 308, 312, 316, 320, 322, and 324. The GUI can plot along the force-displacement curve several data points that were derived from the extension test. In this example, the extension test began at 14 degrees of flexion (in the first acceptable flexion pose) and concluded with the knee joint reaching 2 degrees of flexion (in the acceptable full extension pose). The flexion angle (14 and 2 degrees) of each pose is shown on the plot. Furthermore, the force (e.g., 2N) applied by one or both of the medial and lateral compartments at the completion of the extension test can be plotted. The discrete force-displacement data pairs that were captured at step 308 can also be plotted along the curve. The curve can be utilized by the surgeon to assess the mechanical properties of the soft tissues of the knee joint AJ. Based on the curve and patient-specific parameters (age, BMI, gender, etc.) the surgeon can evaluate the optimal tension for the specific patient's knee joint. Other curves, plots, or graphs can be created using the techniques described herein. For example, other types of data that can be visualized include, but are not limited to: displacement vs. time, force vs. time, displacement vs. flexion, force vs. flexion, gap vs. flexion, laxity vs. flexion, displacement vs. flexion, force vs. flexion, and/or any of the preceding utilized in conjunction with varus/valgus alignment.

The method 300 described with reference to FIGS. 34-36 includes placing the knee joint at the first acceptable flexion pose (e.g., ~10 degrees), enabling the knee joint to reach the acceptable full extension pose (e.g., 0 degrees), and placing the knee joint at the second acceptable flexion pose (e.g., ~90 degrees). It is contemplated to evaluate the knee at poses in addition to the preceding poses.

8B. Knee Extension Test—Alternative Workflow

Figure 37:
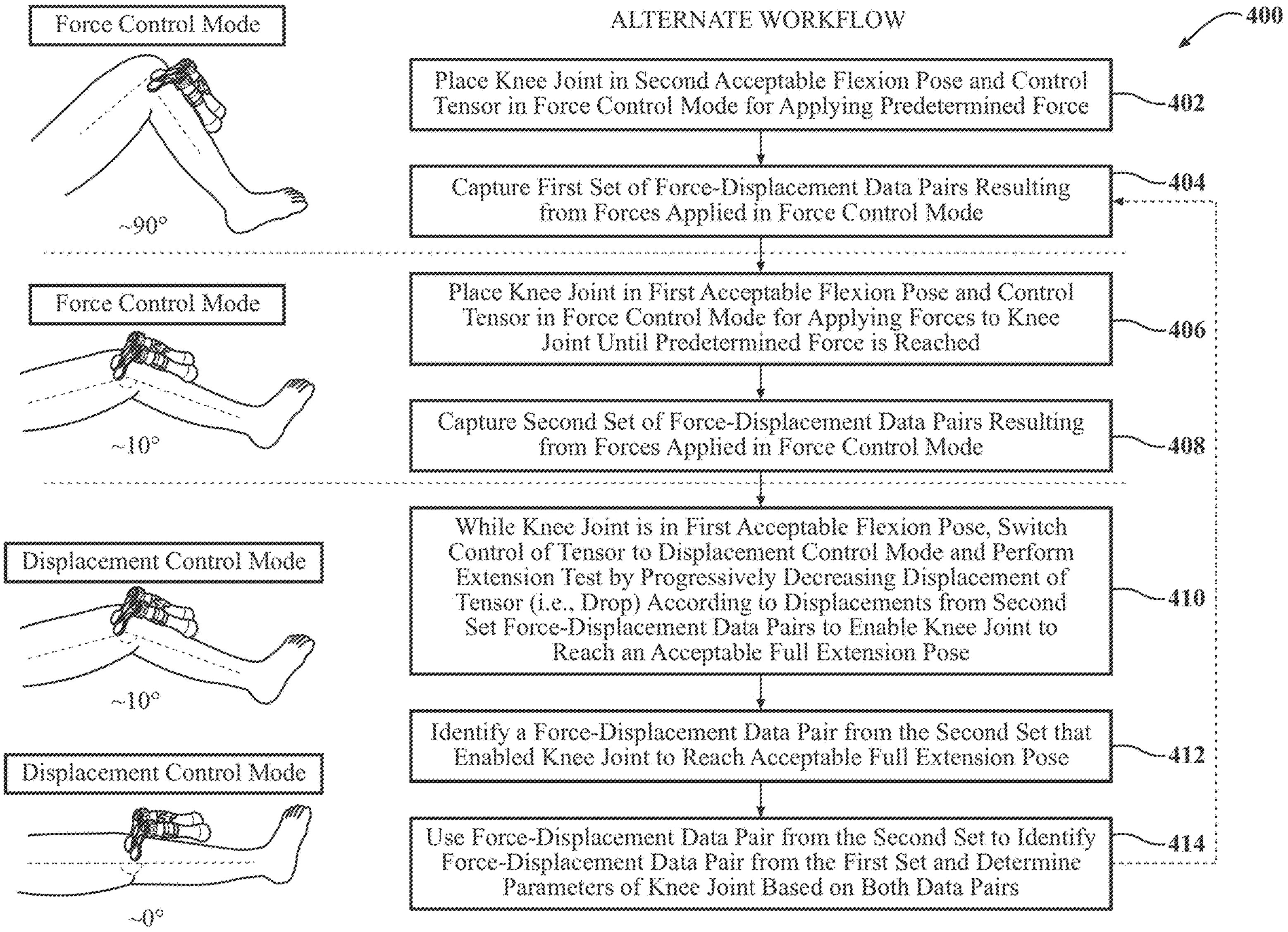
FIG. 37 is a flowchart of another method of utilizing the tensor to evaluate the anatomical joint, according to one implementation.

Additionally, and with reference to FIG. 37, it is contemplated to rearrange the steps of the method 300 to implement an alternative workflow for evaluating the knee joint AJ. The alternative workflow is described with reference to method 400. The alternative method 400 includes first placing the knee joint at the second acceptable flexion pose (e.g., ~90 degrees), then placing the knee joint at the first acceptable flexion pose (e.g., 10 degrees), then enabling the knee joint to reach the acceptable full extension pose (e.g., 0 degrees). This method 400 may provide unique advantages, such as convenience to the surgeon and reducing the duration of the surgical workflow. For a mid-resection workflow, the tibia TIB is resected typically while the knee joint AJ is in flexion (~90 degrees). The method 400 advantageously begins with the knee joint in the second acceptable flexion pose (e.g., ~90 degrees). Thus, the method 400 can be initiated without having to re-configure the knee joint AJ. The knee joint AJ will remain in substantially the same position it was after resection of the tibia TIB. The steps of the method 400, where applicable, can incorporate any and all of the implementations, functions, options, and features of the corresponding steps of method 300. Hence, certain aspects of method 400 are not repeated for simplicity in description.

At step 400, the knee joint AJ is placed in the second acceptable flexion pose (e.g., ~90 degrees) and the tensor control system TCS controls the tensor T in the force control mode FCM to apply a predetermined force to the knee joint AJ. At step 404, the tensor control system TCS, and optionally in conjunction with the navigation system 34, captures a first set of force-displacement data pairs resulting from the forces applied at step 402. These data pairs are stored for later use in the method 400. For example, as described above, the first set of force-displacement data pairs can be stored in a look-up table LUT. At step 406, the knee joint AJ is placed in the first acceptable flexion pose (e.g., 10 degrees) and the tensor control system TCS controls the tensor T in the force control mode FCM to apply forces to the knee joint AJ until a predetermined force is reached. This predetermined force can be the same as, or different from, the predetermined force applied at step 402. Either of these predetermined forces can be obtained from a predetermined joint balancing force, a force based on a surgeon preference, a force obtained from statistical data, or any force from any of the force-displacement data pairs. At step 408, the tensor control system TCS, and optionally in conjunction with the navigation system 34, captures a second set of force-displacement data pairs resulting from the forces applied at step 406. The second set of force-displacement data pairs may or may not have values that correspond to the values from the first set of force-displacement data pairs. At step 410, while the knee joint AJ remains in the first acceptable flexion pose (e.g., 10 degrees), the tensor control system TCS can switch operation of the tensor T to the displacement control mode DCM to perform the extension test. Here, the tensor T displacement is progressively decreased according to the displacement values from the second set of force-displacement data pairs. Similar to step 314 described above, an evaluation can be made regarding whether the knee joint was able to reach the acceptable full extension pose. Assuming the knee joint reaches the acceptable full extension pose, at step 412, the tensor control system TCS, and optionally in conjunction with the navigation system 34, identify a force-displacement data pair from the second set that enabled the knee joint to reach the acceptable full extension pose. At step 414, the tensor control system TCS, and optionally in conjunction with the navigation system 34, utilizes the force-displacement data pair from the second set to identify a force-displacement data pair from the first set (at 404). For example, the force and/or displacement value from the force-displacement data pair of the second set can be correlated, compared, or otherwise evaluated relative to force and/or displacement values from the first set. This process can be performed by comparing the rows or columns of the tables LUT to identify identical or substantially similar force or displacement values. Effectively, just like method 300 described above, the method 400 can utilize the two force-displacement data pairs to obtain four laxity data points (two force and two displacement) defined in the range of full extension to mid-flexion or full flexion. The method 400 can also be utilized to determine any other described parameters of the knee joint AJ.

8C. Paddle Deflection Compensation Techniques

Described herein are techniques for compensating for mechanical deflection of any paddle(s) of the tensor T in response to an applied load. For example, during execution of any of the described workflows, there is a possibility that one or more of the upper paddles UP in contact with a femoral condyle(s) can deflect mechanically. The deflection in the paddles is linear and can be measured. The measured displacement or force of the tensor T as observed by the sensors in the tensor T, can be compensated by predicting the corresponding deflection of the paddle(s) because the load experienced by the actuators of tensor T is a known quantity. For instance, when the extension pose is captured, the tensor T can be operated in position control mode. The force that is recorded for the extension pose can be determined using a lookup table that records a force-position mapping. The look up table can be configured to provide predicted paddle deflection. The look up table can be paddle specific and can correlate force on the paddle to deflection of the paddle. For example, for every N Newtons of force applied to the paddle, the paddle will deflect D mm from its at-rest state. Again, this mapping is based on a linear relationship between force and deflection. In other configurations, the look up table can be configured to provide a predicted distraction/force table for the tensor T, which is based on the predicted paddle deflection. The look up table can be stored in any appropriate non-transitory memory, such as one located in the tensor T or tensor body TB, or one located remote from the tensor.

During the surgical workflow, the commanded/measured force and/or distraction of the tensor T is captured. Suppose the commanded distraction is 9.5 mm at 95N of force. Using the values of the commanded/measured force and/or distraction, the look up table can be referenced to obtain a predicted deflection of the paddle or predicted distraction/force values. Suppose for 95N of force, the look up table provides a value of 1.5 of paddle deflection. Based on this, the controller(s) can adjust the commanded/measured distraction by the referenced deflection (e.g., 9.5 mm minus 1.5 mm) to produce a compensated final distraction value (or predicted distraction) of 8 mm that compensates for the paddle deflection resulting from the force. From here, a predicted force value can be obtained that corresponds to the predicted deflection value. For example, instead of the actual recorded 95N of force based on 9.5 mm of distraction, the predicted force can be adjusted to 85N based on 8.0 mm predicted distraction.

This paddle deflection compensation technique can be applied for force measurements or displacement measurements and can be applied for the force control mode, displacement control mode, and/or force-displacement control mode. Furthermore, paddle deflection compensation can be applied at any one or more steps of the described workflows 300, 400, or at the end of any of the described workflows (e.g., after all requisite measurements are recorded). The predicted values can be informed to the surgeon using a visual indicator (or new table column) on the software application (e.g., as a new column shown in the look up table LUT of FIG. 34) or can remain hidden to the user (by the software automatically adjusting the actual force/displacement values). By compensating for the paddle deflection in this manner, the techniques provide a more accurate representation of force and displacement for any stage of the surgical workflow.

9. Inverted Tensor Configuration and Use

The tensor T has been described in some examples above using a configuration whereby the upper paddle UP engages the femur and the lower paddle LP engages the tibia. In these examples, the lower paddle LP usually remains stationary and the upper paddle UP moves relative to the lower paddle LP. It is contemplated that this tensor T can be used in an alternative manner. For example, referring to FIG. 44, the tensor T can have the same configuration as described above, but the tensor T can be inverted (flipped upside down). In this example, the lower paddle LP remains stationary and the upper paddle UP moves relative to the lower paddle LP. However, the upper paddle UP engages the tibia instead of the femur and the lower paddle engages the femur instead of the tibia. During operation of the tensor T, the upper paddle UP pushes the tibia down (instead of pushing the femur up) and the lower paddle stationarily contacts the femur. This configuration can be enabled with paddle surfaces (e.g., flat surfaces) that are non-specific to the type of bone being engaged. Inverting the tensor T may be useful for many reasons, including but not limited to: surgeon ergonomics or comfort, avoiding contact between the tensor and a surgical object (e.g., such as bone pins, an anatomical tracker, retractor, incision opening, or cables of the tensor), or adapting to a specific pose of the knee. Advantageously, the same tensor T can be utilized in an upright orientation or an inverted orientation for a given procedure depending on the circumstances. In this inverted use, the term “upper” and “lower” paddle are utilized to maintain consistency in tensor description above but are not intended to limit the relative pose of the respective paddle. In other words, it is fully contemplated in this configuration for the upper paddle to be a lower paddle, and vice versa.

In another example, as shown in FIG. 45, the tensor T has an inverted configuration compared with the tensor T described and shown in the figures throughout. In FIG. 45, the tensor body TB extends upwards from the lower paddle LP. In other words, the lower paddle LP is located at the bottom of the tensor body TB (instead of near the top). The upper paddle UP remains located above the lower paddle LP. The lower paddle LP remains stationary and the upper paddle UP moves relative to the lower paddle LP. The described components within the tensor body TB, such as the displacement mechanism DM, are inverted. Hence, instead of the upper paddle UP pushing the femur up, the upper paddle UP pulls the femur up. This inverted tensor configuration can be beneficial for surgeon ergonomics or comfort, avoiding contact between the tensor and a surgical object (e.g., such as bone pins, an anatomical tracker, retractor, incision opening, or cables of the tensor), or adapting to a specific pose of the knee. The inverted tensor bodies TB can be coupled to the retainer R and used with any configuration of the described retainer R. Hence, the retainer R provides the surgeon with the ability to selectively swap upright and inverted tensor bodies TB during a procedure.

In another example, the tensor T may be configured such that a portion of the tensor body TB (e.g., the handle or gripping features G) is configured to swivel or pivot relative to the paddles or relative to the portion of the tensor body TB that includes the displacement mechanism DM for the paddles. The pivoting or swiveling of the moveable portion of the tensor body TB can enable the tensor body TB to have an inverted configuration, as described in FIG. 45. The pivot or swivel may be lockable to secure the movable portion of the tensor body TB in the set orientation. Using this technique, it is also contemplated that the portion of the tensor body TB can be oriented in other manners, such as at an angle (e.g., 45 degrees) relative to the other portion of the tensor body TB or the paddles to enable the tensor body TB to avoid obstacles.

Any of the features or configurations of the tensor T described in the prior sections can be fully implemented for the inverted use or inverted configuration of the tensor T described herein. For example, it is contemplated that both paddles UP, LP may move in the inverted use or inverted configuration of the tensor T, and the like.

Several embodiments have been described in the foregoing description. However, the embodiments discussed herein are not intended to be exhaustive or limit the invention to any particular form. The terminology, which has been utilized, is intended to be in the nature of words of description rather than of limitation. Many modifications and variations are possible in light of the above teachings and the invention may be practiced otherwise than as specifically described.

In reference to the disclosure provided above, for purposes of convenience and clarity only, directional terms such as top, bottom, above, upper, lower, proximal, distal, vertical, horizontal, etc., are used with respect to the context of the accompanying drawings and will be understood by those skilled in the art with respect to such context. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

What is claimed is:

1. A surgical system configured to evaluate a knee joint including a femur and a tibia, the surgical system comprising:

a tensor that is motorized and configured to operate in a force control mode and a displacement control mode, wherein the tensor comprises at least one force sensor and at least one displacement sensor; and a control system coupled to the tensor and being configured to:

control the tensor in the force control mode to apply forces to the knee joint at a first acceptable flexion pose until a predetermined force is reached, wherein the first acceptable flexion pose comprises a joint angle between the femur and the tibia that is greater than 2 degrees and less than 90 degrees;

capture, with the at least one force sensor and the at least one displacement sensor, a plurality of force-displacement data pairs from the tensor as a result of the forces applied by the tensor in the force control mode; and control the tensor to switch from the force control mode to the displacement control mode; and control the tensor in the displacement control mode to perform an extension test that begins with the knee joint at the first acceptable flexion pose and wherein a displacement of the tensor is progressively decreased according to displacements from the plurality of force-displacement data pairs until the knee joint can reach an acceptable full extension pose during, or after completion of, the extension test.

2. The surgical system of claim 1, wherein the surgical system further includes a localizer and a display device, and wherein the control system is configured to:

track a pose of the femur and a pose of the tibia with the localizer;

control the display device to provide visual guidance to aid in placing the pose of the knee joint in the first acceptable flexion pose;

capture, with the localizer, the pose of the knee joint relative to the first acceptable flexion pose; and control the display device to provide a visual confirmation in response to the pose of the knee joint being at the first acceptable flexion pose.

3. The surgical system of claim 1, wherein the surgical system further includes a localizer and a display device, and wherein the control system is configured to:

track a pose of the femur and a pose of the tibia with the localizer; and control the display device to provide a visual representation of a current pose of the knee joint based on the poses of the femur and the tibia tracked by the localizer.

4. The surgical system of claim 3, wherein the control system is configured to measure a gap of the knee joint based on the pose of the femur and the tibia tracked by the localizer.

5. The surgical system of claim 3, wherein the control system is configured to:

capture, with the localizer, the current pose of the knee joint relative to the acceptable full extension pose; and control the display device to provide a visual confirmation in response to the current pose of the knee joint being at the acceptable full extension pose.

6. The surgical system of claim 1, wherein the acceptable full extension pose comprises a joint angle between the femur and the tibia that is greater than or equal to 0 degrees and less than or equal to 2 degrees.

7. The surgical system of claim 1, wherein the control system is configured to:

generate a look-up table based on the plurality of force-displacement data pairs captured from the tensor; and perform the extension test according to displacements from the look-up table.

8. The surgical system of claim 1, wherein the control system is configured to:

capture a target displacement of the tensor at a time when the predetermined force was reached, the target displacement being indicative of a target gap of the knee joint; and prior to performing the extension test, control the tensor in the displacement control mode to place the tensor at the target displacement; and perform the extension test by progressively decreasing the displacement of the tensor starting from the target displacement.

9. The surgical system of claim 1, wherein the control system performs the extension test by being configured to automatically and progressively decrease the displacement of the tensor according to displacements from the plurality of force-displacement data pairs.

10. The surgical system of claim 1, wherein the tensor comprises a user control input, and wherein the control system performs the extension test by being configured to progressively decrease the displacement of the tensor in response to the user control input and according to displacements from the plurality of force-displacement data pairs.

11. The surgical system of claim 1, wherein during, or after completion of, the extension test, the control system is configured to identify a first force-displacement data pair that enabled the knee joint to reach the acceptable full extension pose.

12. The surgical system of claim 11, wherein, after completion of the extension test, the control system is configured to:

control the tensor to switch from the displacement control mode to the force control mode and control the tensor in the force control mode to apply a second predetermined force to the knee joint when the knee joint is in a second acceptable flexion pose.

13. The surgical system of claim 11, wherein, before the control system controls the tensor in the force control mode to apply forces to the knee joint until the predetermined force is reached, the control system is configured to:

control the tensor in the force control mode for applying a second predetermined force to the knee joint when the knee joint is in a second acceptable flexion pose.

14. The surgical system of claim 12, wherein the surgical system further includes a localizer and a display device, and wherein the control system is configured to:

track a pose of the femur and a pose of the tibia with the localizer; and control the display device to provide visual guidance to aid in placing a current pose of the knee joint at the second acceptable flexion pose;

capture the current pose of the knee joint relative to the second acceptable flexion pose; and control the display device to provide a visual confirmation in response to the current pose of the knee joint being at the second acceptable flexion pose.

15. The surgical system of claim 12, wherein the second acceptable flexion pose comprises a joint angle between the femur and the tibia that is greater than or equal to 80 degrees and less than or equal to 105 degrees.

16. The surgical system of claim 12, wherein the control system is configured to obtain the second predetermined force from a force from the first force-displacement data pair that enabled the knee joint to reach the acceptable full extension pose.

17. The surgical system of claim 12, wherein the control system is configured to obtain the second predetermined force from one of: a predetermined joint balancing force, a force based on a surgeon preference, a force obtained from statistical data, or a force from any of the force-displacement data pairs.

18. The surgical system of claim 12, wherein while the knee joint is at the second acceptable flexion pose and during, or after, application of the second predetermined force to the knee joint, the control system is configured to:

capture a second force-displacement data pair from the tensor.

19. The surgical system of claim 18, wherein the control system is configured to:

determine parameters of the knee joint based on the first force-displacement data pair that enabled the knee joint to reach the acceptable full extension pose and based on the second force-displacement data pair identified while the knee joint was at the second acceptable flexion pose.

20. The surgical system of claim 1, wherein the femur includes medial and lateral condyles, and wherein the tensor further comprises a medial upper paddle and a lateral upper paddle that are each separately movable and configured to respectively engage the medial and lateral condyles of the femur, and at least one lower paddle configured to engage the tibia, a drive assembly comprising a first electric motor, and a first displacement mechanism coupled between the first electric motor and the medial upper paddle, and a second electric motor, and a second displacement mechanism coupled between the second electric motor and the lateral upper paddle, the at least one force sensor comprising a first force sensor configured to sense force applied to the medial upper paddle and a second force sensor configured to sense force applied to the lateral upper paddle, the at least one displacement sensor comprising a first displacement sensor configured to measure displacement of the medial upper paddle and a second displacement sensor configured to measure a displacement of the lateral upper paddle, and wherein the control system is configured to:

control the tensor in the force control mode by being configured to command the medial upper paddle and the lateral upper paddle to respectively apply forces to the medial and lateral condyles of the femur until the predetermined force is reached for one or both of the medial upper paddle and the lateral upper paddle;

capture the plurality of force-displacement data pairs further based on measurements from the first and second force sensors and displacements of the medial upper paddle and the lateral upper paddle based on measurements from the first and second displacement sensors; and control the tensor in the displacement control mode to perform the extension test by being configured to progressively decrease the displacement of the medial upper paddle and the lateral upper paddle according to displacements from the plurality of force-displacement data pairs.

21. A method of utilizing a surgical system for evaluating a knee joint including a femur and a tibia, the surgical system comprising a tensor that is motorized and configured to operate in a force control mode and a displacement control mode, the tensor comprising at least one force sensor and at least one displacement sensor, and a control system configured to control the tensor, the method comprising:

controlling, with the control system, the tensor in the force control mode for applying forces to the knee joint at a first acceptable flexion pose until a predetermined force is reached, wherein the first acceptable flexion pose comprises a joint angle between the femur and the tibia that is greater than 2 degrees and less than 90 degrees;

capturing, with the control system and based on measurements from the at least one force sensor and the at least one displacement sensor, a plurality of force-displacement data pairs from the tensor resulting from the tensor applying forces in the force control mode; and controlling, with the control system, the tensor for switching from the force control mode to the displacement control mode; and controlling the tensor in the displacement control mode for performing an extension test beginning with the knee joint at the first acceptable flexion pose and by progressively decreasing a displacement of the tensor according to displacements from the plurality of force-displacement data pairs until the knee joint can reach an acceptable full extension pose during, or after completion of, the extension test.

22. The method of claim 21, wherein the surgical system further includes a localizer and a display device, the method comprising:

tracking a pose of the femur and a pose of the tibia with the localizer; and controlling, with the control system, the display device for providing a visual representation of a current pose of the knee joint based on the localizer tracking of the poses of the femur and the tibia.

23. The method of claim 21, wherein the acceptable full extension pose comprises a joint angle between the femur and the tibia that is greater than or equal to 0 degrees and less than or equal to 2 degrees.

24. The method of claim 21, further comprising:

generating, with the control system, a look-up table based on the plurality of force-displacement data pairs captured from the tensor; and performing the extension test according to displacements from the look-up table.

25. The method of claim 21, further comprising:

capturing, with the control system, a target displacement of the tensor at a time when the predetermined force was reached, the target displacement being indicative of a target gap of the knee joint; and prior to performing the extension test, controlling the tensor in the displacement control mode to place the tensor at the target displacement; and performing the extension test by progressively decreasing the displacement of the tensor starting from the target displacement.

26. The method of claim 21, wherein performing the extension test further occurs by the control system automatically and progressively decreasing the displacement of the tensor according to displacements from the plurality of force-displacement data pairs.

27. The method of claim 21, wherein the tensor comprises a user control input, and wherein performing the extension test further occurs by the control system progressively decreasing the displacement of the tensor in response to the user control input and according to displacements from the plurality of force-displacement data pairs.

28. The method of claim 21, wherein during, or after completion of, the extension test, further comprising:

identifying, with the control system, a first force-displacement data pair that enabled the knee joint to reach the acceptable full extension pose.

29. The method of claim 28, further comprising:

after completion of the extension test, moving a current pose of the knee joint to a second acceptable flexion pose; and controlling, with the control system, the tensor for switching from the displacement control mode to the force control mode and controlling the tensor in the force control mode for applying a second predetermined force to the knee joint in the second acceptable flexion pose.

30. The method of claim 28, further comprising:

before controlling, with the control system, the tensor in the force control mode for applying forces to the knee joint until the predetermined force is reached, moving a current pose of the knee joint to a second acceptable flexion pose; and controlling, with the control system, the tensor in the force control mode for applying a second predetermined force to the knee joint in the second acceptable flexion pose.

31. The method of claim 21, wherein the femur includes medial and lateral condyles, and wherein the tensor further comprises a medial upper paddle and a lateral upper paddle that are each separately movable and configured to respectively engage the medial and lateral condyles of the femur, and at least one lower paddle configured to engage the tibia, a drive assembly comprising a first electric motor, and a first displacement mechanism coupled between the first electric motor and the medial upper paddle, and a second electric motor, and a second displacement mechanism coupled between the second electric motor and the lateral upper paddle, the at least one force sensor comprising a first force sensor configured to sense force applied to the medial upper paddle and a second force sensor configured to sense force applied to the lateral upper paddle, the at least one displacement sensor comprising a first displacement sensor configured to measure displacement of the medial upper paddle and a second displacement sensor configured to measure a displacement of the lateral upper paddle, and wherein:

controlling, with the control system, the tensor in the force control mode further comprises commanding the medial upper paddle and the lateral upper paddle for respectively applying forces to the medial and lateral condyles of the femur until the predetermined force is reached for one or both of the medial upper paddle and the lateral upper paddle;

capturing, with the control system, the plurality of force-displacement data pairs further based on measurements from the first and second force sensors and displacements of the medial and lateral upper paddles based on measurements from the first and second displacement sensors; and controlling the tensor in the displacement control mode for performing the extension test is further defined by progressively decreasing the displacement of the medial and lateral upper paddles according to displacements from the plurality of force-displacement data pairs.

* * * * *